United States Patent
Lin et al.

(10) Patent No.: US 9,850,542 B2
(45) Date of Patent: Dec. 26, 2017

(54) GENE SIGNATURE TO PREDICT HOMOLOGOUS RECOMBINATION (HR) DEFICIENT CANCER

(71) Applicant: Board of Regents, The University of Texas System, Austin, TX (US)

(72) Inventors: Chun-Jen Lin, Houston, TX (US); Guang Peng, Houston, TX (US); Shiaw-Yih Lin, Pearland, TX (US); Gordon B. Mills, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 14/772,549

(22) PCT Filed: Mar. 4, 2014

(86) PCT No.: PCT/US2014/020376
§ 371 (c)(1),
(2) Date: Sep. 3, 2015

(87) PCT Pub. No.: WO2014/138101
PCT Pub. Date: Sep. 12, 2014

(65) Prior Publication Data
US 2016/0010159 A1    Jan. 14, 2016

Related U.S. Application Data

(60) Provisional application No. 61/772,406, filed on Mar. 4, 2013.

(51) Int. Cl.
| | | |
|---|---|---|
| *A61K 31/424* | (2006.01) | |
| *C12Q 1/68* | (2006.01) | |
| *G01N 33/574* | (2006.01) | |
| *A61K 31/167* | (2006.01) | |
| *A61K 31/436* | (2006.01) | |
| *A61K 31/502* | (2006.01) | |
| *A61K 31/5377* | (2006.01) | |
| *A61K 31/55* | (2006.01) | |

(52) U.S. Cl.
CPC .......... *C12Q 1/6886* (2013.01); *A61K 31/167* (2013.01); *A61K 31/436* (2013.01); *A61K 31/502* (2013.01); *A61K 31/5377* (2013.01); *A61K 31/55* (2013.01); *G01N 33/57415* (2013.01); *G01N 33/57423* (2013.01); *G01N 33/57442* (2013.01); *C12Q 2600/106* (2013.01); *C12Q 2600/112* (2013.01); *C12Q 2600/118* (2013.01); *C12Q 2600/158* (2013.01); *G01N 2800/52* (2013.01)

(58) Field of Classification Search
None
See application file for complete search history.

(56) References Cited

FOREIGN PATENT DOCUMENTS

WO    WO 2011-058367    5/2011

OTHER PUBLICATIONS

Fong et al (J Clin Oncol 28:2512-2519, 2010).*
Cheng et al (Gynecologic Oncology 117:159-169, 2010).*
Schlosshauer et al (Gynecologic Oncology 114:516-522, 2009).*
Audeh et al., "Oral poly(ADP-ribose) polymerase inhibitor olaparib in patients with BRCA1 or BRCA2 mutations and recurrent ovarian cancer: a proof-of-concept trial," *Lancet*, 376:245-251, 2010.
Bryant et al., "Specific killing of BRCA2-deficient tumours with inhibitors of poly(ADP-ribose) polymerase," *Nature*, 434:913-917, 2005.
Farmer et al., "Targeting the DNA repair defect in BRCA mutant cells as a therapeutic strategy," *Nature*, 434:917-921, 2005.
Fong et al., "Inhibition of poly(ADP-ribose) polymerase in tumors from BRCA mutation carriers," *N Engl J Med.*, 361:123-134, 2009.
Helleday, "Homologous recombination in cancer development treatment and development of drug resistance," *Carcinogenesis*, 31(6):955-960, 2010.
Juvekar et al., "Combining a PI3K inhibitor with a PARP inhibitor provides an effective therapy for BRCA1-related breast cancer," *Cancer Discovery*, 2(11):1048-1063, 2012.
Nowsheen et al., "HER2 overexpression renders human breast cancers sensitive to PARP inhibition independently of any defect in homologous recombination DNA repair," *Cancer Research*, 72(18):4796-4806, 2012.
PCT International Preliminary Report on Patentability issued in International Application No. PCT/US2014/020376, dated Sep. 8, 2015.
PCT International Search Report and Written Opinion issued in International Application No. PCT/US2014/020376, dated Jun. 27, 2014.
Peng et al.,"Exploiting the homologous recombination DNA repair network for targeted cancer therapy," *World Journal of Clinical Oncology*, 2(2):73-79, 2011.
Turner et al., "Biomarkers of PARP inhibitor sensitivity," *Breast Cancer Research and Treatment*, 127(1):283-286, 2011.
Tutt et al., "Oral poly(ADP-ribose) polymerase inhibitor olaparib in patients with BRCA1 or BRCA2 mutations and advanced breast cancer: a proof-of-concept trial," *Lancet*, 376:235-244, 2010.

* cited by examiner

*Primary Examiner* — Craig Ricci
(74) *Attorney, Agent, or Firm* — Parker Highlander PLLC

(57) ABSTRACT

Methods for identifying and treating cancers that are homologous recombination (HR)-repair defective. In some aspects, HR defective cancers are treated with a PARP inhibitor therapy. Methods for sensitizing cancers to a PARP inhibitor therapy are also provided.

8 Claims, 55 Drawing Sheets

CONTACT INHIBITION
|       | CONTROL | LY-294002 | | | RAPAMYCIN | | |
|---|---|---|---|---|---|---|---|
|       |        | 1uM    | 5uM    | 10uM   | 5nM    | 10nM   | 20nM   |
| G1    | 68.215 | 65.804 | 59.693 | 70.917 | 64.94  | 70.338 | 72.599 |
| S     | 27.164 | 30.746 | 40.307 | 26.48  | 32.907 | 27.96  | 24.071 |
| G2/M  | 4.621  | 3.449  | 0      | 2.63   | 2.153  | 1.703  | 3.331  |
FIG. 15A
APHIDICOLIN
|       | CONTROL | LY-294002 | | | RAPAMYCIN | | |
|---|---|---|---|---|---|---|---|
|       |        | 1uM    | 5uM    | 10uM   | 5nM    | 10nM   | 20nM   |
| G1    | 50.17  | 51.26  | 54.21  | 59.86  | 53.03  | 55.56  | 55.64  |
| S     | 44.16  | 44.55  | 42.92  | 37.93  | 45.65  | 43.24  | 41.55  |
| G2/M  | 5.12   | 4.19   | 2.88   | 2.21   | 1.32   | 1.21   | 2.81   |
FIG. 15B
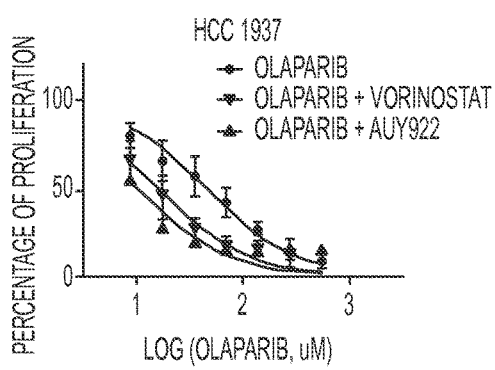
FIG. 15C
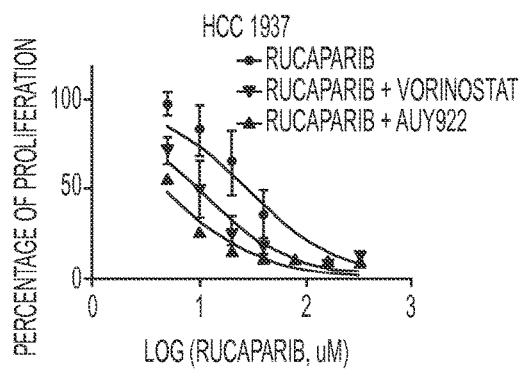
FIG. 15D

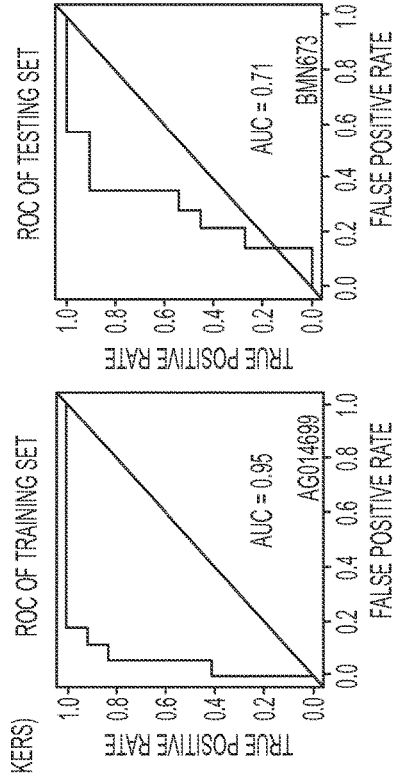
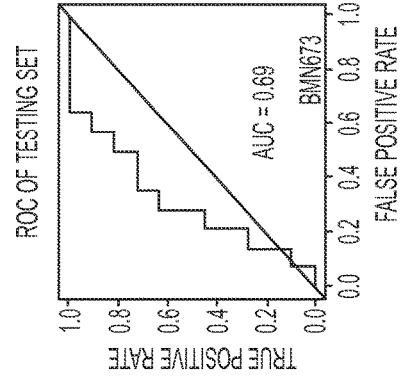
FIG. 21G
FIG. 21H

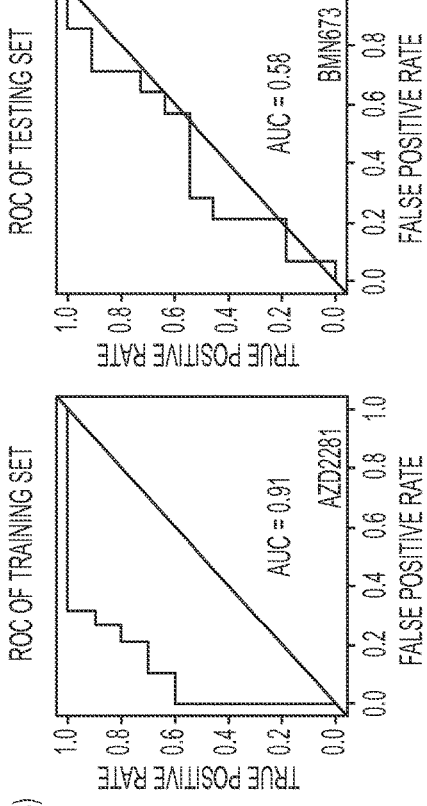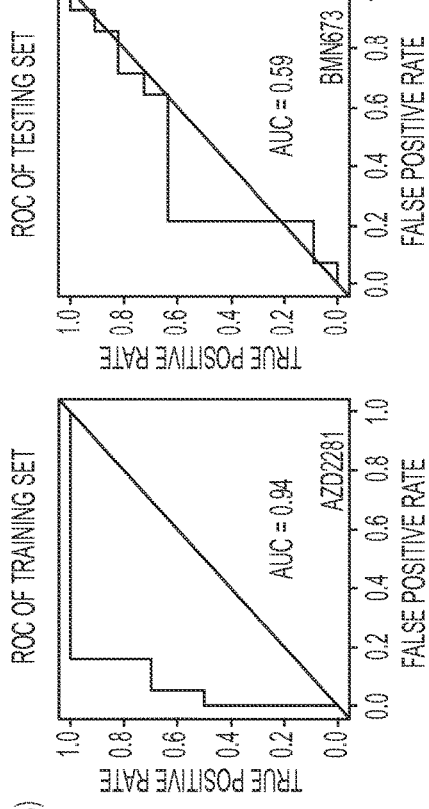
FIG. 22C
FIG. 22D

AZD2281 BREAST MODEL (TOP 9 MARKERS)

| PREDICTOR | WEIGHT |
|---|---|
| (INTERCEPT) | -4.1125514 |
| FOXO3 | 0.7249162 |
| RFC4 | 1.2649443 |
| CSE1L | -0.5665201 |
| FAM43A | -1.4237460 |
| SERTAD4 | 0.4451932 |
| SLC45A3 | 0.4141038 |
| C6orf48 | -0.2073284 |
| HSD11B2 | -0.3229882 |
| C4orf34 | 0.2093716 |

AZD2281 BREAST MODEL (TOP 10 MARKERS)

| PREDICTOR | WEIGHT |
|---|---|
| (INTERCEPT) | -4.51264483 |
| FOXO3 | 0.70139860 |
| RFC4 | 1.34414864 |
| CSE1L | -0.61340082 |
| FAM43A | -1.51300242 |
| SERTAD4 | 0.43730255 |
| SLC45A3 | 0.37055542 |
| C6orf48 | -0.17049368 |
| HSD11B2 | -0.31086783 |
| C4orf34 | 0.22033210 |
| VAMP5 | 0.08796941 |

AG014699 3-DISEASE MODEL (TOP 7 MARKERS)

| PREDICTOR | WEIGHT |
|---|---|
| (INTERCEPT) | 4.12334511 |
| FOXO3 | 0.85327555 |
| HSD11B2 | 0.09653017 |
| SERTAD4 | 0.16536278 |
| CSE1L | -0.79336927 |
| C6orf48 | -0.25130858 |
| C4orf34 | 0.35707638 |
| SLC45A3 | 0.37246309 |

AG014699 3-DISEASE MODEL (TOP 8 MARKERS)

| PREDICTOR | WEIGHT |
|---|---|
| (INTERCEPT) | 4.29559014 |
| FOXO3 | 0.84495192 |
| HSD11B2 | 0.07945300 |
| SERTAD4 | 0.16864018 |
| CSE1L | -0.78625217 |
| C6orf48 | -0.26000487 |
| C4orf34 | 0.36685725 |
| SLC45A3 | 0.40624928 |
| VAMP5 | -0.05029998 |

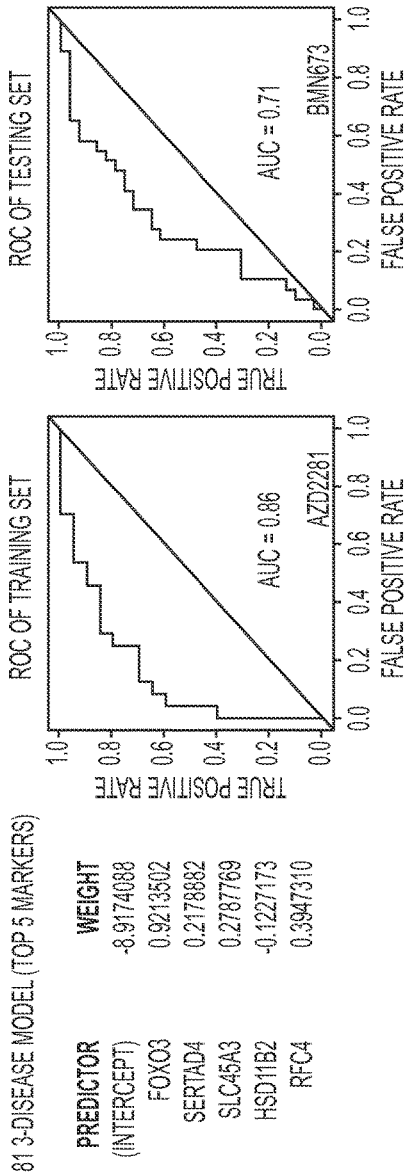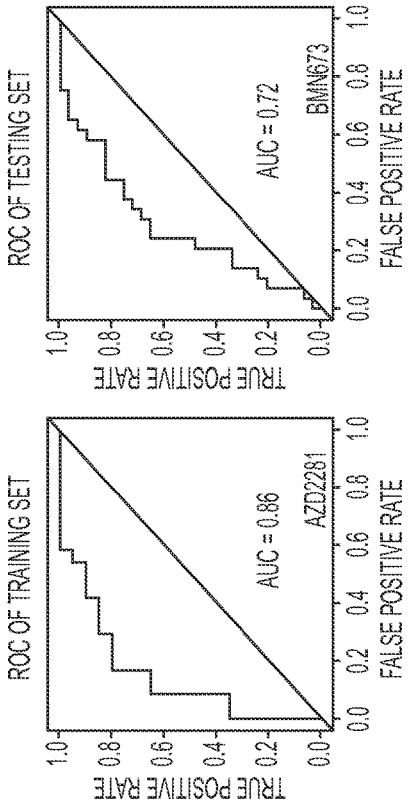
FIG. 25C
FIG. 25D

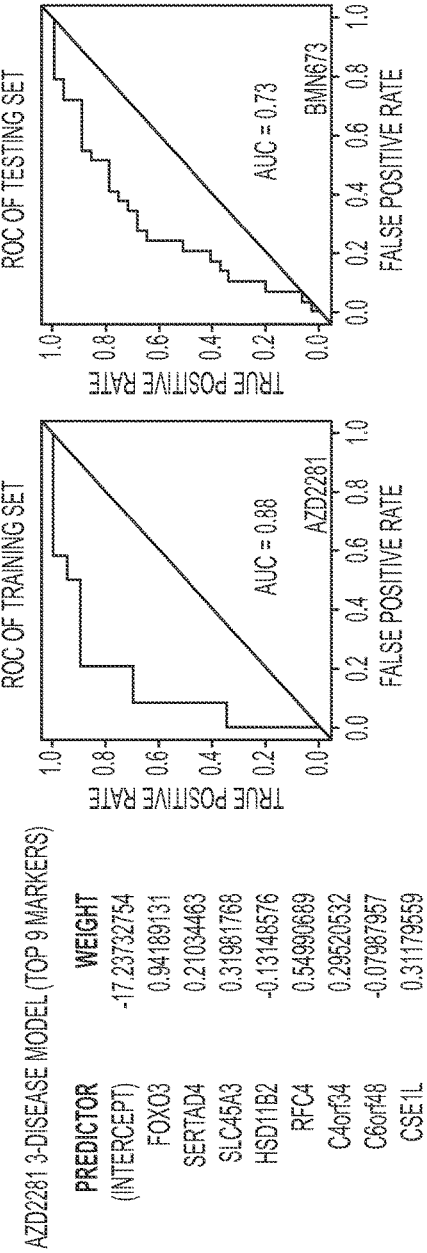
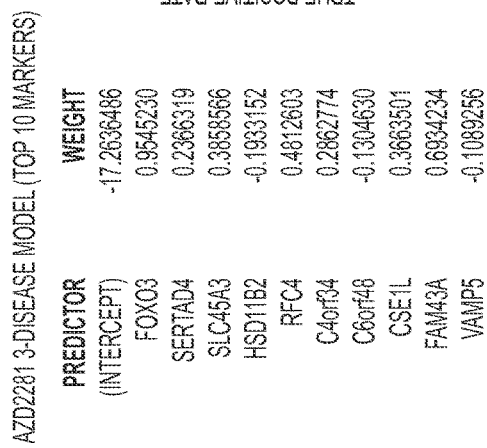
FIG. 25G
FIG. 25H

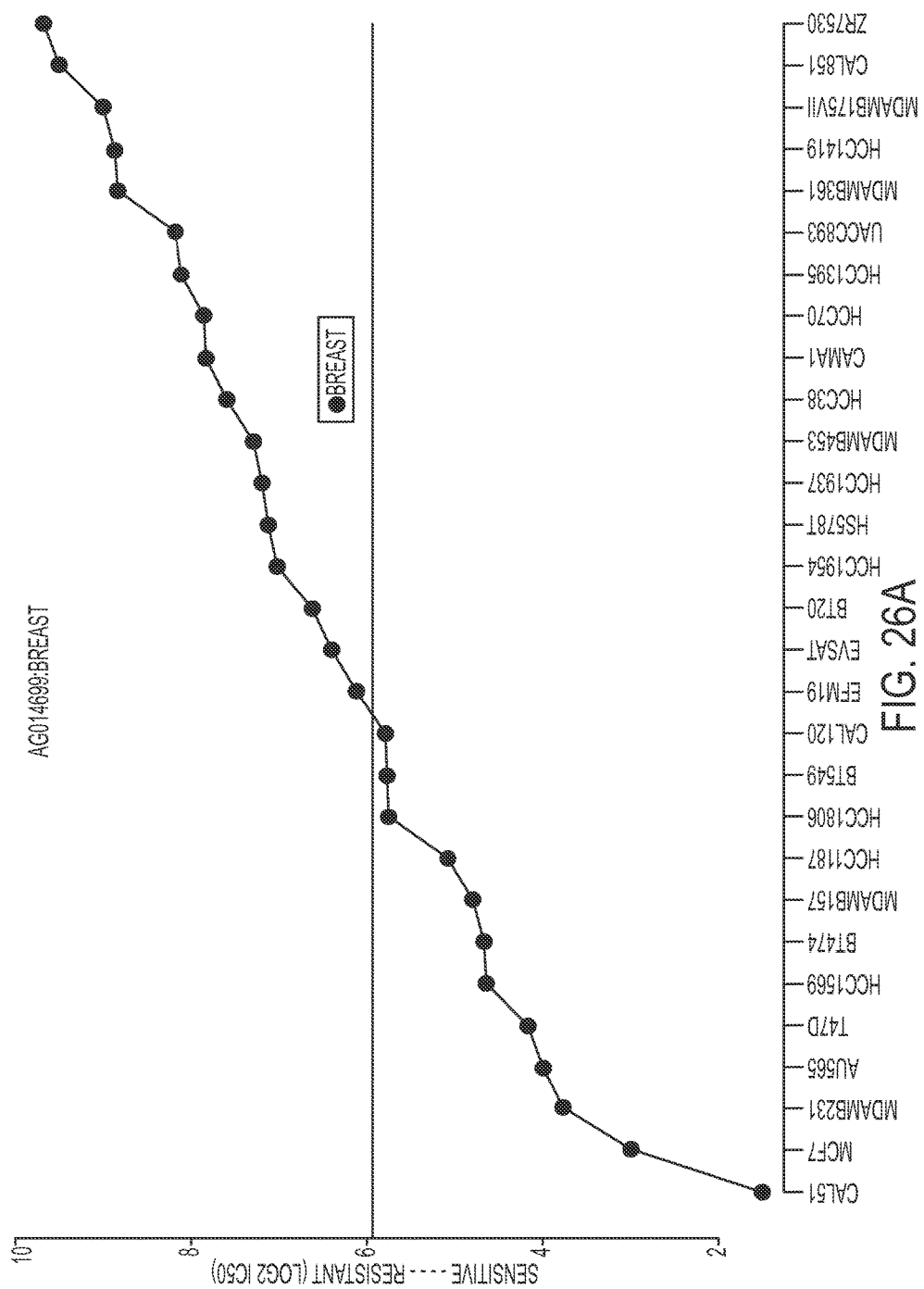

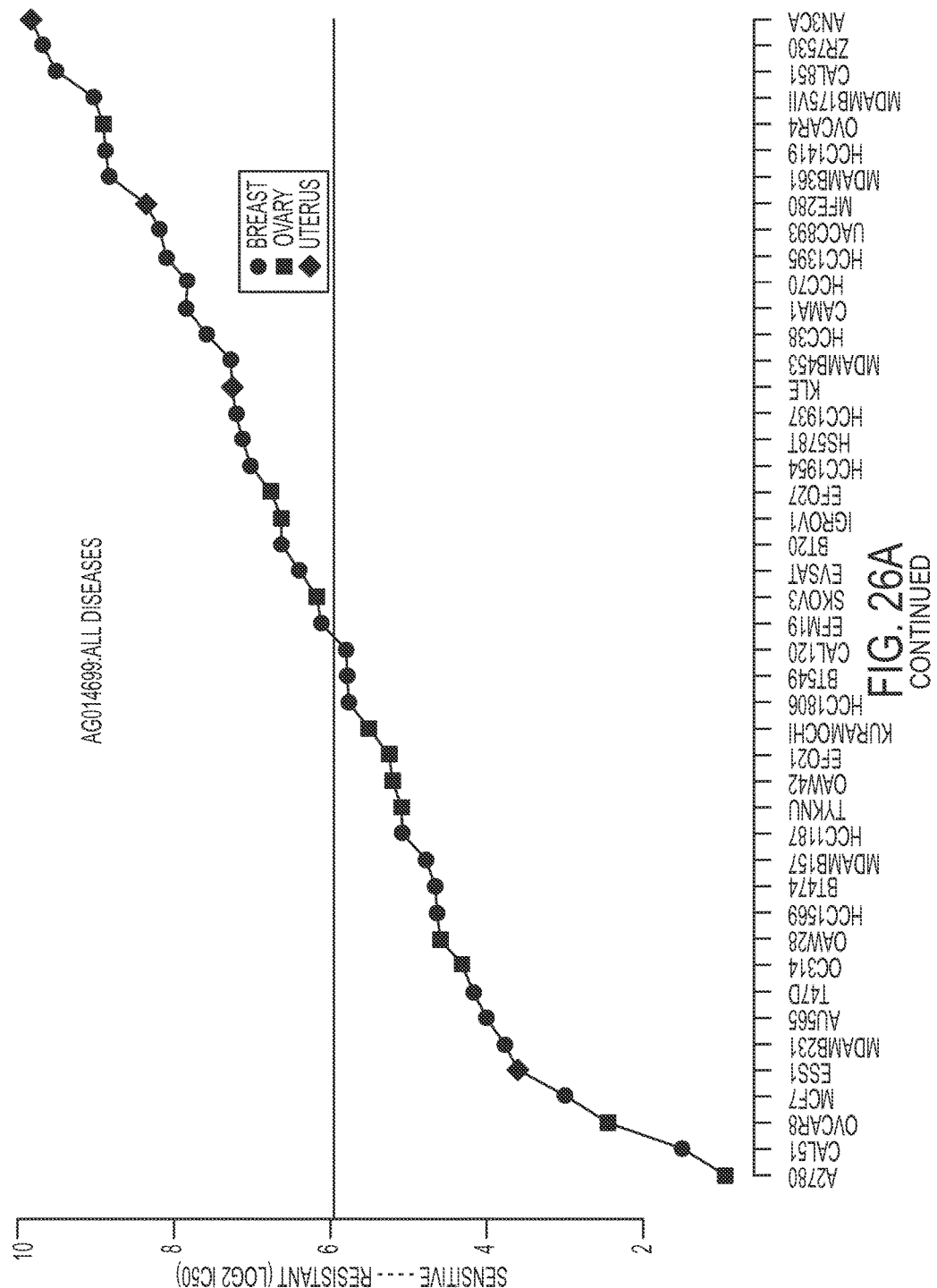

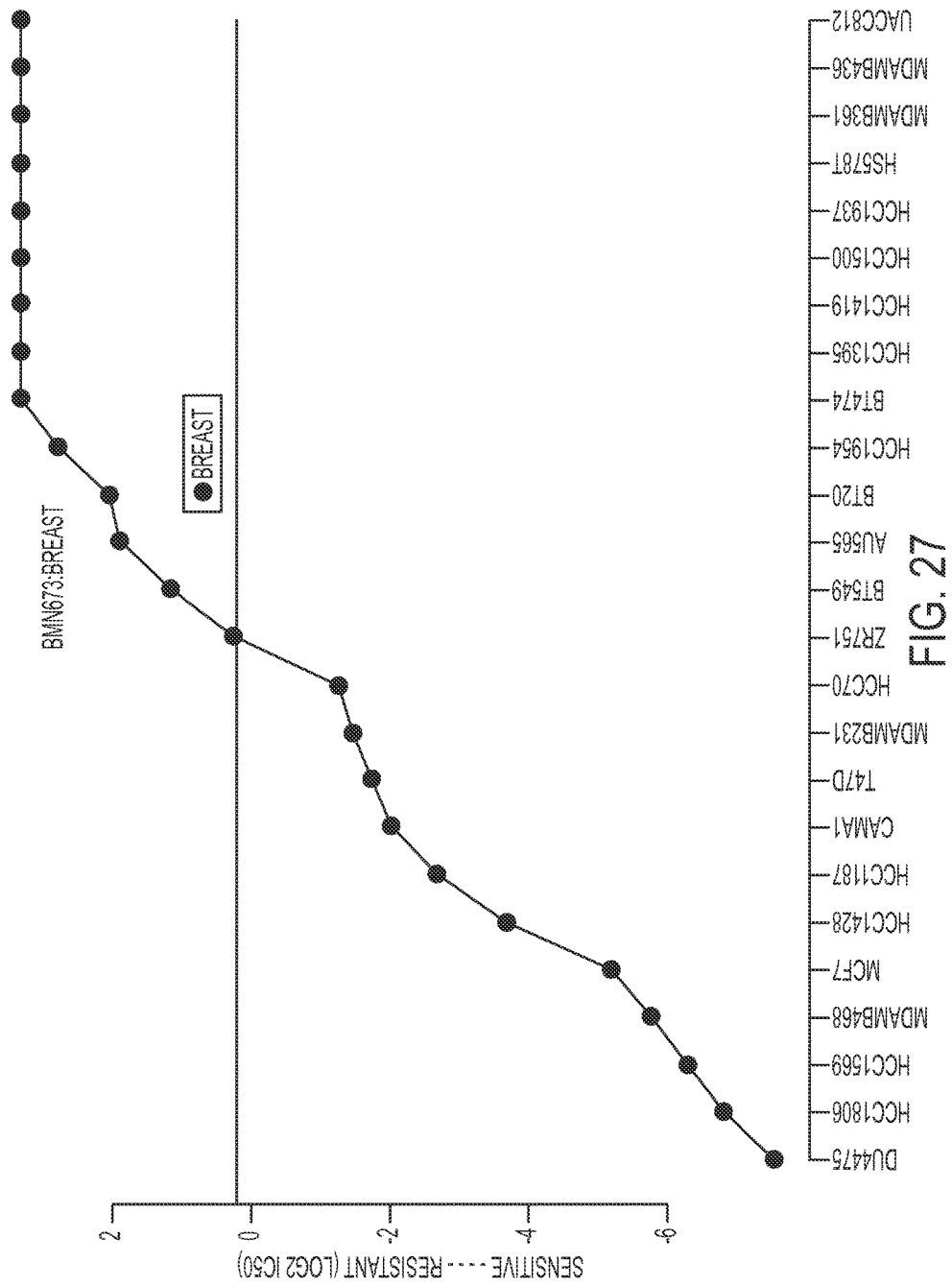

US 9,850,542 B2

SEQUENCE LISTING

```
<160> NUMBER OF SEQ ID NOS: 53

<210> SEQ ID NO 1
<211> LENGTH: 58
<212> TYPE: DNA
<213> ORGANISM: Artificial Sequence
<220> FEATURE:
<223> OTHER INFORMATION: Synthetic nucleic acid

<400> SEQUENCE: 1
ccgggcccac ctaattgtac tgaatctcga gattcagtac aattaggtgg gcttttg      58

<210> SEQ ID NO 2
<211> LENGTH: 58
<212> TYPE: DNA
<213> ORGANISM: Artificial Sequence
<220> FEATURE:
<223> OTHER INFORMATION: Synthetic nucleic acid

<400> SEQUENCE: 2
ccgggcctac aagaaagtac gagatctcga gatctcgtac tttcttgtag gcttttg      58

<210> SEQ ID NO 3
<211> LENGTH: 58
<212> TYPE: DNA
```

<213> ORGANISM: Artificial Sequence
<220> FEATURE:
<223> OTHER INFORMATION: Synthetic nucleic acid

<400> SEQUENCE: 3
ccgggccatg tgttgtggtt cttaactcga gttaagaacc acaacacatg gcttttttg    58

<210> SEQ ID NO 4
<211> LENGTH: 58
<212> TYPE: DNA
<213> ORGANISM: Artificial Sequence
<220> FEATURE:
<223> OTHER INFORMATION: Synthetic nucleic acid

<400> SEQUENCE: 4
ccgggcaatg gagaagagat tacaactcga gttgtaatct cttctccatt gcttttttg    58

<210> SEQ ID NO 5
<211> LENGTH: 57
<212> TYPE: DNA
<213> ORGANISM: Artificial Sequence
<220> FEATURE:
<223> OTHER INFORMATION: Synthetic nucleic acid

<400> SEQUENCE: 5
ccgggctgaa gctatgttcg ccattctcga gaatggcgaa catagcttca gcttttt      57

<210> SEQ ID NO 6
<211> LENGTH: 57
<212> TYPE: DNA
<213> ORGANISM: Artificial Sequence
<220> FEATURE:
<223> OTHER INFORMATION: Synthetic nucleic acid

<400> SEQUENCE: 6
ccggcggtca gagatcatac agattctcga gaatctgtat gatctctgac cgttttt      57

<210> SEQ ID NO 7
<211> LENGTH: 57
<212> TYPE: DNA
<213> ORGANISM: Artificial Sequence
<220> FEATURE:
<223> OTHER INFORMATION: Synthetic nucleic acid

<400> SEQUENCE: 7
ccggaggcgc tatgtgtatt attatctcga gataataata cacatagcgc ctttttt      57

<210> SEQ ID NO 8
<211> LENGTH: 57
<212> TYPE: DNA
<213> ORGANISM: Artificial Sequence
<220> FEATURE:
<223> OTHER INFORMATION: Synthetic nucleic acid

<400> SEQUENCE: 8
ccggccacag ctagaactta tcaaactcga gtttgataag ttctagctgt ggttttt      57

<210> SEQ ID NO 9
<211> LENGTH: 58
<212> TYPE: DNA
<213> ORGANISM: Artificial Sequence
<220> FEATURE:
<223> OTHER INFORMATION: Synthetic nucleic acid

<400> SEQUENCE: 9
ccggtgatgg tcttaaggaa catctctcga gagatgttcc ttaagaccat cattttttg    58

<210> SEQ ID NO 10
<211> LENGTH: 58
<212> TYPE: DNA
<213> ORGANISM: Artificial Sequence
<220> FEATURE:
<223> OTHER INFORMATION: Synthetic nucleic acid

<400> SEQUENCE: 10
ccgggcctcc aattcttcac agtaactcga gttactgtga agaattggag gctttttg        58

<210> SEQ ID NO 11
<211> LENGTH: 58
<212> TYPE: DNA
<213> ORGANISM: Artificial Sequence
<220> FEATURE:
<223> OTHER INFORMATION: Synthetic nucleic acid

<400> SEQUENCE: 11
ccggaatgca tttggtatga atctgctcga gcagattcat accaaatgca ttttttg        58

<210> SEQ ID NO 12
<211> LENGTH: 58
<212> TYPE: DNA
<213> ORGANISM: Artificial Sequence
<220> FEATURE:
<223> OTHER INFORMATION: Synthetic nucleic acid

<400> SEQUENCE: 12
ccggctgtgg ttgtatctgt tcaatctcga gattgaacag atacaaccac agtttttg        58

<210> SEQ ID NO 13
<211> LENGTH: 57
<212> TYPE: DNA
<213> ORGANISM: Artificial Sequence
<220> FEATURE:
<223> OTHER INFORMATION: Synthetic nucleic acid

<400> SEQUENCE: 13
ccgggtggtt tatctgcatg gtattctcga gaataccatg cagataaacc actttt        57

<210> SEQ ID NO 14
<211> LENGTH: 57
<212> TYPE: DNA
<213> ORGANISM: Artificial Sequence
<220> FEATURE:
<223> OTHER INFORMATION: Synthetic nucleic acid

<400> SEQUENCE: 14
ccgggtaaac agtgcttcta gtgaactcga gttcactaga agcactgttt acttttt        57

<210> SEQ ID NO 15
<211> LENGTH: 57
<212> TYPE: DNA
<213> ORGANISM: Artificial Sequence
<220> FEATURE:
<223> OTHER INFORMATION: Synthetic nucleic acid

<400> SEQUENCE: 15
ccgggaacag ataaataccg aacatctcga gatgttcggt atttatctgt tctttt        57

<210> SEQ ID NO 16
<211> LENGTH: 57
<212> TYPE: DNA
<213> ORGANISM: Artificial Sequence
<220> FEATURE:

```
<223> OTHER INFORMATION: Synthetic nucleic acid

<400> SEQUENCE: 16
ccggacgatg ccaaactcca gccagctcga gctggctgga gtttggcatc gtttttt          57

<210> SEQ ID NO 17
<211> LENGTH: 57
<212> TYPE: DNA
<213> ORGANISM: Artificial Sequence
<220> FEATURE:
<223> OTHER INFORMATION: Synthetic nucleic acid

<400> SEQUENCE: 17
ccgggatact tggtcttact ggtttctcga gaaaccagta agaccaagta tctttttt          57

<210> SEQ ID NO 18
<211> LENGTH: 57
<212> TYPE: DNA
<213> ORGANISM: Artificial Sequence
<220> FEATURE:
<223> OTHER INFORMATION: Synthetic nucleic acid

<400> SEQUENCE: 18
ccggccagtg tgattagtat tgattctcga gaatcaatac taatcacact ggttttt          57

<210> SEQ ID NO 19
<211> LENGTH: 58
<212> TYPE: DNA
<213> ORGANISM: Artificial Sequence
<220> FEATURE:
<223> OTHER INFORMATION: Synthetic nucleic acid

<400> SEQUENCE: 19
ccgggccttg aataatcaca ggcaactcga gttgcctgtg attattcaag ctttttg          58

<210> SEQ ID NO 20
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 20
gcaaagcccu aguaacaua                                                    19

<210> SEQ ID NO 21
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 21
ggugugaucu ucaguauau                                                    19

<210> SEQ ID NO 22
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 22
gagaggagac agcuuguua                                                    19
```

```
<210> SEQ ID NO 23
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 23
gaugggaggc cuaggauuu                                                    19

<210> SEQ ID NO 24
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 24
gagaaaggau uguagacua                                                    19

<210> SEQ ID NO 25
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 25
gcaacucgcc uaacagaua                                                    19

<210> SEQ ID NO 26
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 26
ccacgaaugu uaacucuau                                                    19

<210> SEQ ID NO 27
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 27
ccgcuaaucu ucuaacauu                                                    19

<210> SEQ ID NO 28
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 28
caagaugugu gguacuuua                                                    19

<210> SEQ ID NO 29
<211> LENGTH: 19
<212> TYPE: RNA
<213> ORGANISM: Artificial Sequence
<220> FEATURE:
<223> OTHER INFORMATION: Synthetic nucleic acid
```

```
<400> SEQUENCE: 29
gagaaggcaa uauccaaua                                              19

<210> SEQ ID NO 30
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 30
ccacaugucc ugaucauau                                              19

<210> SEQ ID NO 31
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 31
gaaguugggc uaucaaugg                                              19

<210> SEQ ID NO 32
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 32
guaagaaagu agccauaaa                                              19

<210> SEQ ID NO 33
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 33
gcauaggacu caaguguca                                              19

<210> SEQ ID NO 34
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 34
guugugaacu ccgugguuu                                              19

<210> SEQ ID NO 35
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 35
cucaggaacu cuauucuau                                              19

<210> SEQ ID NO 36
<211> LENGTH: 19
```

```
<212> TYPE: RNA
<213> ORGANISM: Artificial Sequence
<220> FEATURE:
<223> OTHER INFORMATION: Synthetic nucleic acid

<400> SEQUENCE: 36
ggacuccagu guugcauu                                                    19

<210> SEQ ID NO 37
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 37
gagcugggaa guauaaauu                                                   19

<210> SEQ ID NO 38
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 38
gcuauauccu ugaagauuu                                                   19

<210> SEQ ID NO 39
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 39
gaaggacgga guacuaaua                                                   19

<210> SEQ ID NO 40
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 40
gauaagauca uccgacuuu                                                   19

<210> SEQ ID NO 41
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 41
gcaauaccuu ggaugauua                                                   19

<210> SEQ ID NO 42
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 42
```
ccaguuaacc uucuaaaua                                                19

<210> SEQ ID NO 43
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 43
gauaguugau ggaaugcua                                                19

<210> SEQ ID NO 44
<211> LENGTH: 21
<212> TYPE: RNA
<213> ORGANISM: Artificial Sequence
<220> FEATURE:
<223> OTHER INFORMATION: Synthetic nucleic acid

<400> SEQUENCE: 44
gugccagcga cuugcgcaau u                                             21

<210> SEQ ID NO 45
<211> LENGTH: 21
<212> TYPE: RNA
<213> ORGANISM: Artificial Sequence
<220> FEATURE:
<223> OTHER INFORMATION: Synthetic nucleic acid

<400> SEQUENCE: 45
aagccauacc acugcgagau u                                             21

<210> SEQ ID NO 46
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 46
gauaagauca uccgacuuu                                                19

<210> SEQ ID NO 47
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 47
gcaauaccuu ggaugauua                                                19

<210> SEQ ID NO 48
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 48
ccaguuaacc uucuaaaua                                                19

<210> SEQ ID NO 49
<211> LENGTH: 19
<212> TYPE: RNA
<213> ORGANISM: Artificial Sequence

```
<220> FEATURE:
<223> OTHER INFORMATION: Synthetic nucleic acid

<400> SEQUENCE: 49
gauaguugau ggaaugcua                                                   19

<210> SEQ ID NO 50
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 50
caacaugccc acagaucaa                                                   19

<210> SEQ ID NO 51
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 51
ccaaagcgag caagagaau                                                   19

<210> SEQ ID NO 52
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 52
ugauaaagcu ccagcagga                                                   19

<210> SEQ ID NO 53
<211> LENGTH: 19
<212> TYPE: RNA
<213> ORGANISM: Artificial Sequence
<220> FEATURE:
<223> OTHER INFORMATION: Synthetic nucleic acid

<400> SEQUENCE: 53
gaaggagcuu ucaucauuc                                                   19
```

GENE SIGNATURE TO PREDICT HOMOLOGOUS RECOMBINATION (HR) DEFICIENT CANCER

The present application is a national phase application under 35 U.S.C. §371 of International Application No. PCT/US2014/020376, filed Mar. 4, 2014, which claims the priority benefit of U.S. provisional application No. 61/772,406, filed Mar. 4, 2013, the entire contents of each of which are incorporated herein by reference.

The invention was made with government support under Grant Nos. R01 CA112291, K99 CA149186, and CA016672 awarded by the National Institutes of Health and Grant No. W81XWH-10-1-0558 awarded by the Department of Defense. The government has certain rights in the invention.

The sequence listing that is contained in the file named "UTFC1215WO_ST25.txt", which is 11 KB (as measured in Microsoft Windows) and was created on Mar. 3, 2014, is filed herewith by electronic submission and is incorporated by reference herein.

BACKGROUND OF THE INVENTION

1. Field of the Invention

The present invention relates generally to the field of molecular biology and oncology. More particularly, it concerns methods for identifying and treating homologous recombination (HR) repair defective cancers.

2. Description of Related Art

Genomic instability is a hallmark of cancer cells (Hanahan and Weinberg, 2011). To maintain genomic stability and ensure high-fidelity transmission of genetic information, cells have evolved a complex mechanism to repair DNA double-strand breaks (DSBs), the most deleterious DNA lesions, in an error-free manner through homologous recombination (HR) (Moynahan and Jasin, 2010; San Filippo et al., 2008). As expected, HR-mediated DNA repair deficiency predisposes to cancer development (Levitt and Hickson, 2002). For instance, germline mutations in the tumor suppressors BRCA1 and BRCA2, two critical HR repair mediators, predispose to both breast and ovarian cancer (Jackson and Bartek, 2009; Scully and Livingston, 2000). However, HR-mediated DNA repair deficiency also sensitizes cancer cells to DNA-damage-inducing therapy such as radiation therapy and DNA-damage-based chemotherapy (Lord and Ashworth, 2012).

HRD also sensitizes cancer cells to DNA-damage-inducing therapy such as radiation therapy and cisplatin-based chemotherapy (Helleday et al., 2008; Lord and Ashworth, 2012). One of the most exciting recent therapeutic breakthroughs in cancer is identification of a synthetic lethal interaction between HR repair deficiency and poly(ADP-ribose) polymerase (PARP) inhibition (Bryant et al., 2005; Farmer et al., 2005). PARP inhibitors inhibit single-strand DNA repair, which leads to DSBs when DNA replication occurs. Normal cells can repair these DSBs. However, HR repair-deficient cancer cells cannot repair PARP-inhibitor-induced DSBs and die when treated with these drugs. Thus, PARP inhibitors can selectively target HR repair-deficient breast and ovarian cancer (Rehman et al., 2010). This concept holds great promise for effective treatment of BRCA1/2-associated breast and ovarian cancer and more broadly for all HR-repair-deficient tumors, particularly if practical and effective companion diagnostics able to robustly identify patients likely to benefit can be identified.

However, recent clinical trials of PARP inhibitors have shown disappointing results: For example, in the first phase I clinical trial of monotherapy with the oral PARP inhibitor olaparib, more than 35% of BRCA mutation carriers did not respond (Fong et al., 2009). In a phase II clinical study of olaparib in breast cancer patients with BRCA1/2 mutations, the response rate was 41%. Unfortunately, the progression-free survival times in the two cohorts were approximately 3.8 months and 5.7 months, suggesting that patients rapidly developed resistance (Tutt et al., 2010). In a similar phase II study in BRCA1/2 mutation carriers with recurrent ovarian cancer, the objective response rate was 33% (Audeh et al., 2010). Furthermore, there were no complete or partial responses to olaparib in 15 BRCA-negative patients with advanced-stage triple-negative breast cancer (TNBC), which has a molecular phenotype similar to that of BRCA1-deficient breast cancer (Gelmon et al., 2011). Thus only a portion of patients with BRCA1/2 aberrations respond and unfortunately responses are frequently short-lived. Thus a better approach able to predict patients likely to benefit or rational combination therapies with PARP inhibitors designed to prevent the emergence of resistance are needed to fulfill the promise of PARP inhibitors.

SUMMARY OF THE INVENTION

In a first embodiment, the present invention provides a method of identifying a cancer as homologous recombination (HR) repair defective comprising obtaining a sample of the cancer; assaying the expression levels of at least 3 of the genes selected from the group consisting of FOXO3, VAMP5, CSE1L, SLC45A3, HSD11B2, RFC4, C6orf48, FAM43A, SERTAD4, C4orf34 and those listed in Table 2 in the sample; and identifying the cancer as HR defective if the expression level of said genes are up- or down-regulated compared to a control expression level; or identifying the cancer not HR defective if said genes are not up- or down-regulated compared to a control expression level. In certain aspects, the method may be defined as an in vitro method.

In one aspect, a cancer may be identified as HR defective if at least one gene from Table 2A is down regulated relative to a control expression level. Alternatively, the cancer may not be identified as HR defective if the gene is not down regulated relative to a control expression level. Conversely, in another aspect, a cancer may be identified as HR defective if at least one gene from Table 2B is up-regulated relative to a control expression level. In one aspect, the gene from Table 2B may be FOXO3. Alternatively, the cancer may not be identified as HR defective if the gene is not up-regulated relative to a control expression level.

In certain aspects, the method may comprise assaying the expression levels of at least 4, 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229 or 230 of the genes listed in Table 2. In certain aspects, the method may comprise assaying the expression levels of 10-50, 20-100, 50-150, or 100-230 of the genes listed in Table 2, or any range derivable therein. In another aspect, the method may comprise assaying the expression levels of all 230 genes listed in Table 2. In a further aspect, the assayed gene expression levels may comprise BLM, DNA2, and EXO1 expression levels. In one aspect, the assayed gene expression levels may comprise assaying the expression levels of at least 3 of the genes selected from the group consisting of FOXO3, VAMP5, CSE1L, SLC45A3, HSD11B2, RFC4, C6orf48, FAM43A, SERTAD4, and C4orf34 expression levels.

In a further aspect, a method of the embodiments may be defined as a method of determining a prognosis of a cancer. Thus, in some aspects, identifying a cancer as HR defective is indicative of better overall survival. In another aspect, identifying a cancer as HR defective further comprises identifying a patient having the cancer as a candidate for PARP inhibitor (PARPi) therapy. In another aspect, identifying a cancer as HR defective further comprises identifying a patient having the cancer as a candidate for therapy with particular DNA damaging agents (e.g., platin derivatives or radiation).

In certain aspects, assaying the expression levels may comprise preforming RT-PCR, a hybridization, transcriptome analysis, RNAseq, a Northern blot, a Western blot, or an ELISA. For example, assaying the expression levels can comprise performing an array hybridization. In one aspect, transcriptome analysis may comprise obtaining sequence information of expressed RNA molecules.

In a further embodiment, the present invention provides a method of treating a cancer patient comprising (a) selecting a patient determined to have a homologous recombination repair (HR) defective cancer based on the expression levels in a sample of the cancer of at least 3 genes listed in Table 2; and (b) treating the selected patient with a PARP inhibitor (PARPi) or a platin analog therapy. In certain aspects, the method may further comprise administering a second anti-cancer therapy to the subject in conjunction with the PARP inhibitor (PARPi) or a platin analog therapy. The second anti-cancer therapy may comprise a TTK inhibitor, mTOR inhibitor, or a PI3K inhibitor.

In certain aspects of the present methods, the cancer may be a renal cancer, a lung cancer, an ovarian cancer, or a breast cancer. In some aspects, the cancer is a BRCA mutant cancer regardless of tissue of origin.

In one embodiment, the present invention provides a composition comprising a PARP inhibitor or platin analog for use in treating a cancer patient determined to have a homologous recombination (HR) repair defective cancer. In certain aspects of the present methods, the cancer may be a renal cancer, a lung cancer, an ovarian cancer, or a breast cancer. In some aspects, the cancer is a BRCA mutant cancer regardless of tissue of origin. In certain aspects, the method may further comprise administering a second anti-cancer therapy to the subject in conjunction with the PARP inhibitor or a platin analog therapy. The second anti-cancer therapy may comprise a TTK inhibitor, mTOR inhibitor, or a PI3K inhibitor. In some aspects, an mTOR inhibitor may be an allosteric or catalytic inhibitor. In various aspects, an mTOR inhibitor may be rapamycin or a rapamycin analog (e.g., sirolimus), a PI3K inhibitor may be BEZ 235, BYL 719, BKM 120, or GDC-0941, a TTK inhibitor may be MPI-0479605 or AZ3146, and a PARP inhibitor or PARP inhibitor-based anticancer therapy may comprise olaparib, ABT-888 (Veliparib), BMN 673, Iniparib (BSI-201), Rucaparib (AG-014699, PF-01367338), AG14361, INO-1001, A-966492, PJ34, or MK-4827.

In one embodiment, the present invention provides a composition comprising a TTK, mTOR, or PI3K inhibitor and a PARP inhibitor for use in treating a cancer in a patient. In some aspects, an mTOR inhibitor may be an allosteric or catalytic inhibitor. In various aspects, an mTOR inhibitor may be rapamycin or a rapamycin analog (e.g., sirolimus), a PI3K inhibitor may be BEZ 235, BYL 719, BKM 120, or GDC-0941, a TTK inhibitor may be MPI-0479605 or AZ3146, and a PARP inhibitor or PARP inhibitor-based anticancer therapy may comprise olaparib, ABT-888 (Veliparib), BMN 673, Iniparib (BSI-201), Rucaparib (AG-014699, PF-01367338), AG14361, INO-1001, A-966492, PJ34, or MK-4827.

In still a further embodiment, the present invention provides a method of sensitizing a cancer to a PARP inhibitor-based anticancer therapy comprising administering an effective amount of a TTK, mTOR or PI3K inhibitor to a patent having the cancer. The method may further comprise administering a PARP inhibitor-based anticancer therapy to the subject. In another aspect, the PARP inhibitor-based anticancer therapy may be administered essentially simultaneously with said TTK, mTOR or PI3K inhibitor.

In yet a further embodiment, a composition is provided for use in treating a patient have a cancer, the composition comprising a PARP inhibitor and a TTK, mTOR or PI3K inhibitor.

In aspects of the various embodiments of the present invention, an mTOR inhibitor may be rapamycin or a rapamycin analog (e.g., sirolimus), a PI3K inhibitor may be BEZ 235, BYL 719, BKM 120, or GDC-0941, a TTK inhibitor may be MPI-0479605 or AZ3146, and a PARP inhibitor or PARP inhibitor-based anticancer therapy may comprise olaparib, ABT-888 (Veliparib), BMN 673, Iniparib (BSI-201), Rucaparib (AG-014699, PF-01367338), AG14361, INO-1001, A-966492, PJ34, or MK-4827.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Results are show as mean±SD from three independent experiments; Student's t-test was used to test statistical significance. (C) Whole cell lysate was analyzed by western blotting via indicated antibodies, demonstrating effective knockdown by shRNA (target sequences in Table 15). Flow cytometry analyses of cell cycle distribution in these cell lines are shown next to Western blots.

Figure 7A:
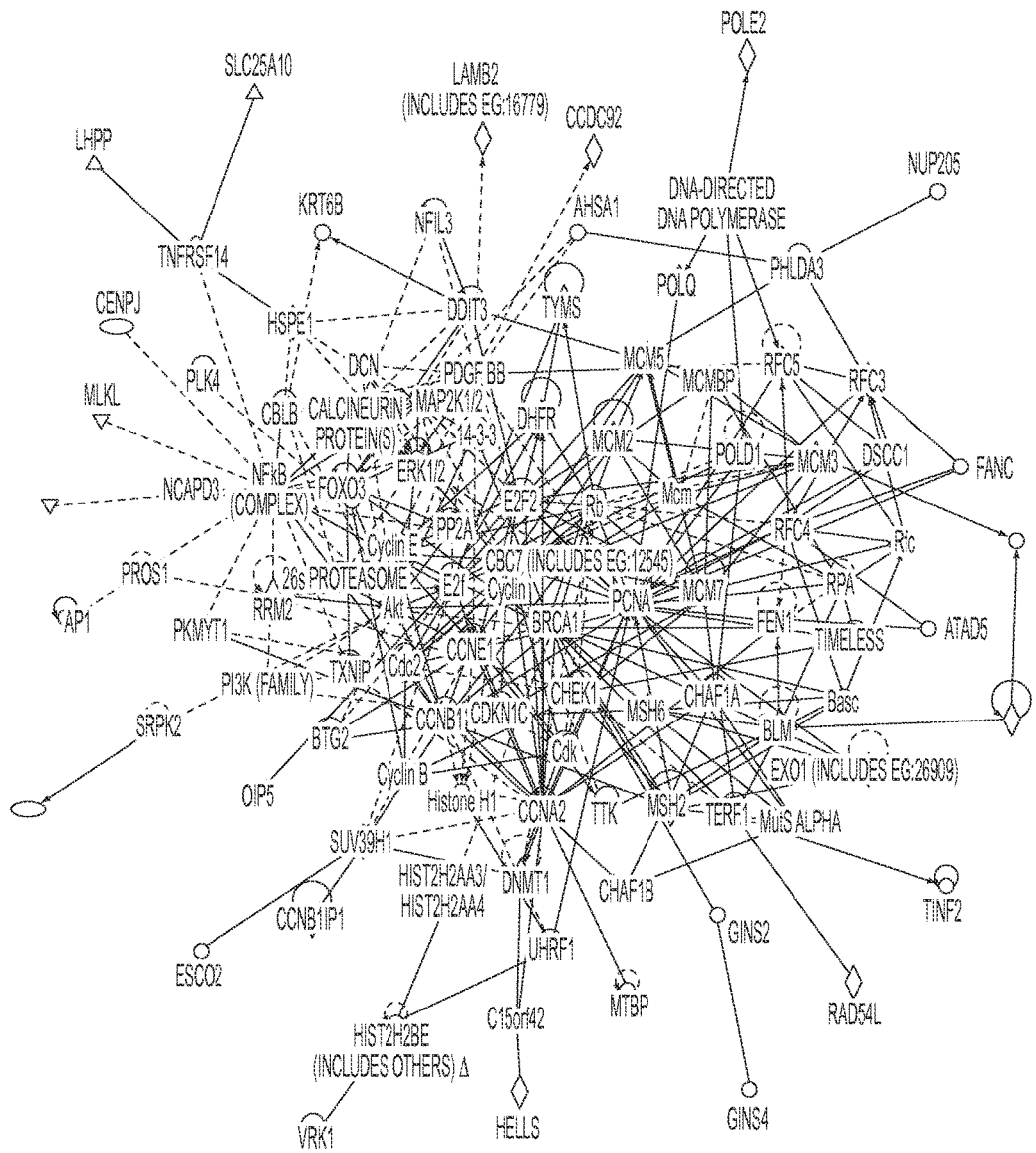
Figure 7B:
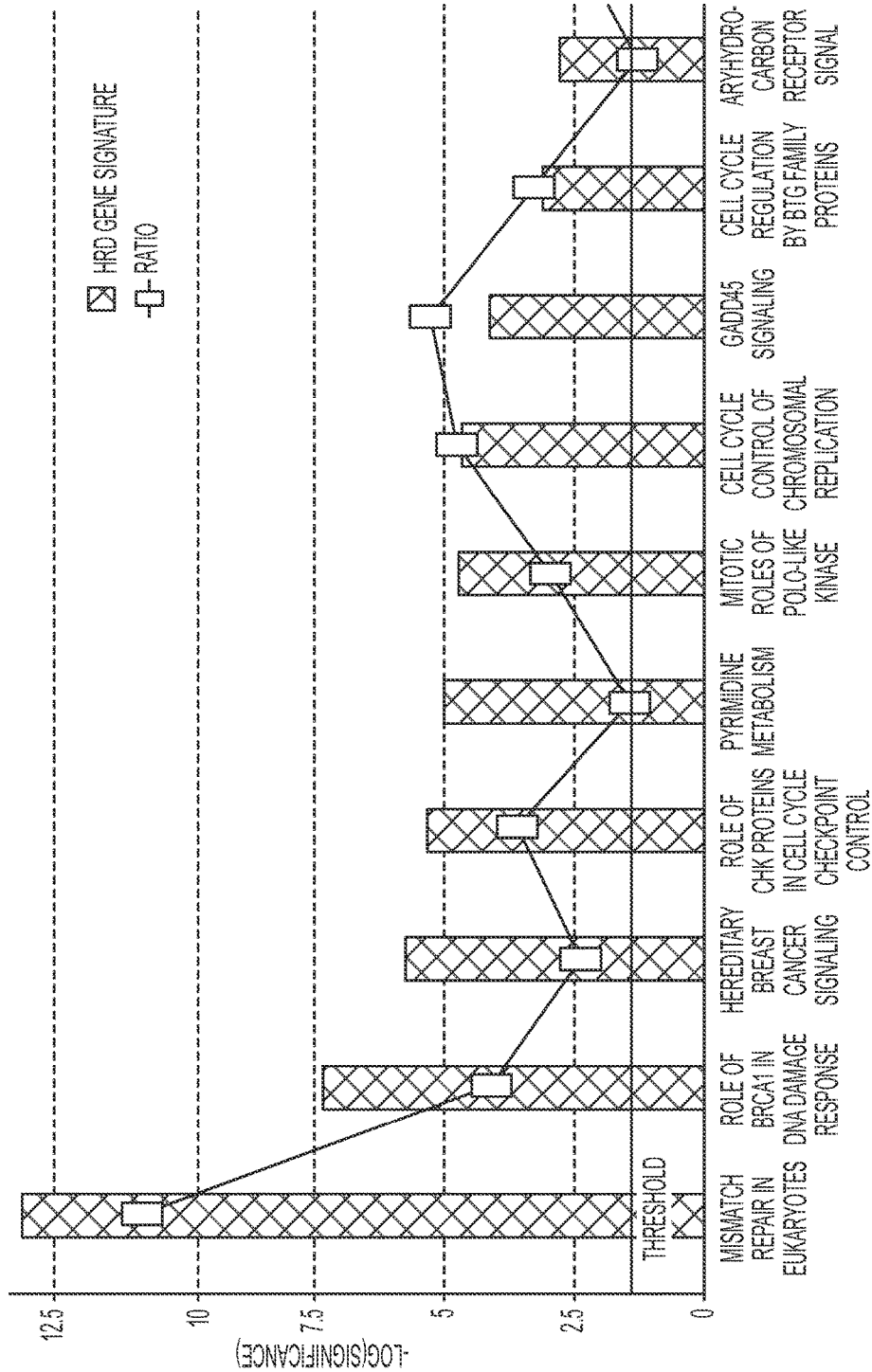

FIGS. 7A-B. Genes in the HRD gene signature are involved in various cellular processes. (A) The networks with the largest numbers of genes in the HRD gene signature on analysis with Ingenuity Systems' IPA software were cell cycle; DNA replication, recombination, and repair; and cellular assembly and organization. Nodes are up-regulated or down-regulated as indicated in Table 2. (B) Top ten canonical pathways in terms of number of genes in the HRD gene signature on analysis with Ingenuity Systems' IPA software. Significance refers to the −log (p value), which is obtained by the Ingenuity program using Fisher's exact test. Threshold is at P=0.05.

Figure 8:
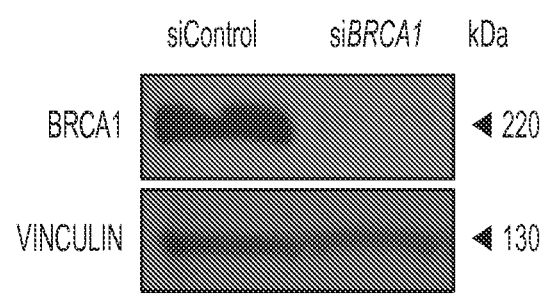

FIG. 8. Western blot analyses demonstrating effective transient siRNA knockdown of BRCA1.

Figure 9A:
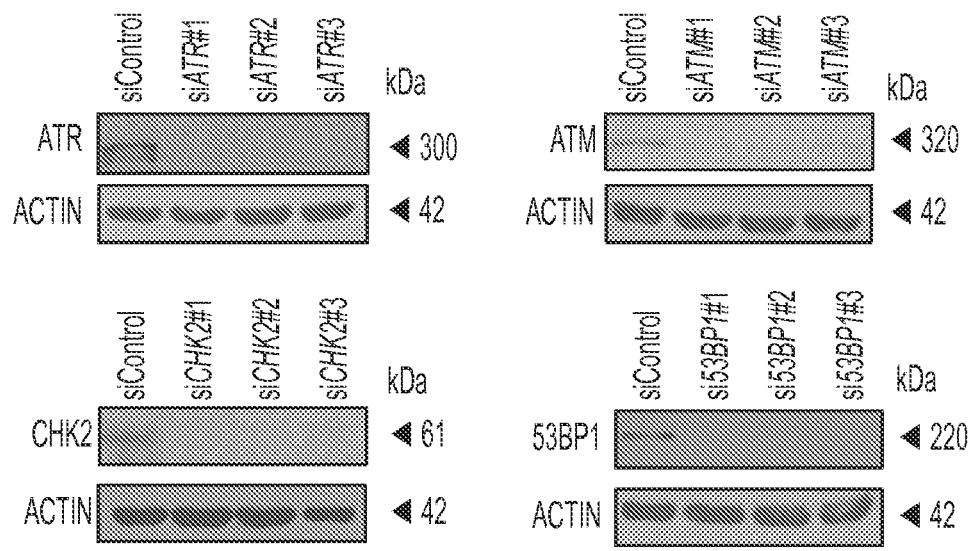
Figure 9B:
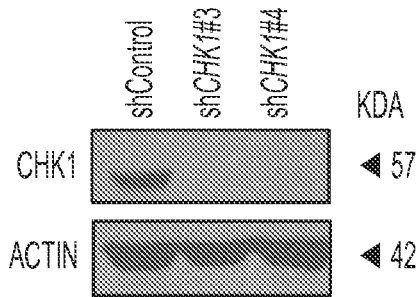

FIGS. 9A-B. The HRD gene signature predicts HRD induced by knockdown of different HR-related genes. Western blot analyses demonstrated effective knockdown. (A) MCF10A cells were transfected with SMARTpool siRNAs targeting ATM, ATR, CHK2 or 53BP1. Effective knockdowns are shown by indicated antibodies. (B) U2OS cells were transfected with SMARTpool siRNAs targeting CHK1. Representative western blot is shown for effective knockdown. Cells lysates were harvested from three independent experiments to have biological triplicates for microarray analysis.

FIGS. 10A-D. Depletion of ZNF668 significantly reduces RAD51 foci formation, but does not affect cell cycle distribution. (A) MDA-MB-436 cells were transfected with control or ZNF668 siRNA. Left: Effective knockdown are shown. Right: Cell cycle analysis seventy-two hours after transfection. (B) RAD51 foci formation in MDA-MB-436 cells transfected with control or ZNF668 siRNA. Irradiated and nonirradiated cultures were stained with an anti-RAD51 pAb and foci were visualized by microscopy. Top: representative immunostaining images. Bottom: the bar graph is shown as the mean±SEM; Student's t-test. At least 50 cells were scored in each sample from three independent replications. Scale bar is 10 μm. (C) EVSAT cells were transfected with Flag-vector or Flag-ZNF668. Left: Effective knockdown are shown. Right: Cell cycle analysis seventy-two hours after transfection. (D) RAD51 foci formation in EVSAT cells transfected with Flag-vector or Flag-ZNF668. Irradiated and nonirradiated cultures were stained with an anti-RAD51 pAb and foci were visualized by microscopy. Top: representative immunostaining images. Bottom: the bar graph is shown as the mean±SEM; Student's t-test. At least 50 cells were scored in each sample from three independent replications. Scale bar is 10 μm.

Figure 11A:
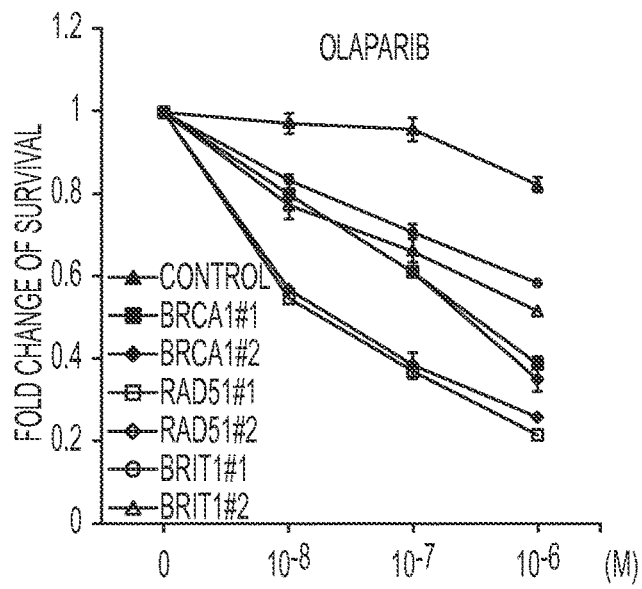
Figure 11B:
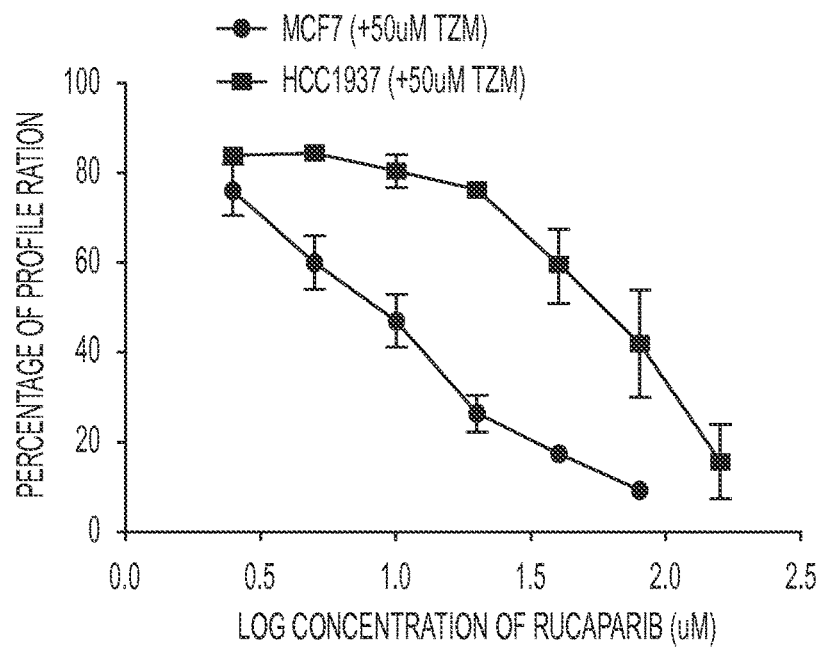

FIGS. 11A-B. The HRD Gene Signature Predicts HR-deficiency and Sensitivity to PARP Inhibitors in Cancer Cells. (A) Cells were seeded in a very low density and treated with indicated concentrations of PARP inhibitor olaparib for 10-15 days to allow colony formation. The rate of cell survival was determined by colony-formation assay. Colonies were stained with 0.25% crystal violet/25% methanol and counted both manually and digitally using ImageJ software. Each value was relative to control cells that contain only DMSO (solvent for olaparib) and represents the mean±SEM from three independent experiments. Student's t-test showed that the drug response to olaparib differed between control cell lines and individual knockdown cell lines (P<0.05). (B) MTT assay was performed with indicated concentrations of rucaparib combined with 50 μM of Temozolomide (TZM). Top curve is HCC1937; bottom curve is MCF7. Each value is relative to the value in the cells treated with vehicle control. Results are shown as mean±SEM from three independent experiments. Student's t-test showed that the drug response to rucaparib differed between cancer cell lines with and without the HRD gene signature (P<0.05).

Figure 12A:
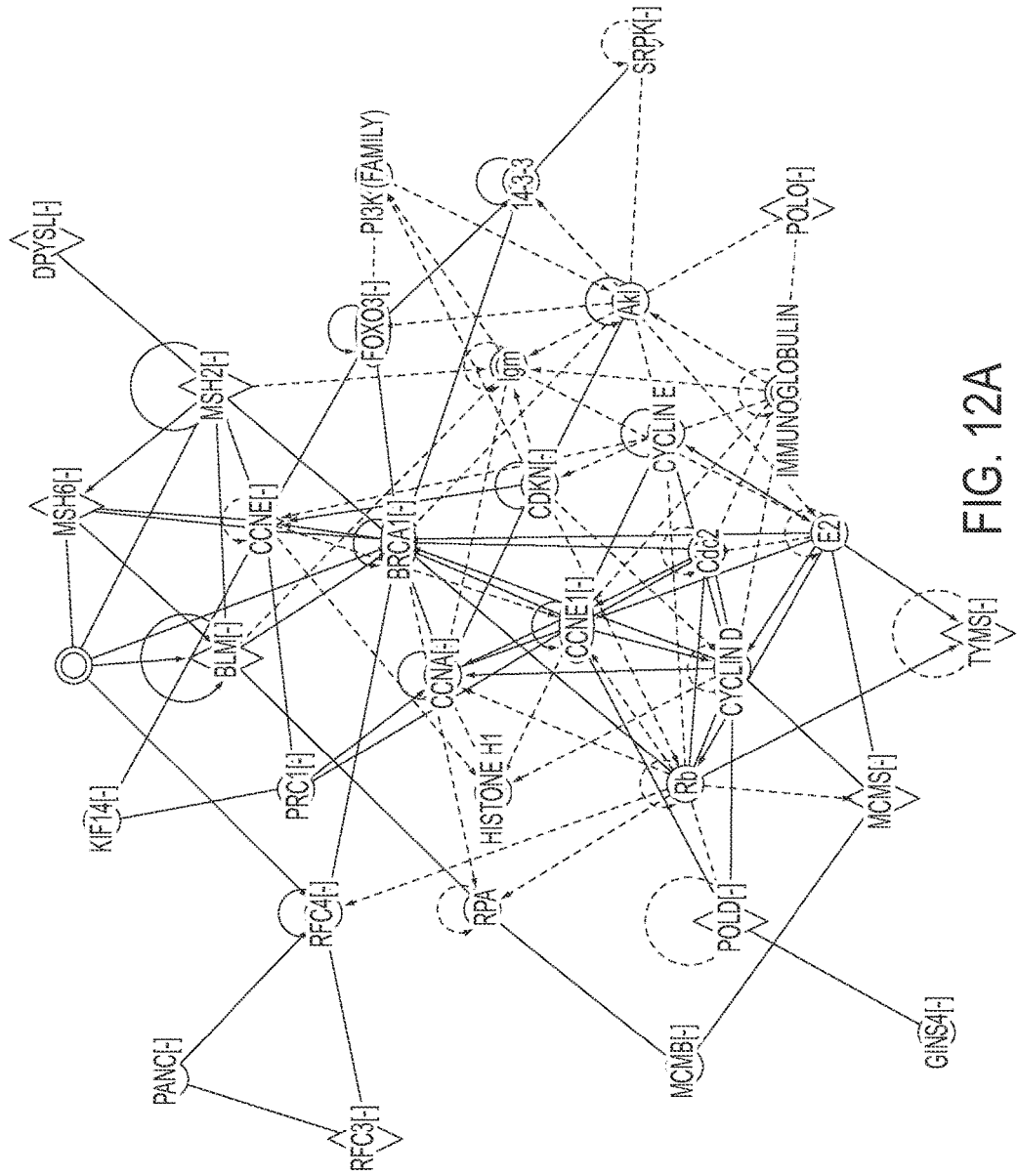
Figure 12B:
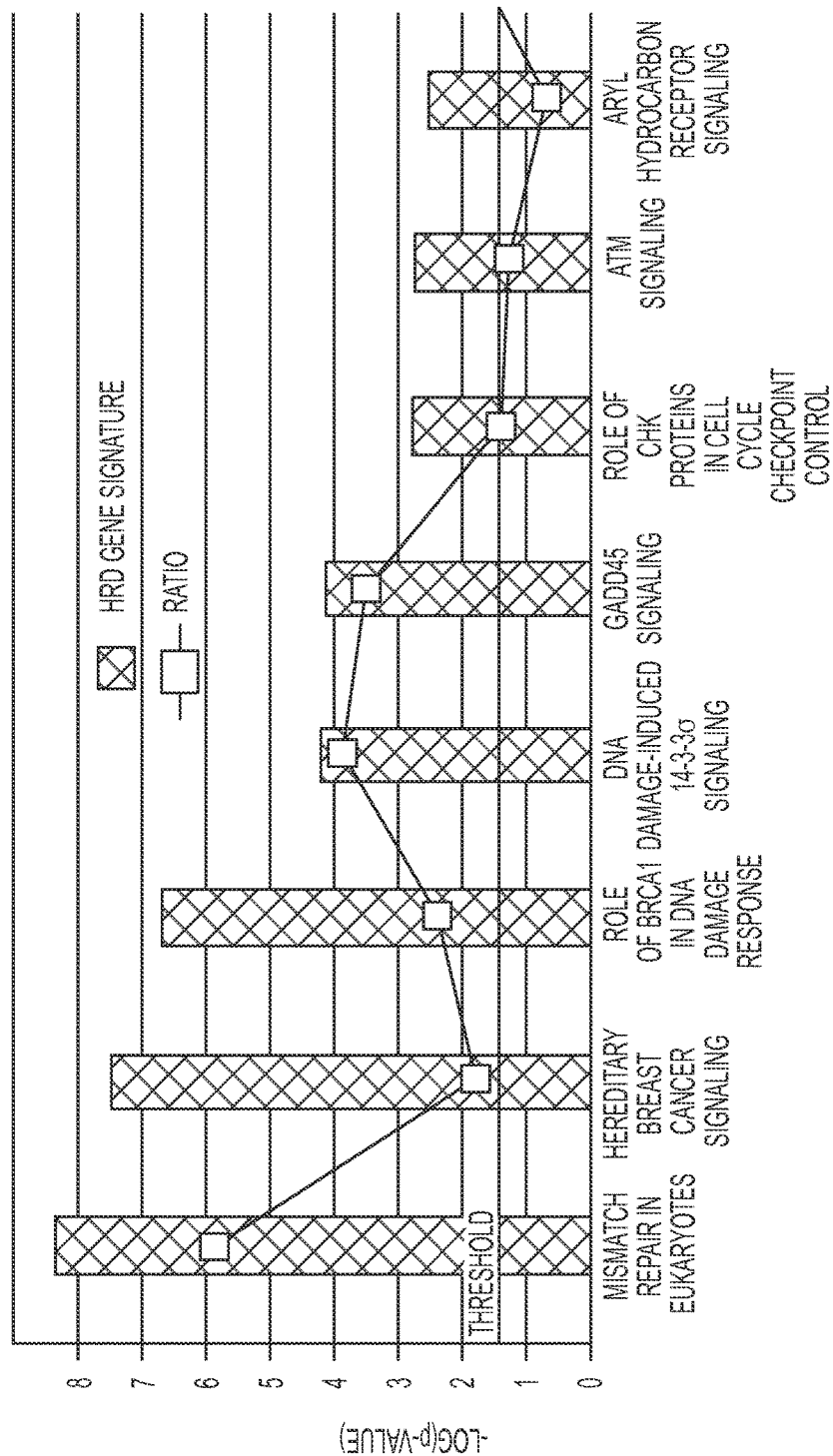

FIGS. 12A-B. The expression changes of HRD-associated protein are correlated with transcriptional alterations. (A) Both HRD gene and protein expressions are within the network of cell cycle; DNA replication, recombination, and repair; and cellular assembly and organization was analyzed by Ingenuity Systems' IPA software. In bar chat, left bar indicates gene expression changes and right bar indicates protein expression changes. Nodes are up-regulated or down-regulated as indicated in Table 3. (B) Top canonical pathways in terms of number of genes in the HRD-associated proteins on analysis with Ingenuity Systems' IPA software. Significance refers to the −log (p value), which is obtained by the Ingenuity program using Fisher's exact test. Threshold is at P=0.05.

Figure 13:
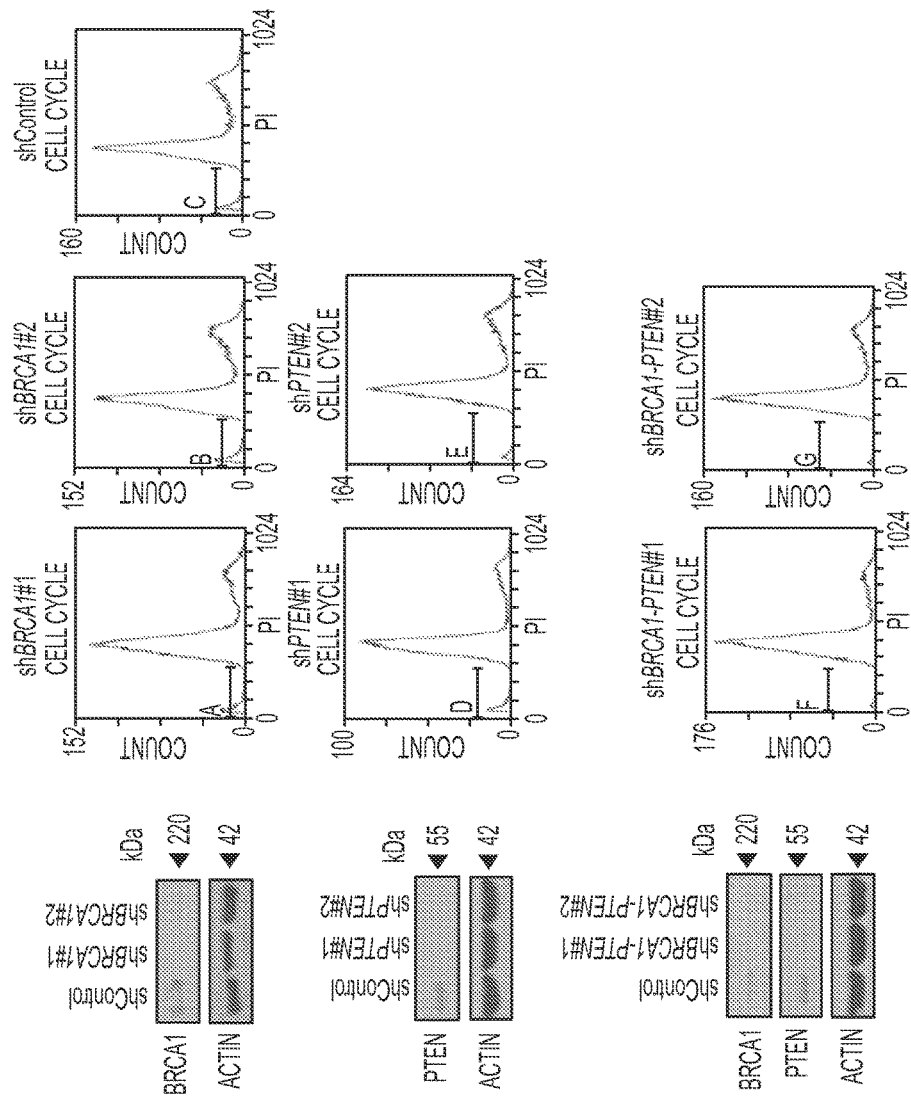

FIG. 13. Validation of effective BRCA1 or PTEN single-gene-knockdown and BRCA1-PTEN double knockdown. MCF-10A cells were infected with lentiviral particles targeting BRCA1, PTEN or both. Cells were selected in puromycin (1 μg/mL) for 10-15 days and then subjected to Western blotting, demonstrating effective knockdown by indicated antibodies. Flow cytometry analyses of cell cycle distribution in these cell lines are shown next to Western blots.

Figure 14A:
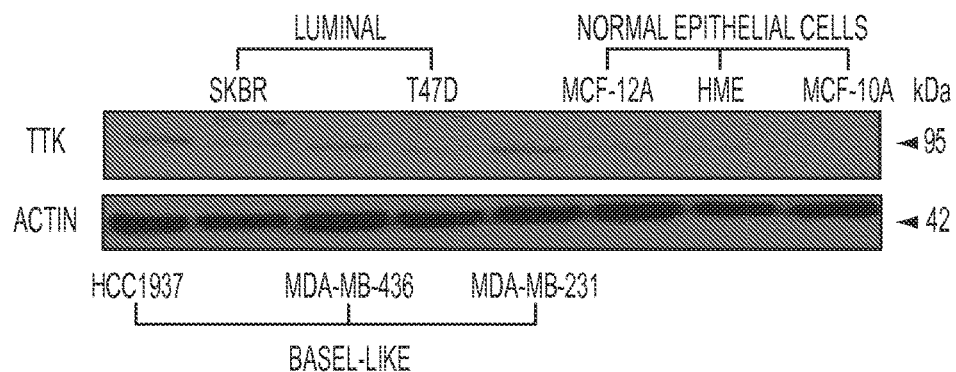
Figure 14B:
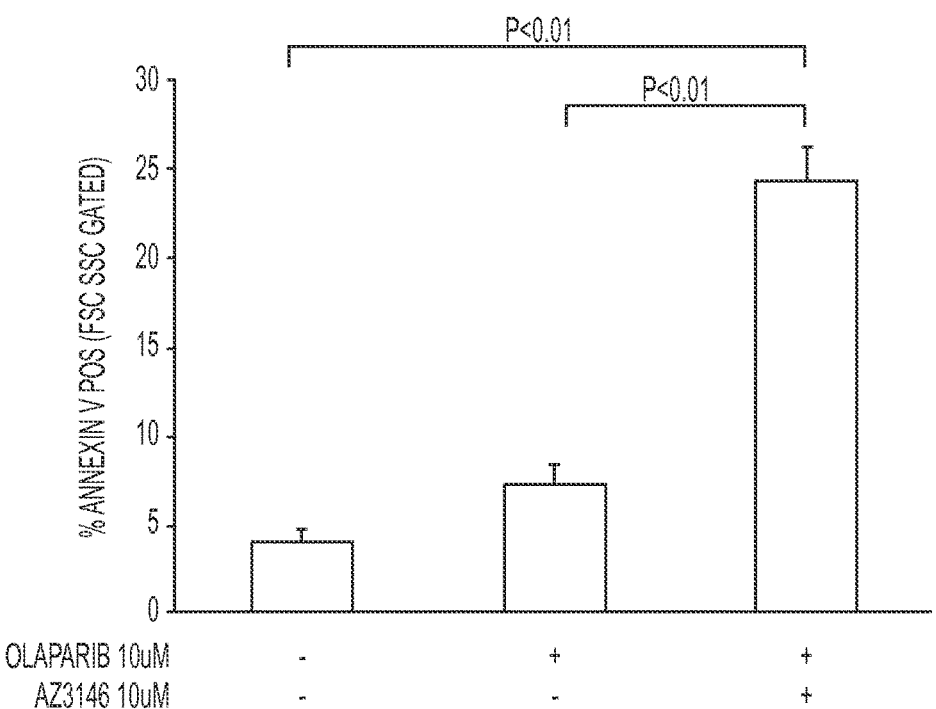

FIGS. 14A-B. TTK inhibitor enhances apoptosis induced by PARP inhibitor. (A) TTK expression levels in basal-like or luminal breast cancer cell lines and immortal human mammalian epithelial cells. Cell lysates were harvested from indicated cell lines and subjected to Western blot analysis. (B) HCC1937 cells were treated with olaparib, or combined with TTK inhibitor AZ3146 for 48 hours and subjected to apoptosis analysis. Each value represents the mean±SD from three independent experiments. Student's t-test showed increased apoptosis led by olaparib combined with AZ3146 compared to control or olaparib alone (P<0.01).

FIGS. 15A-D. Validation of PARP-inhibitor-synergizing agents. (A) U2OS cells were seeded at a high density to allow contact inhibition and transfected with I-SceI plasmid to induce DSBs. Then cells were treated with the indicated concentrations of PI3K inhibitor LY-294002 or mTOR inhibitor rapamycin for 16 hr before flow cytometry analysis of cell cycle distribution. (B) U2OS cells were treated with the indicated concentrations of LY-294002 or rapamycin after I-SceI transfection and then treated with replication inhibitor aphidicoline (10 μM) to synchronize cell cycle for 16 hr before flow cytometry analysis of cell cycle distribution. (C and D) HCC1937 cells were treated with single or combinations of olaparib (C) or rucaparib (D) with HDAC inhibitor vorinostat or Hsp90 inhibitor AUY922 and analyzed by MTT assay. Each value is relative to the value in the cells treated with vehicle control (DMSO). Results are shown as mean±SEM from three independent experiments. The CI values calculated by CompuSyn software are listed in Tables 8 and 9.

Figure 16:
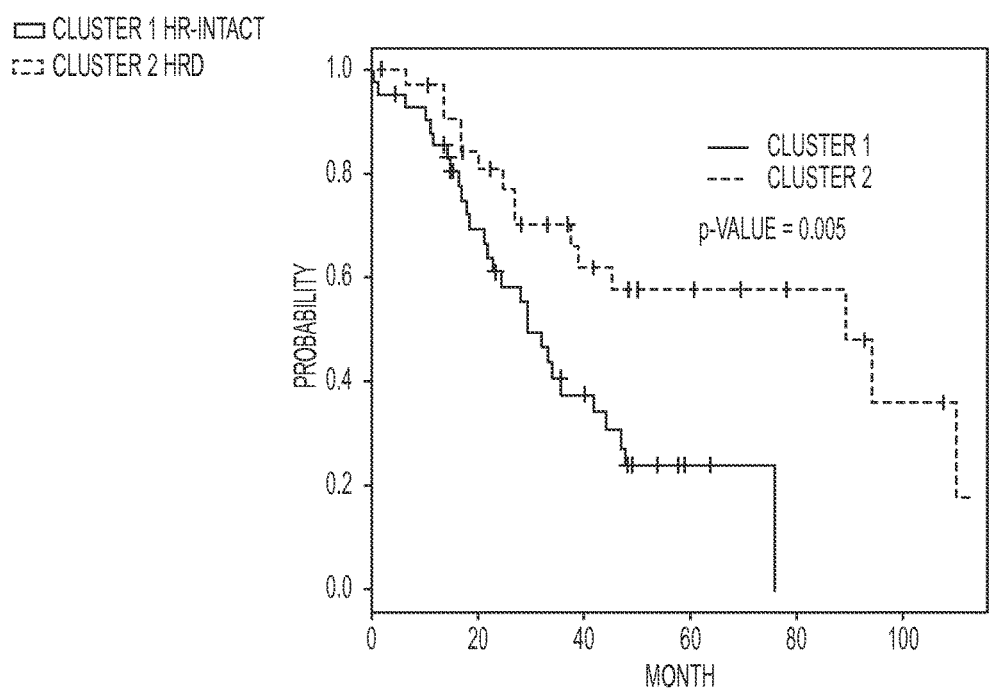

FIG. 16. The HRD Gene Signature Predicts Overall Survival in an Ovarian Cancer Patient Cohort. Datasets from patients with ovarian cancer were clustered into two groups on the basis of whether the gene expression pattern was similar to the HRD gene signature. Kaplan-Meier overall survival curves are shown. Top curve is Cluster 2; bottom curve is Cluster 1. P values are from log-rank test.

Figure 17A:
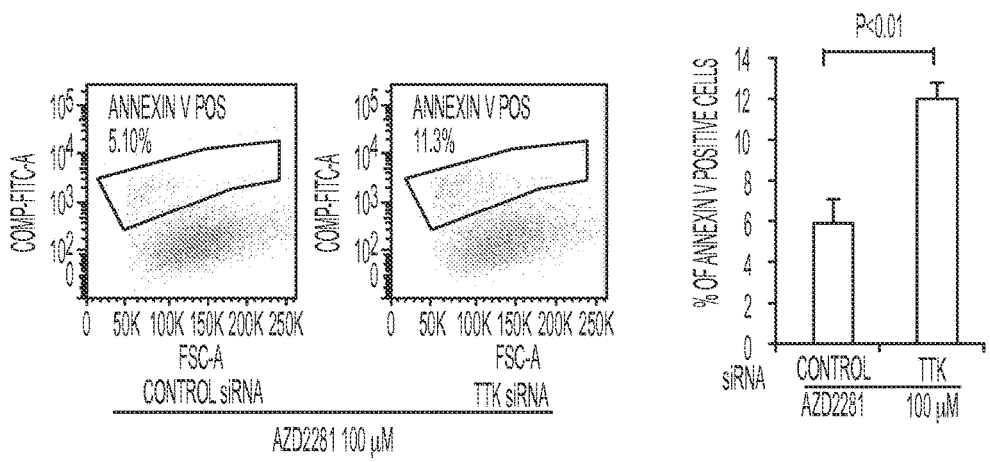
Figure 17B:
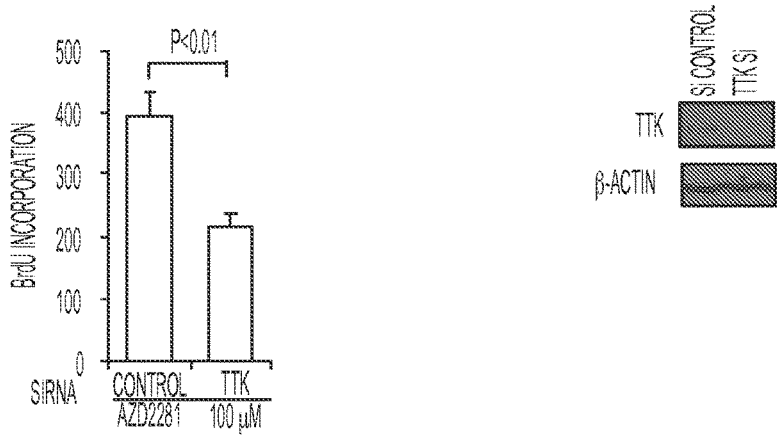
Figure 17B:
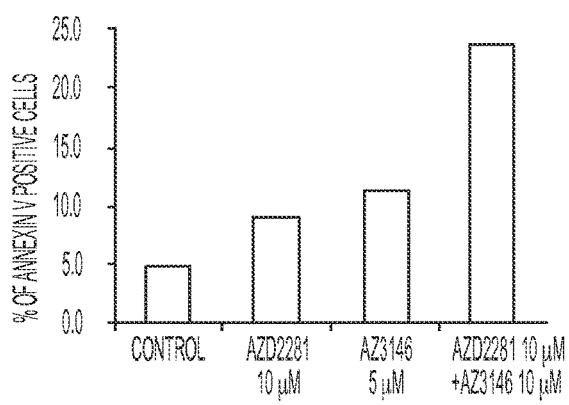

FIGS. 17A-B. Inhibition of TTK sensitizes PARP inhibitor treatment. (A) MDA-MB-436 cells were transfected with control siRNAs or TTK siRNAs and then treated with PARP inhibitor AZD2281 at indicated concentrations for apoptosis analysis (Left) and BrdU analysis (Right). Western blot showing efficient knockdown of TTK was next to the bar graph. (B) HCT1937 cells were treated with AZD2281, TTK inhibitor AZ3146 or both for 48 hrs and then subjected to apoptosis analysis.

Figure 18:
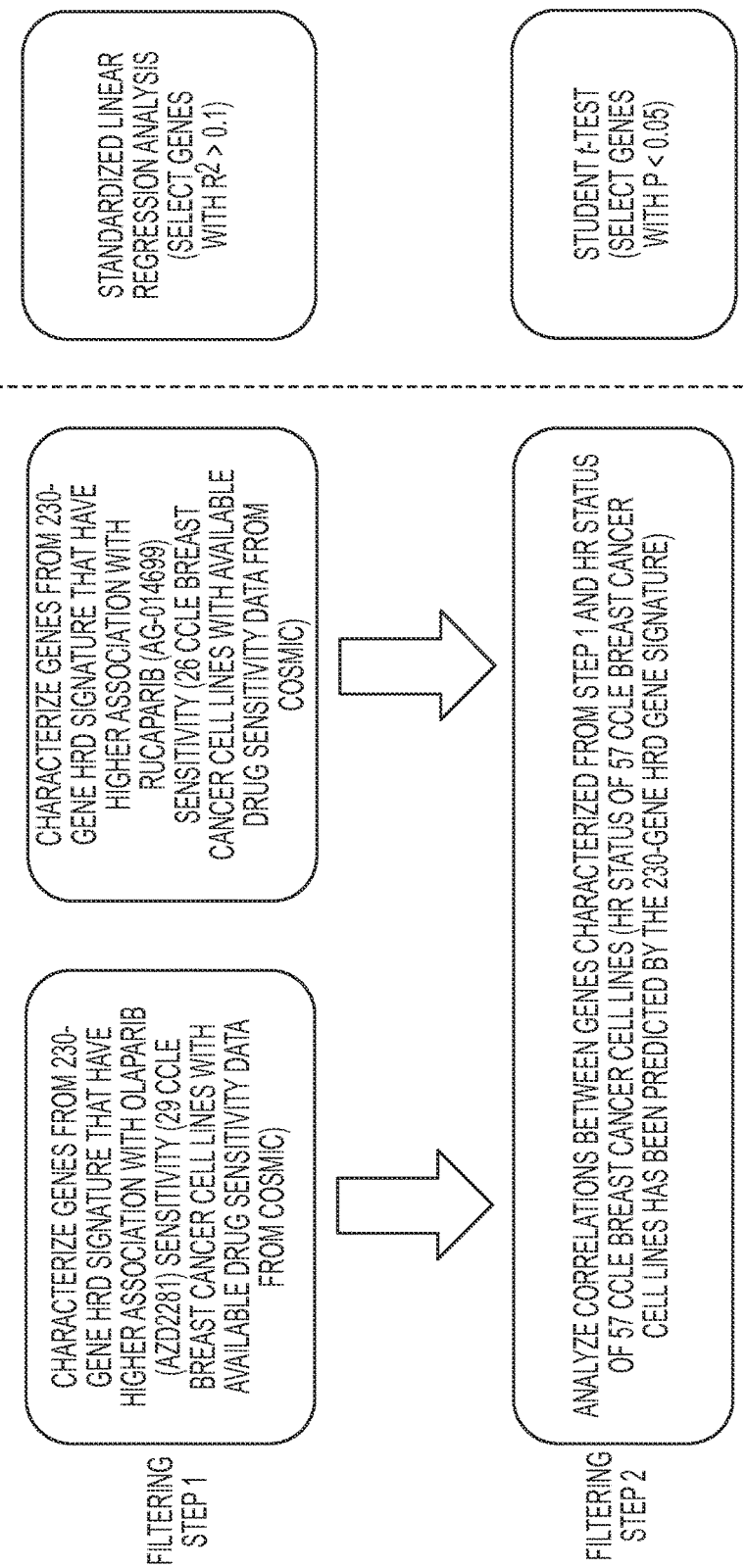

FIG. 18. Schematic of two-step filtering procedure for the identification of predictive markers of PARPi response.

Figure 19:
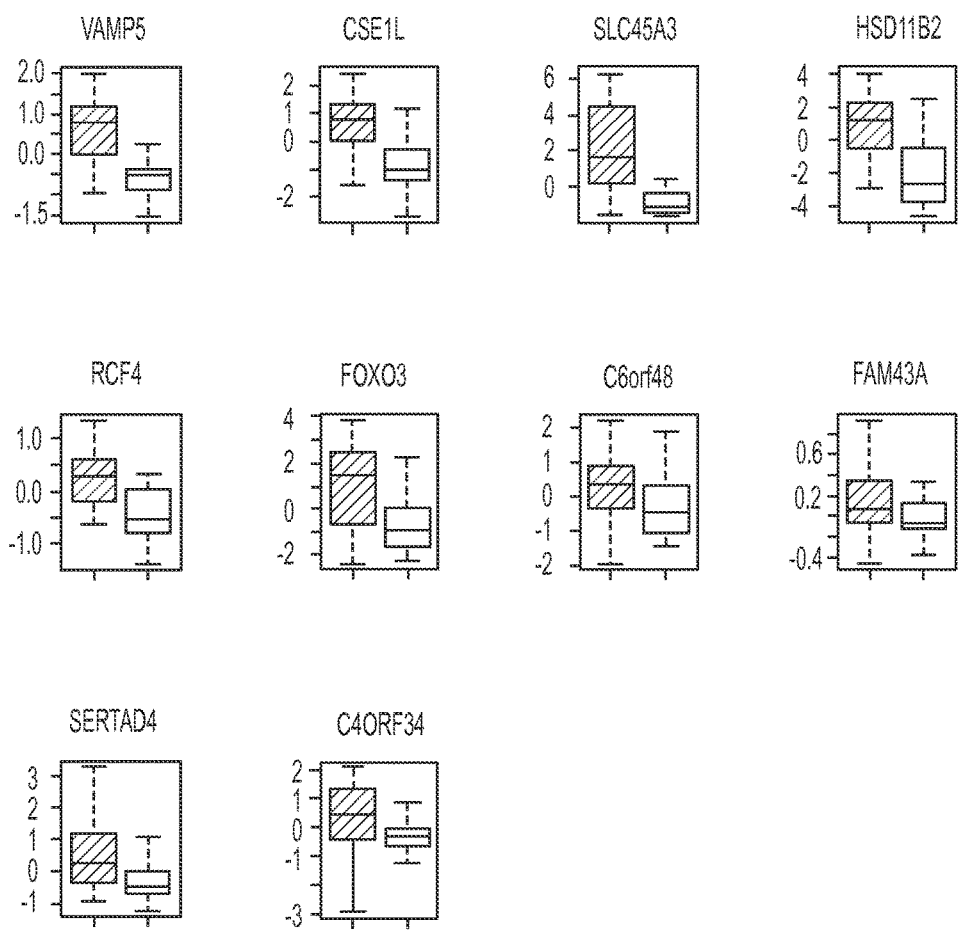

FIG. 19. Expression levels of genes whose expression was statistically different between HRI cell lines and HRD cell lines.

Figure 20:
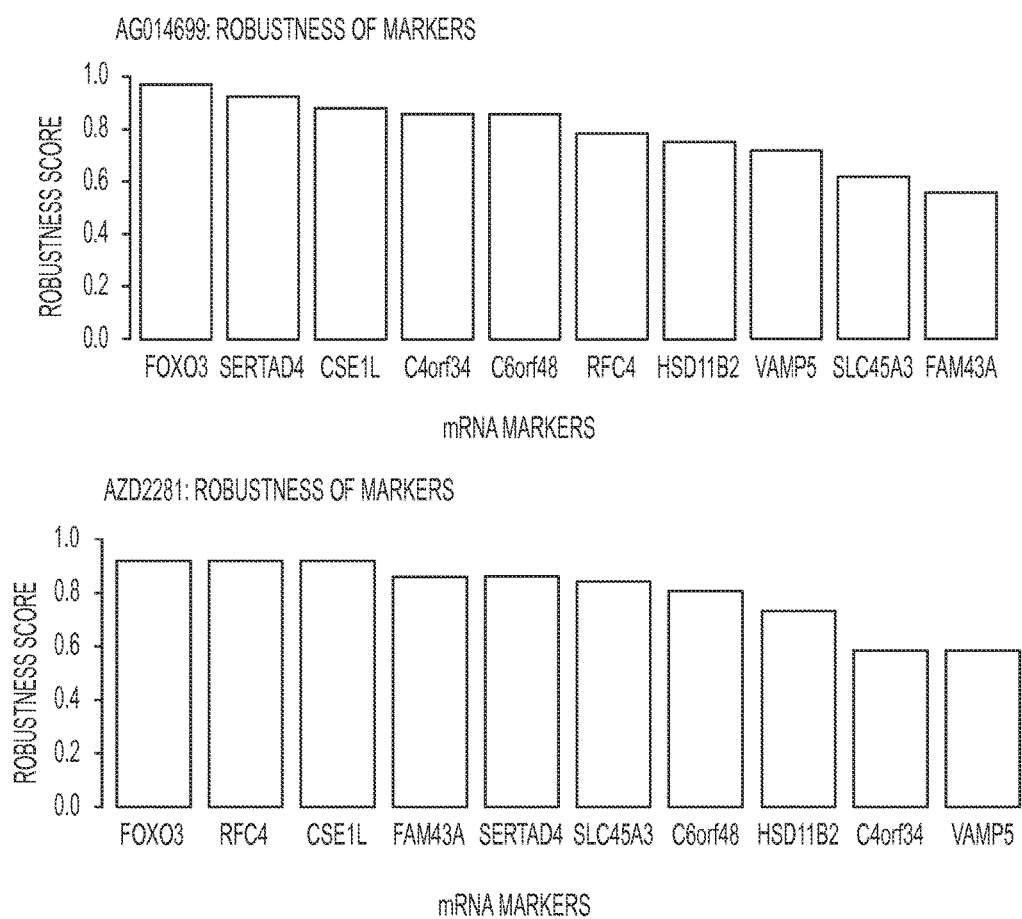
Figure 21A:
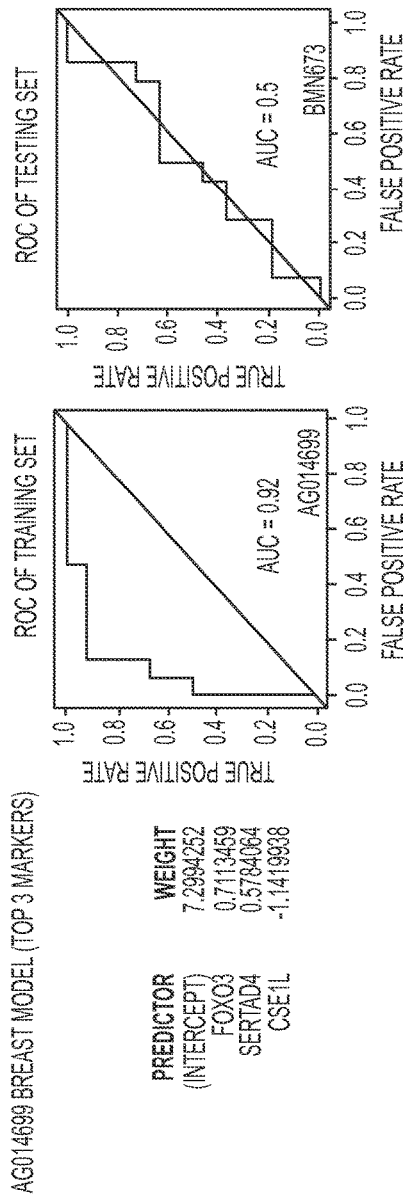
Figure 21B:
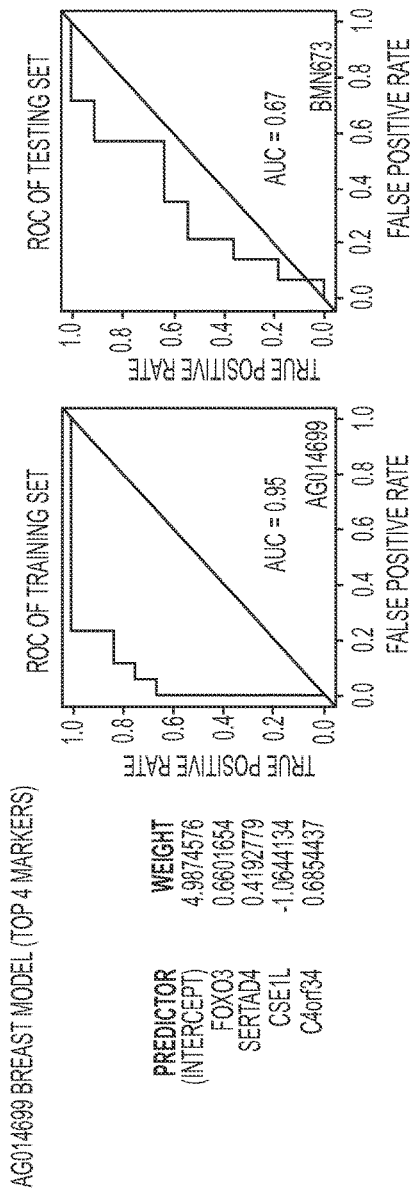
Figure 21C:
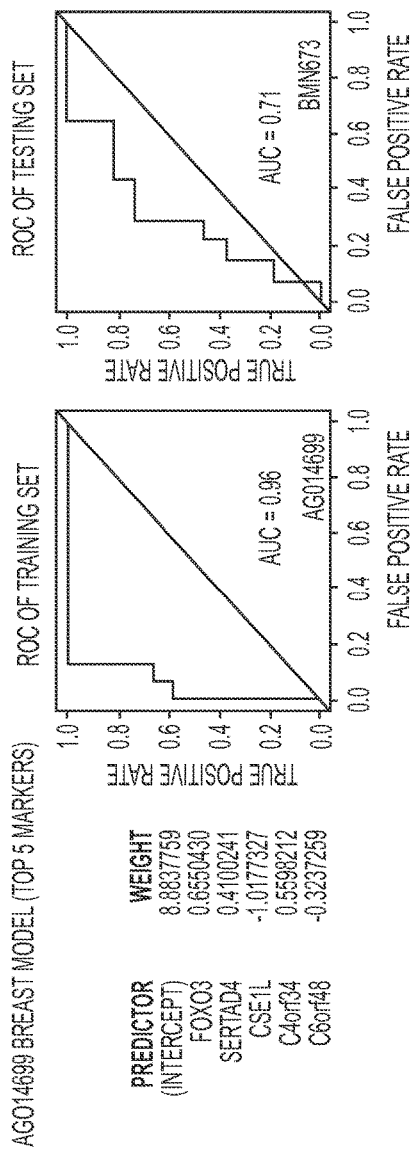
Figure 21D:
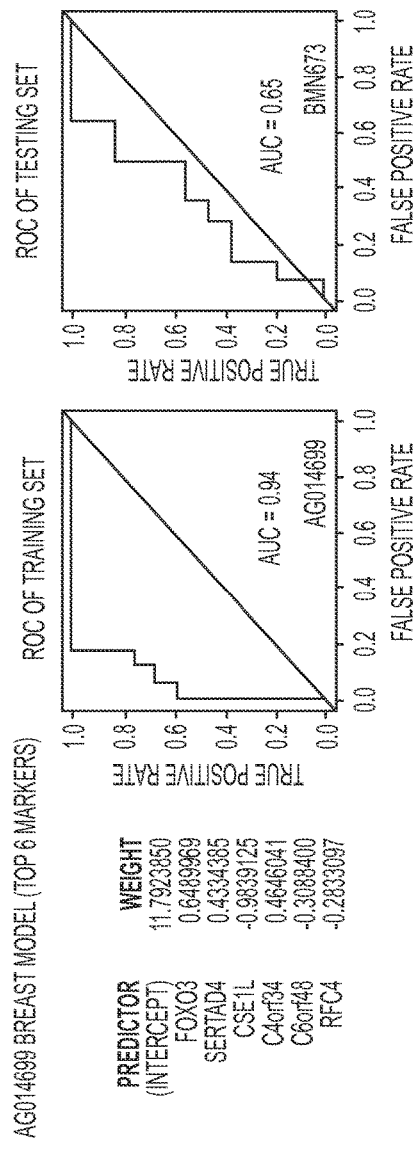
Figure 21E:
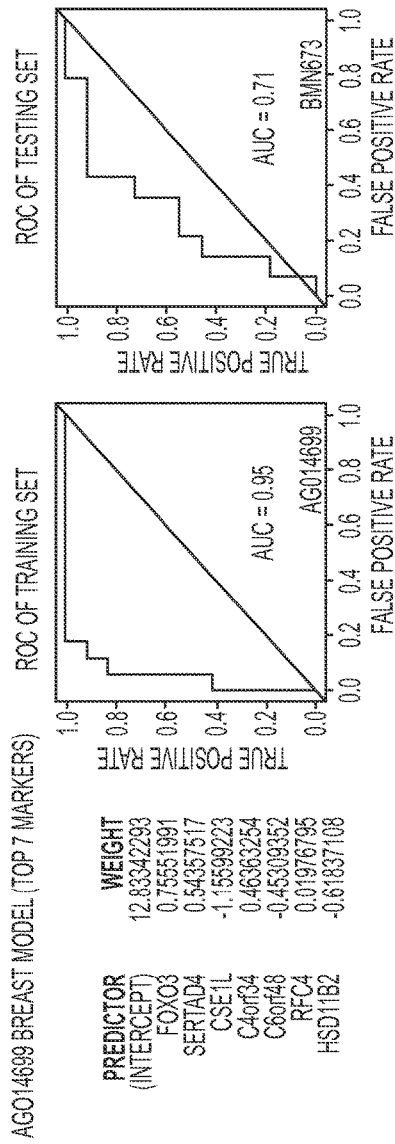
Figure 21F:
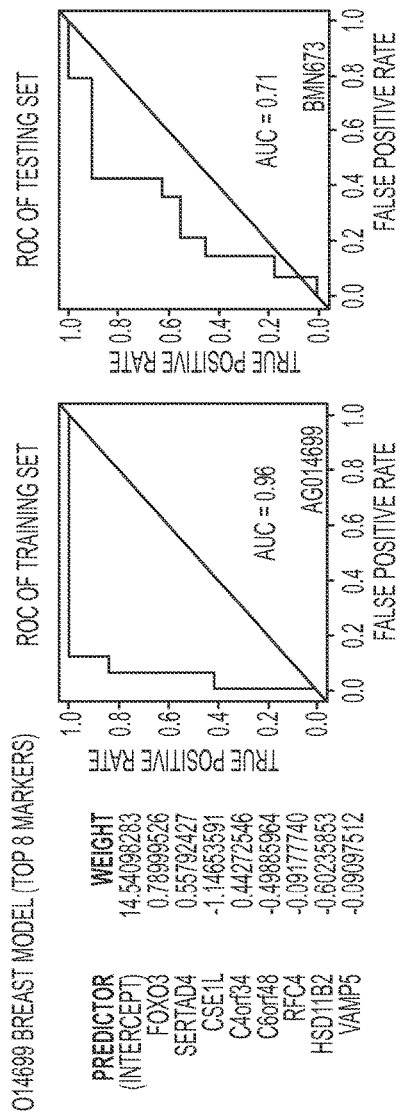
Figure 22A:
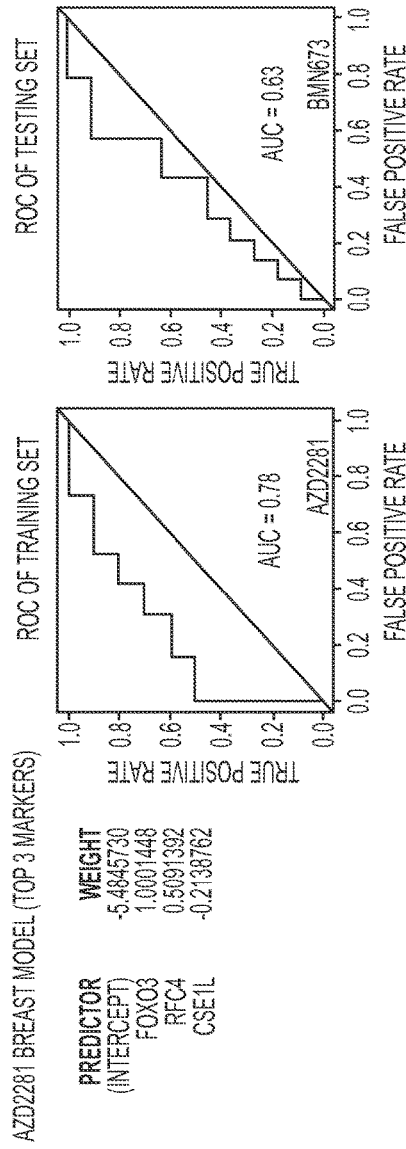
Figure 22B:
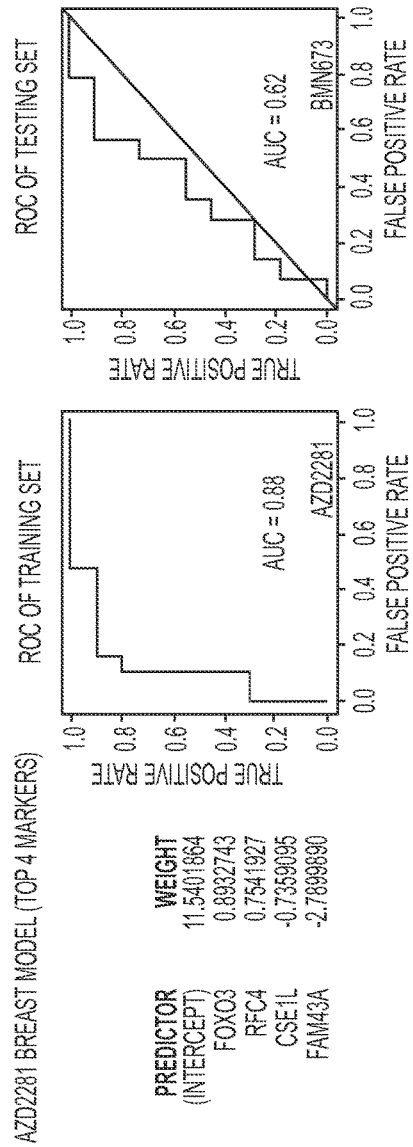
Figure 22E:
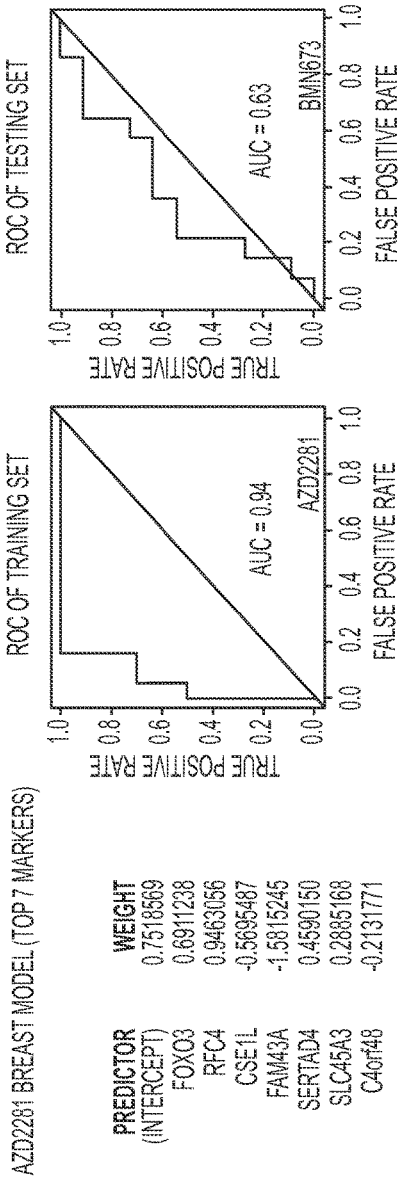
Figure 22F:
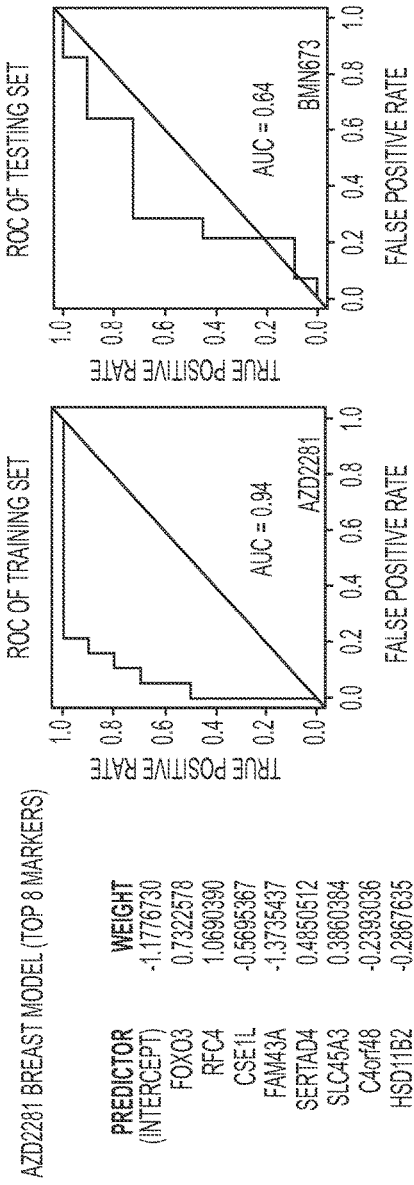
Figure 22G:
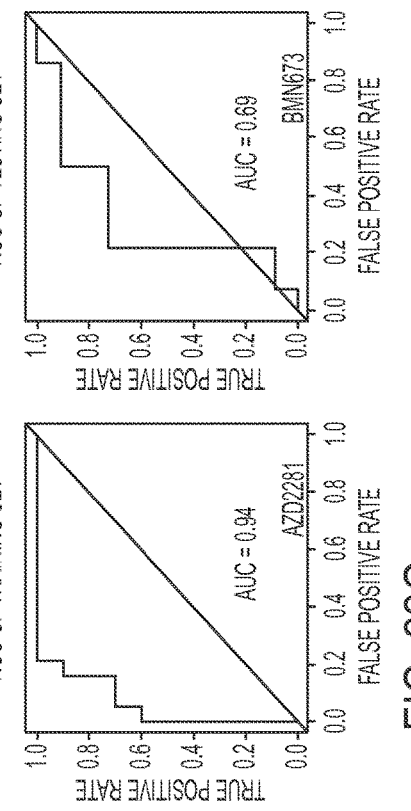
Figure 22H:
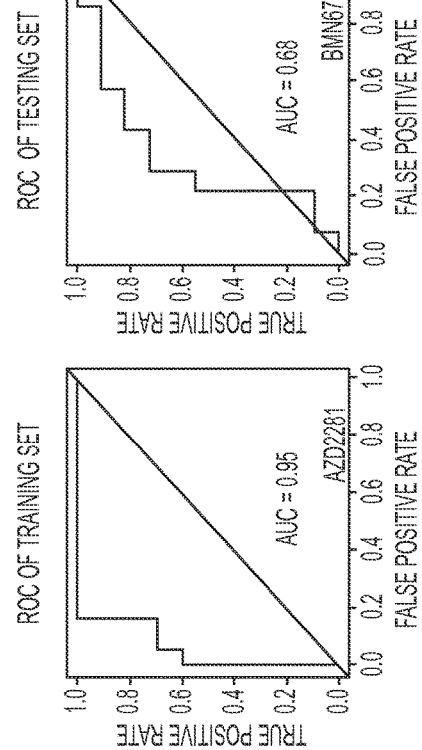

FIG. 20. Ten mRNA markers organized by robustness score for AG014699 and AZD2281 for the breast cancer cell line set.

FIGS. 21A-H. Models of 3-10 molecular predictors (panels A-H, respectively) for AG014699 using the breast cancer cell line set.

FIGS. 22A-H. Models of 3-10 molecular predictors (panels A-H, respectively) for AZD2281 using the breast cancer cell line set.

Figure 23:
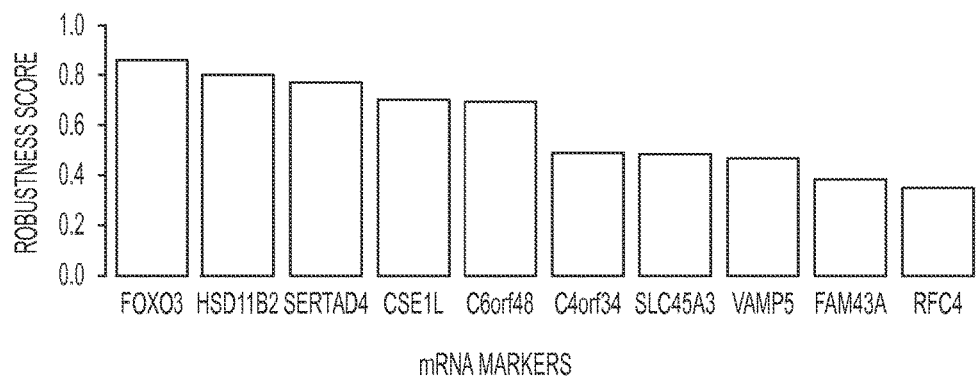
Figure 23:
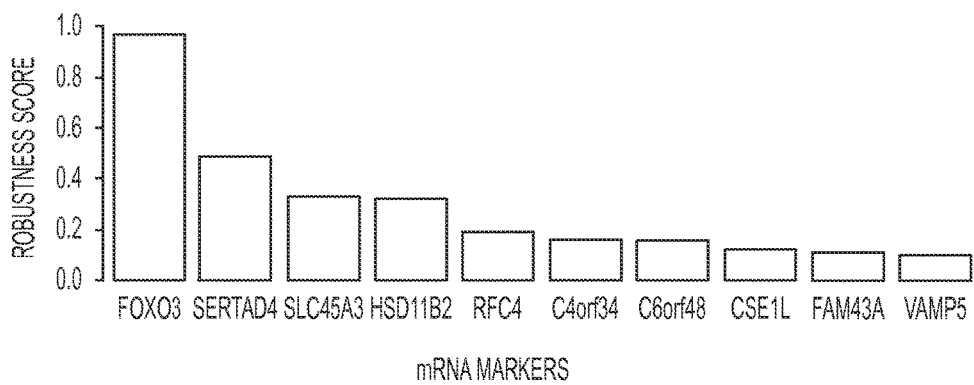
Figure 24A:
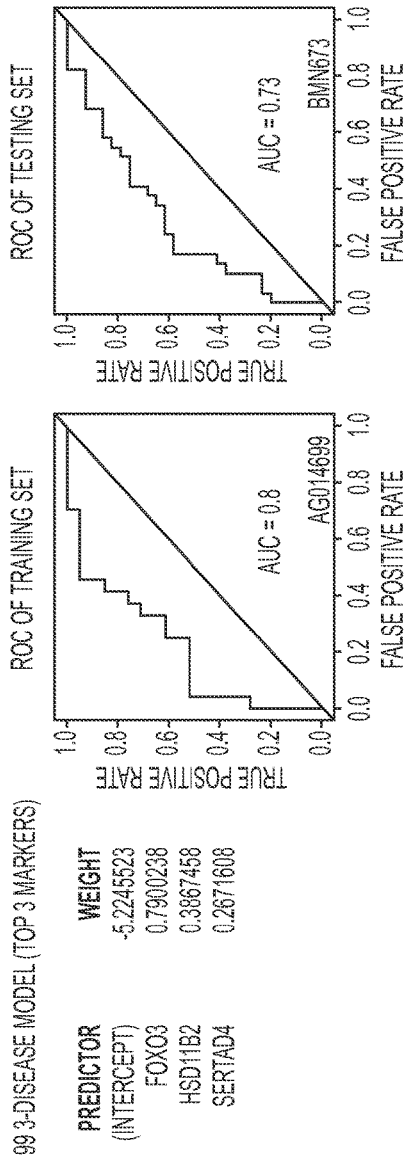
Figure 24B:
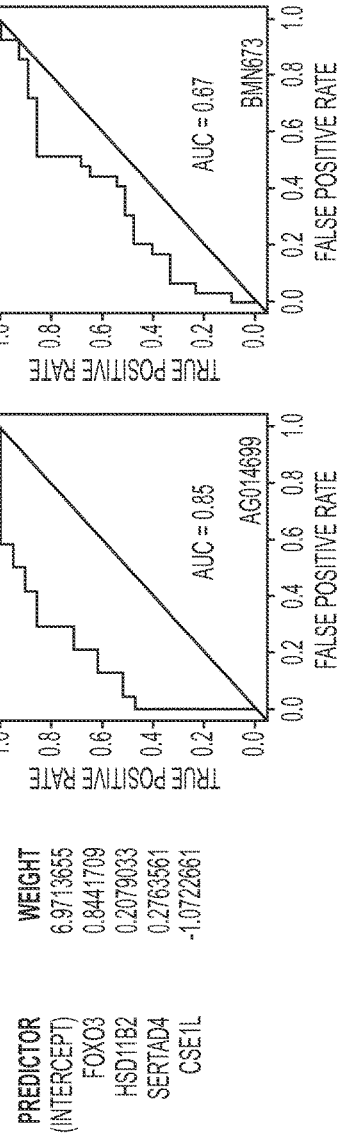
Figure 24C:
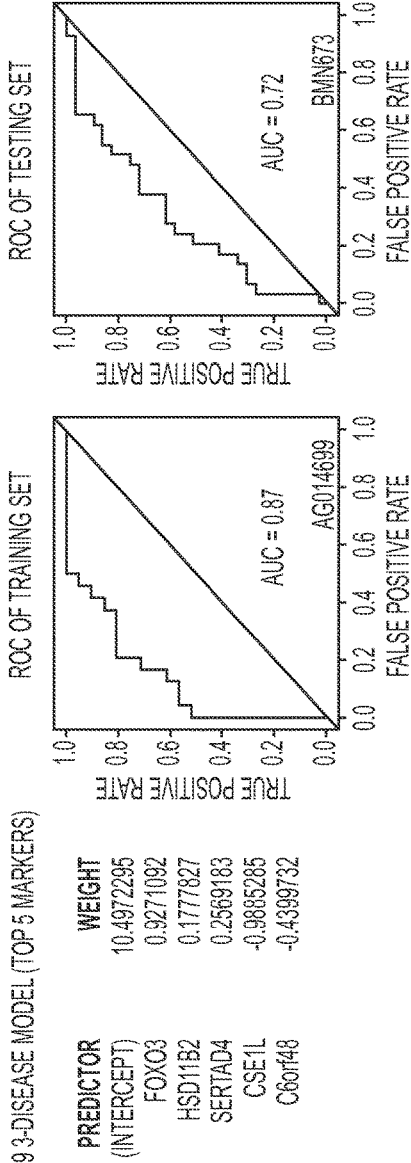
Figure 24D:
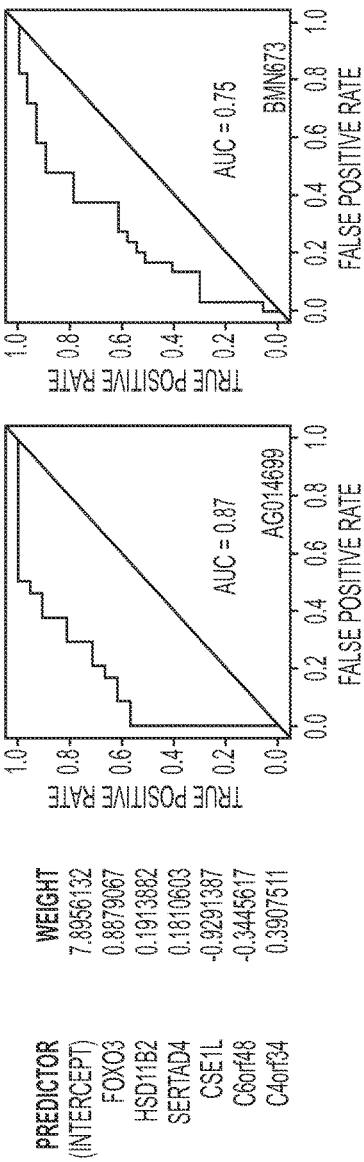
Figure 24E:
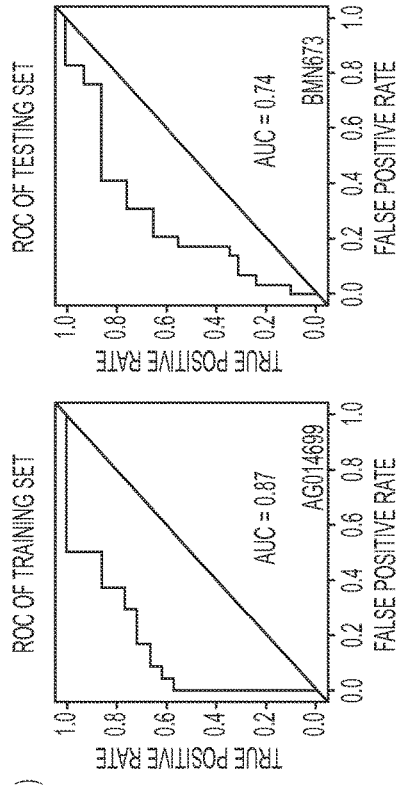
Figure 24F:
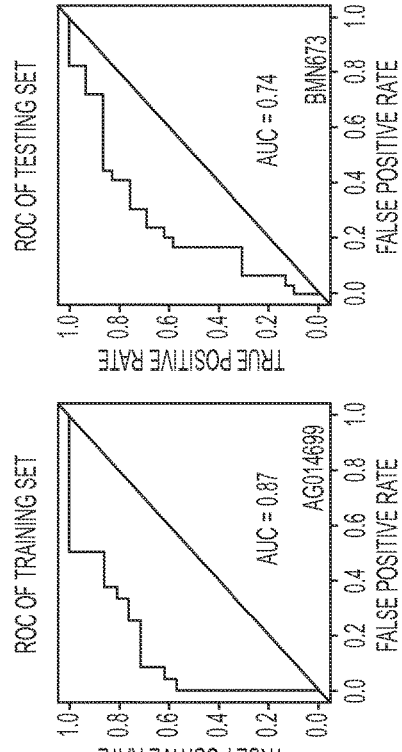
Figures 24G, 24H:
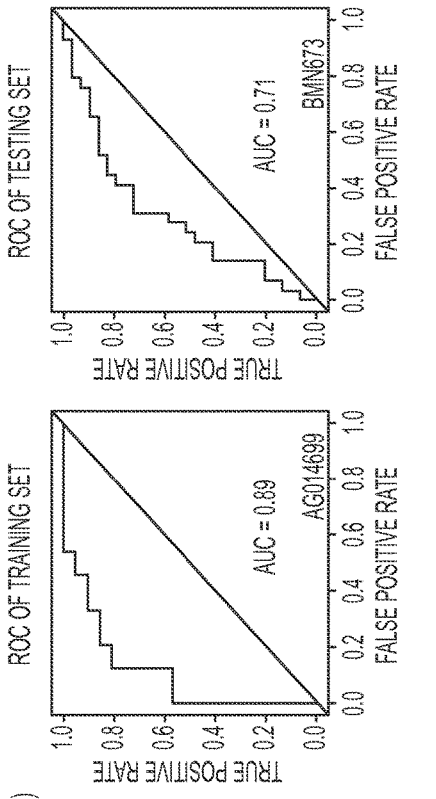
Figure 25A:
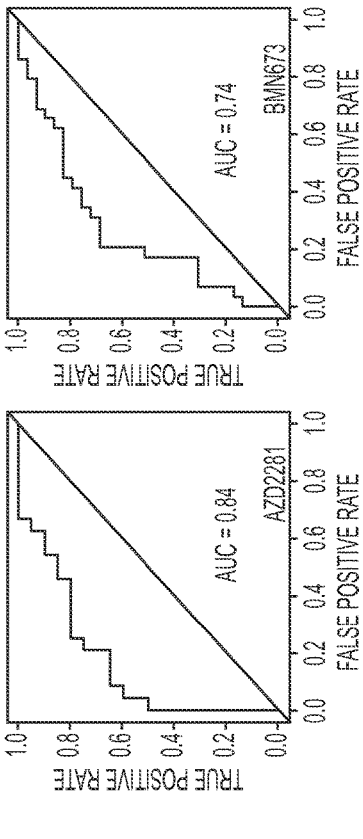
Figure 25A:
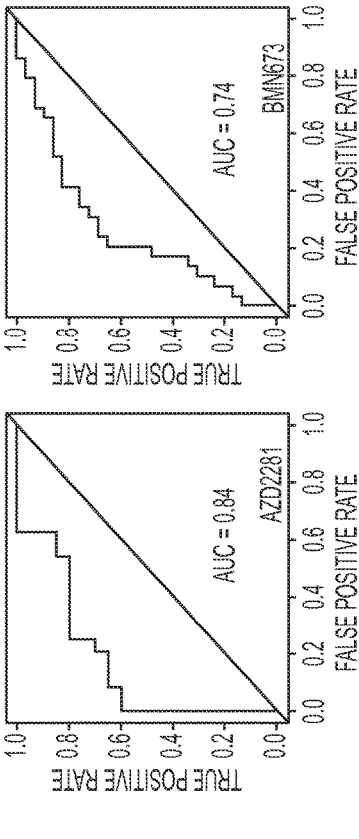
Figure 25B:
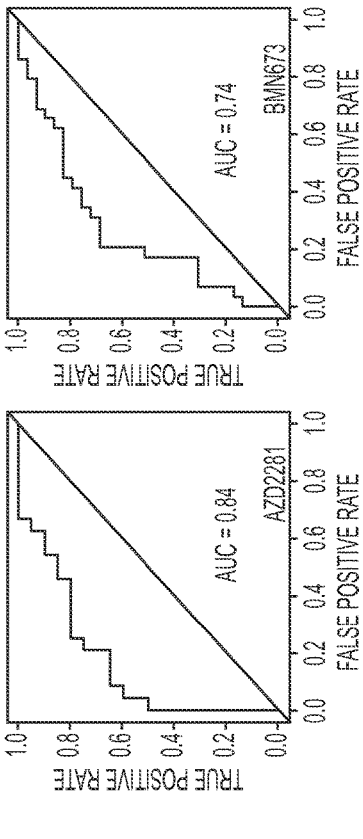
Figure 25B:
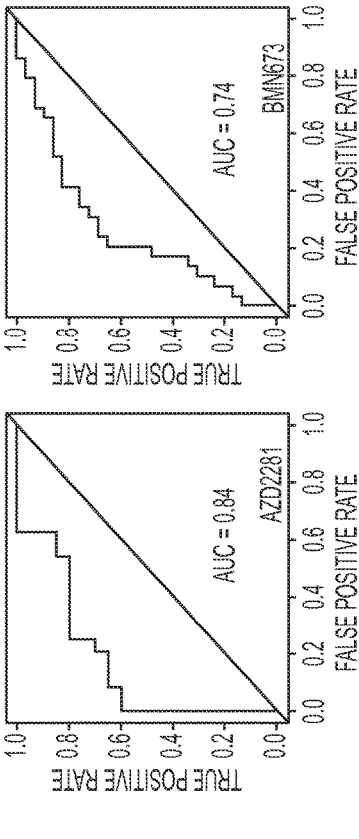
Figures 25E, 25F:
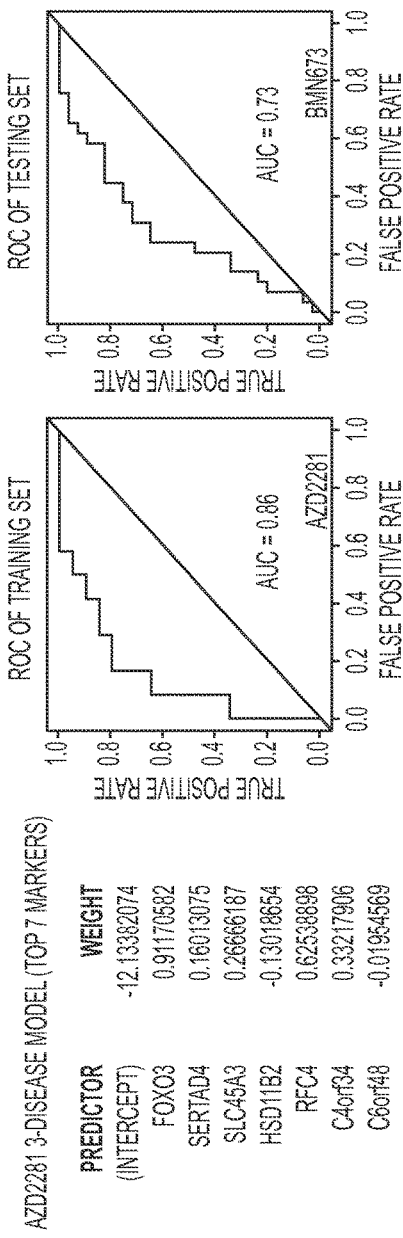

FIG. 23. Ten mRNA markers organized by robustness score for AG014699 and AZD2281 for the 3-disease set.

FIGS. 24A-H. Models of 3-10 molecular predictors (panels A-H, respectively) for AG014699 using the 3-disease set.

FIGS. 25A-H. Models of 3-10 molecular predictors (panels A-H, respectively) for AZD2281 using the 3-disease set.

Figure 26B:
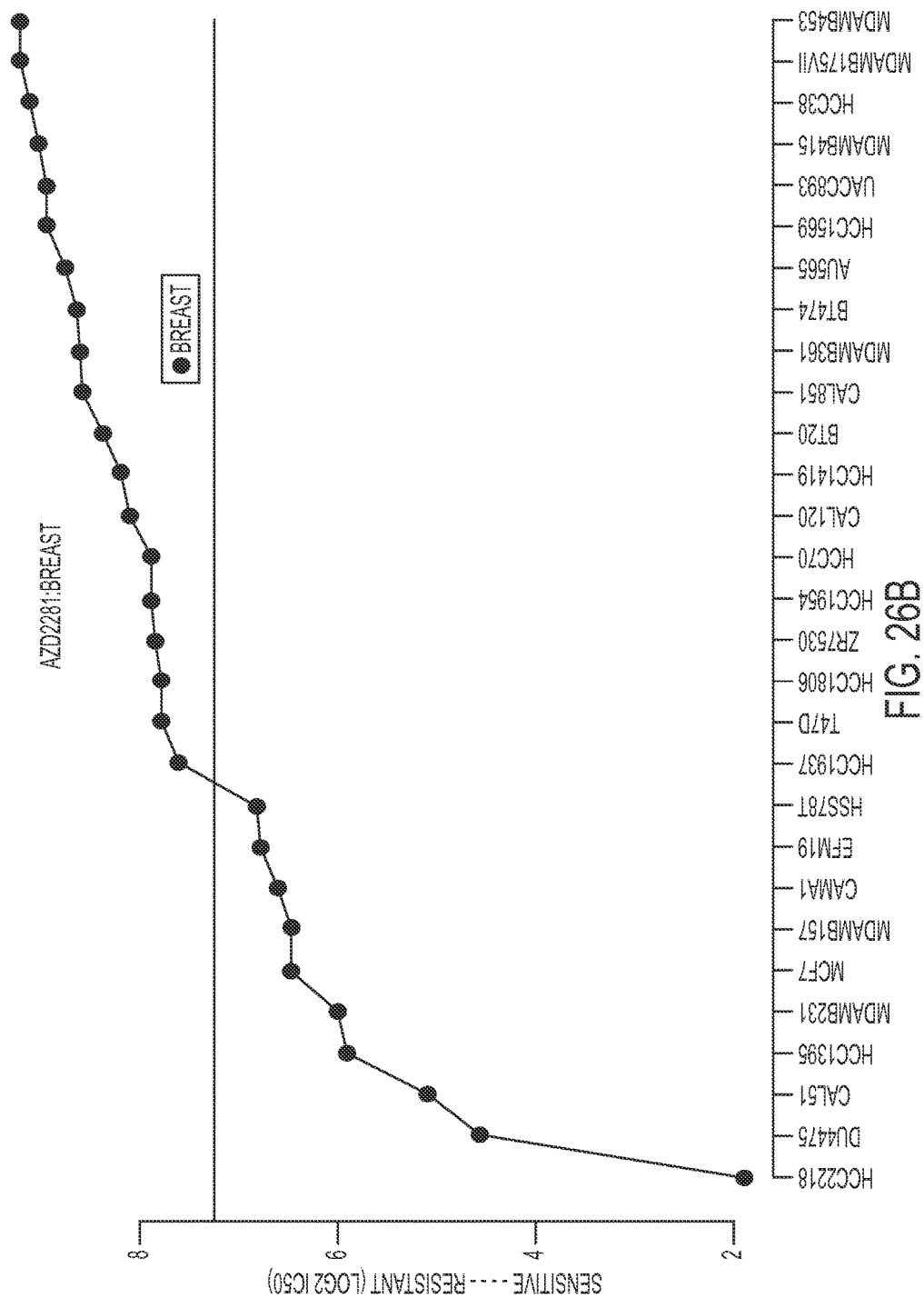
Figure 26B:
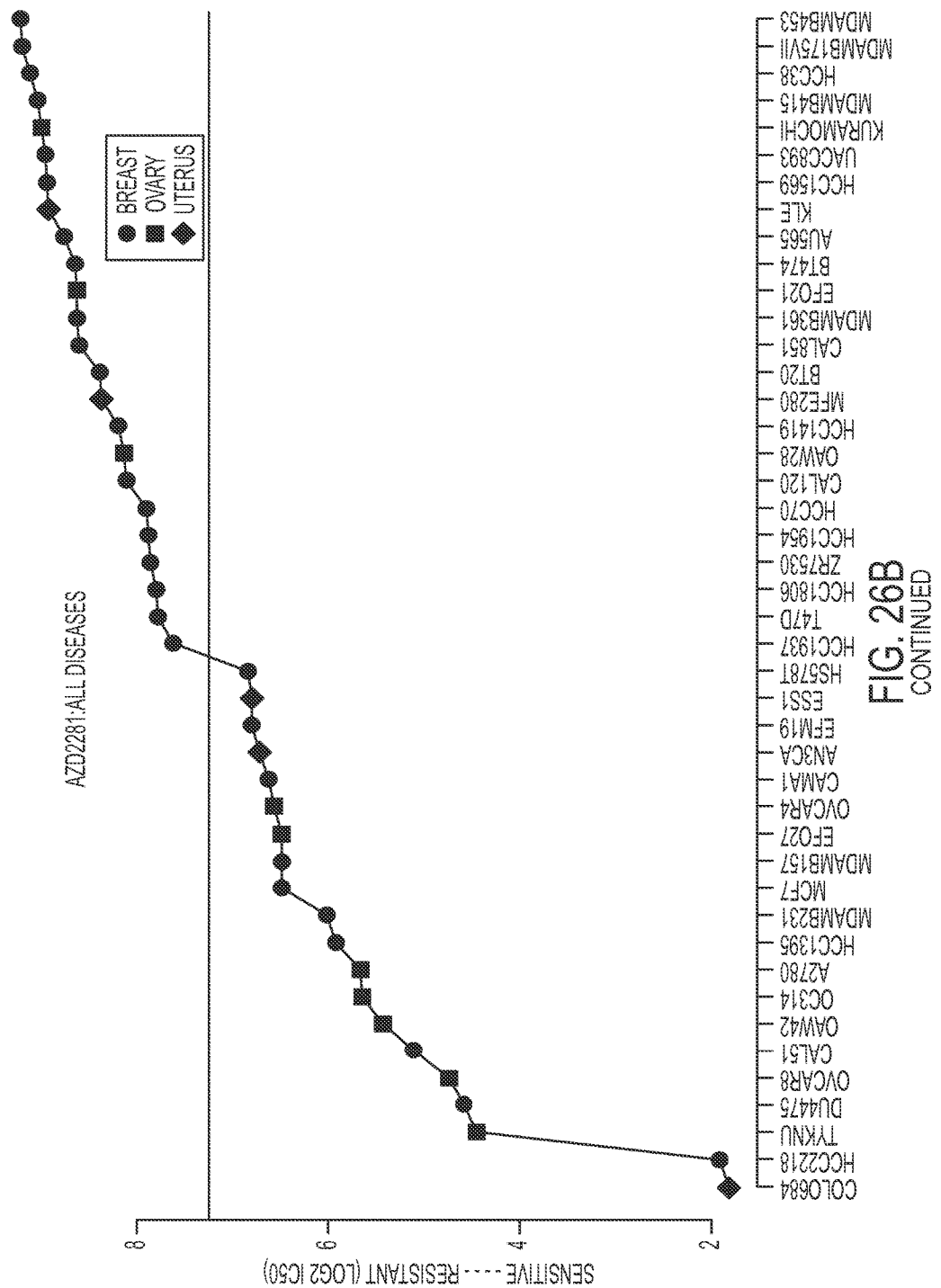

FIGS. 26A-B. $IC_{50}$ values for AG014699 (A) and AZD2281 (B) across all cell lines.

Figure 27:
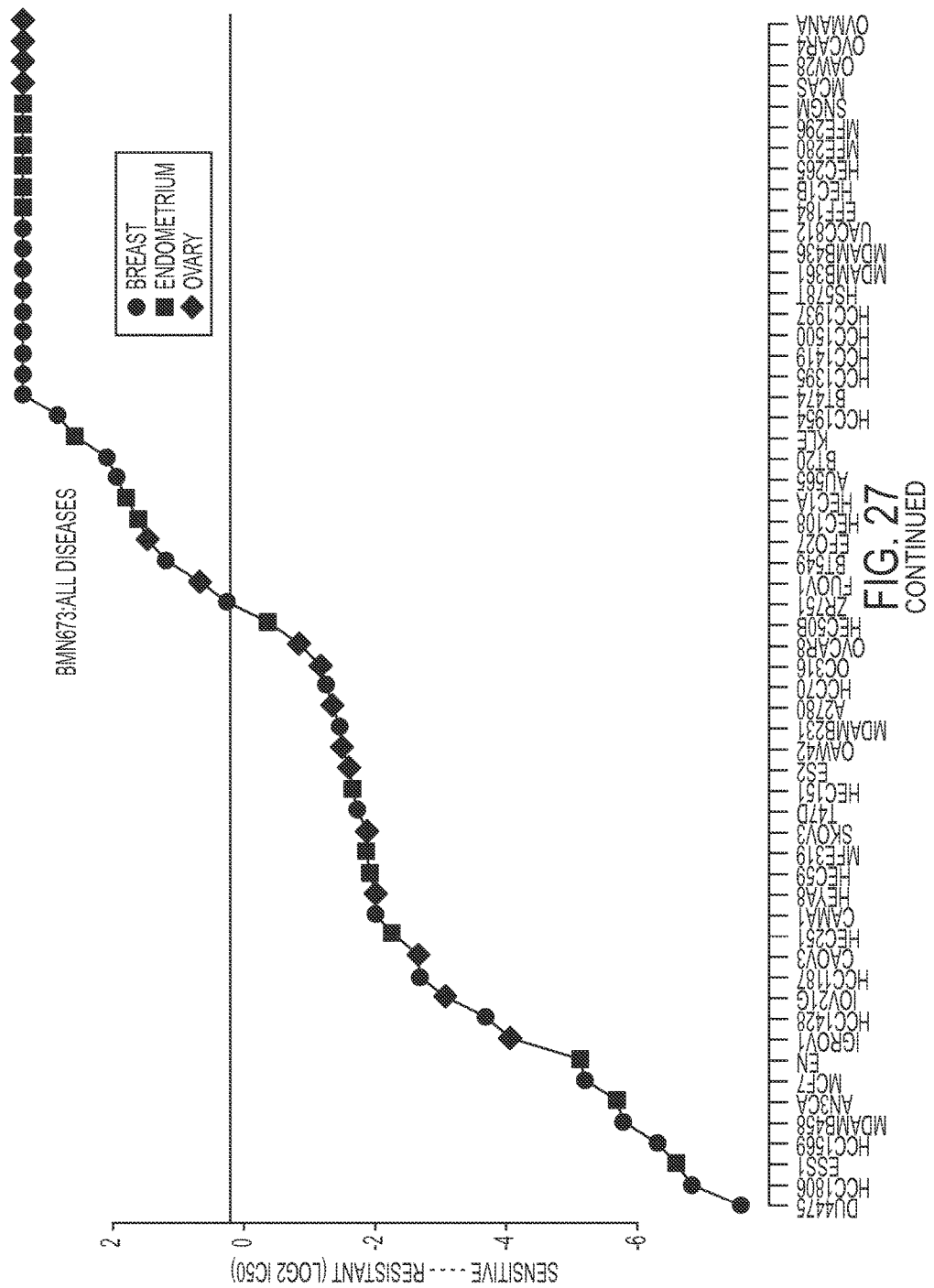

FIG. 27. $GI_{50}$ values for BMN673 across all cell lines.

Figure 28:
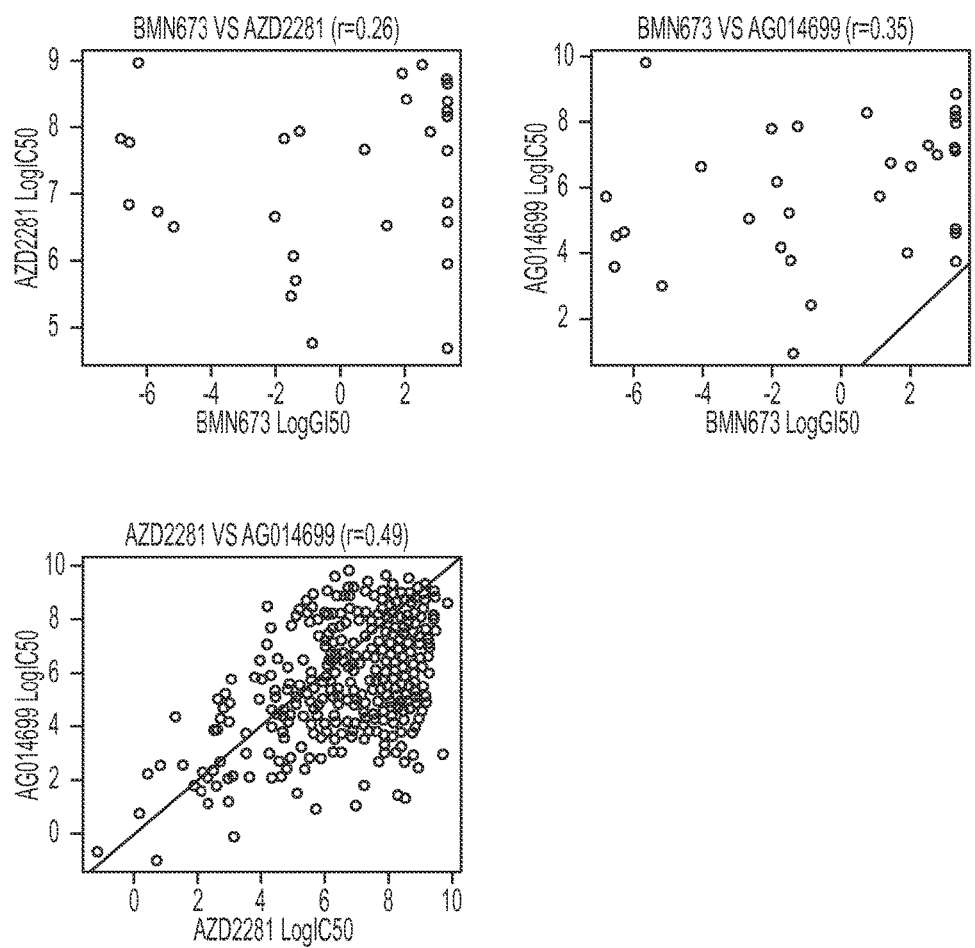

FIG. 28. Correlation of $IC_{50}/GI_{50}$ between each PARP inhibitor.

DESCRIPTION OF ILLUSTRATIVE EMBODIMENTS

Homologous recombination (HR)-mediated DNA repair deficiency predisposes to cancer development, but also sensitizes cancer cells to DNA-damage-inducing therapeutics, and as such, provides therapeutic opportunities with poly-ADP ribose polymerase (PARP) inhibitors, which are synthetically lethal with HRD. An HR-defect (HRD) gene signature was identified, which can be used to functionally assess HR repair status and predict clinical outcomes and sensitivity to PARP inhibitors. By using this HRD gene signature as a functional network analysis tool, it was discovered that the combinatorial effects of co-existing genetic changes, such as concurrent loss of two major tumor suppressors BRCA1 and PTEN, extensively rewired the HRD phenotype, which is found in cells with a defect of either BRCA1 or PTEN alone, and conferred resistance to PARP inhibitor treatment. Moreover, the HRD gene signature may serve as an effective drug discovery platform to identify agents targeting HR repair as potential chemo-radio-sensitizers, such that TTK, mTOR and PI3K inhibitors could induce HR-repair deficiency and sensitize to PARP inhibitors. This HRD gene signature is able to predict clinical outcomes across multiple cancer lineages. Therefore, gene expression profiling, specifically molecular profiling of HR repair, can be used to assess the functional status of the HR repair network, which can provide both biological insights and clinical implications in cancer and as well as provide prognostic and therapeutic information.

Defects in BRCA1/2 and other HR repair genes are associated with genetic predisposition to cancer, predict improve outcomes and response to PARP inhibitors as well as specific types of chemotherapy. Due to the number of HR genes, it is difficult to determine which tumors are HR-repair-deficient by sequencing alone. The inventors thus developed a HR-defect transcriptional profile able to robustly predict HR-repair deficiency. Clinically, many HR-repair deficient tumors do not respond to PARP inhibitors. Unexpectedly, concurrent loss of BRCA1/2 and other genes, such as PTEN, can restore HR leading to resistance to PARP inhibitors. The inventors show that TTK, mTOR and PI3K inhibitors can induce HR-repair deficiency identifying potential rational drug combinations that warrant clinical exploration.

Concurrent genetic alterations in cells with BRCA1/2 mutations can restore functional HR repair and may explain intrinsic and acquired resistance to PARP inhibitors. Analysis of PARP inhibitor-resistant cancer cell clones suggested that intragenic "reversion mutations" can correct the original mutation and restore the function of BRCA1/2 (Bunting et al., 2010; Sakai et al., 2009; Sakai et al., 2008; Swisher et al., 2008). More recently, two studies showed that loss of another DNA-damage-responsive gene, 53BP1, can at least partially restore functional HR repair in BRCA1-deficient cells (Bunting et al., 2010). Concurrent BRCA1 and 53BP1 defects are frequently observed in TNBC (Bouwman et al., 2010). Thus the HR repair network can evolve under selection pressure during tumor progression or as a result of DNA damage-inducing therapy. The implementation of PARP inhibitors into patient management will largely depend on accurate identification of patients with HRD as well as on approaches to prevent emergence of resistance. Thus, the aforementioned observations raise an important question: Can a molecular measurement of a deficient-HR repair network be identified that will allow us to accurately predict which patients have HR-repair-deficient tumors? As a corollary, are there rational therapeutic combinations that will increase the efficacy of PARP inhibitors and prevent emergence of therapeutic resistance?

In some aspects, the present invention provides a gene signature generated from HR repair-deficient cell lines, which can be used as a clinical tool for stratifying patients with HR repair-deficiency and for PARP inhibitor treatment.

Recently a new class of poly-ADP ribose polymerase 1 inhibitors (PARPi) has created an astonishing clinical excitement in breast cancer and ovarian cancer treatment by discovering that it can specifically kill HR repair-deficient cancer cells, such as tumors with germline BRCA1/BRCA2 mutations, via a synthetic lethality interaction between HR deficiency and inhibition of PARP activity by PARPi. Because it is a synthetic lethality interaction, the clinical success of PARPi is dependent on identifying the right patients with HR repair-deficient tumors for this targeted therapy. Thereby, the major clinical challenge is to develop a clinically applicable tool to identify HR repair-defects in cancer cells. Clinically it is virtually impossible to identify every HR repair gene defect in patient tumors to select patients for PARPi. The HRD gene signature provides a clinically applicable tool to identify patients who should be treated with PARPi and who can be mostly benefited by this new class of anti-cancer drugs, which will lead to a more personalized approach for cancer patient treatment.

While the immediate application of the technology is in identifying patients likely to benefit from PARPi, there are multiple other uses. First the signature could be used to identify patients who will benefit from other forms of therapy that are dependent on HR function. For example, platin analogs are more effective in patients and tumor cell lines with defects in HR repair. Similarly, the signature could be used to identify drugs that induce HR repair defects and could also act as a synthetic lethal effect with PARPi.

The HRD gene signature provides the following competitive advantages relative to existing technology: 1) it generates quicker results than sequencing of all aberrations of HR repair genes in tumor samples. 2) Immunohistochemistry staining (IHC) can only measure the total level of HR repair genes, which cannot measure the functional defects of these genes in response to DNA damage. 3) RAD51 foci fluorescent staining is the most common method to detect functional HR repair defects. However it requires fresh tumor samples and pre-treatment of DNA damage stimuli, which is not a clinically applicable tool.

The HRD gene signature provides a functional gene signature representing the HR repair defects. It measures a common biological effect of HR deficiency. It will the identification of HR repair defects at the functional level without knowing the specific genetic aberrations that might alter HR repair in tumors. The robust and reproducibility of the gene signature provides a solid foundation to apply the HRD gene signature as a functional prediction tool of HR repair defects.

I. Aspects of the Present Invention

A Network View of HR Repair. Cells have evolved a complex DNA damage repair system, HR repair, which plays a fundamental role in maintaining genomic integrity and preventing tumorigenesis. Given the enormous complexity of HR repair, identifying dysfunctional HR repair in human cancers is an enormous challenge. Instead of examining individual genes involved in HR repair, in this study, gene expression profiling was used to provide a global network view of the consequences of defective HR-deficiency. The HRD gene signature allows interrogation of the status of HR repair by simultaneously considering hundreds of genes and thereby allows identification of dysfunctional HR repair in a given cellular state independent of underlying mechanism. The data suggest that HR repair components are not independent. Instead, they form a network that is responsible for the integrated HR repair capacity of cells. Given the complexity of the HR repair network, the HRD gene signature allows interrogation of the status of HR repair by simultaneously considering hundreds of genes and thereby allows identification of HR-deficiency in a given cellular state independent of underlying mechanism.

Consistent with a previous study involving synthetic lethality analysis in yeast (Pan et al., 2006), the results presented herein show that DNA replication, DNA metabolism, and DNA damage response signaling pathways coordinating DNA repair with cell cycle progression are interconnected biological processes. In addition to identifying many genes known to be involved in these biological processes, the HRD gene signature reveals new components and pathways that may interact with HR repair in genome maintenance. For example, the study uncovered previously unknown functions of ZNF668 and TTK in HR repair and showed that mTOR may play a role in integrating metabolic signaling with DNA repair.

A Molecular Predictor of HR Repair Deficiency. Because of the complexity of the HR repair network, a gene signature was used as a molecular predictor of HR repair deficiency, which allowed assessment of HR repair capacity without examining genetic alterations in individual HR repair components. It is notable that another group similarly used gene expression profiling to generate a "BRCAness" signature (Konstantinopoulos et al., 2010). These authors compared gene expression profiles of ovarian tumors with BRCA1/2 germline mutations and ovarian tumors without either mutation. They then used genome wide hierarchical clustering to define BRCA-like and non-BRCA-like tumors, which generated a subset of optimal classifiers (60 genes). As shown in the present study and previous reports, BRCA1/2-mutated tumors may not necessarily be HR-deficient because mutations in other genes can reverse HR-deficiency through loss of PTEN or 53BP1 or by reversion of BRCA1/2 mutation (Bunting et al., 2010; Bouwman et al., 2010; Swisher et al., 2008; Edwards et al., 2008). Therefore, a gene signature generated from germline BRCA1/2-mutated ovarian cancers is not inextricably linked to HR repair deficiency. In contrast, the HRD gene signature was generated from a well-defined cellular system with acute induction of HR repair deficiency. Having been validated by testing genes known and not known to be involved in HR repair that the HRD gene signature is functionally linked to HR repair deficiency, it was further showed that cancer cell sensitivity to PARP inhibitor treatment could be predicted by determining whether their gene expression profiles were similar to the HRD gene signature. In addition, the HRD gene signature correlated with clinical outcomes in multiple human cancers. Thus, the HRD gene signature can be applied to a complex genetic background in cancer cells.

In addition to biological insights, the HRD gene signature can be used as a potential prognostic tool for cancer patient outcome. Furthermore, the HRD gene signature has potential therapeutic implication. One of the recent most exciting therapeutic breakthroughs in cancer is the identification of a synthetic lethal interaction between HR-deficiency and PARP inhibitors (Bryant et al., 205; Farmer et al., 2005). As a targeted therapeutic, the implementation of PARP inhibitors into patient management thus largely depends on accurate identification of patients with HR-deficient tumors as well as on approaches to prevent the emergence of resistance. The advantage of this HRD gene signature as an assessment of HR deficiency without interrogating individual genetic alterations in cancer may allow the development of practical and effective companion diagnostics able to robustly identify patients likely to benefit from PARP inhibitors beyond those with BRCA1/2 defect.

It would be of great interest to test whether the HRD gene signature could be used to predict PARP inhibitor sensitivity in the clinic, identifying patients most likely to benefit from this treatment and sparing those who are unlikely to respond from the expense and side effects of PARP inhibitor treatment and potential delays in implementing other effective therapies. In addition, because the HRD gene signature reflects the overall status of the HR repair network, not just HR repair status in cancers with BRCA1/2 mutations, confirmation that the HRD gene signature is clinically useful could broaden the application of PARP inhibitors to treatment of HR-repair-deficient tumors in general, not just BRCA1/2-mutated cancers.

Rewiring of the HR Repair Network in Cancer. The HR repair network is not static but rather dynamic during tumor evolution, which can be extensively rewired during tumor progression. HR repair deficiency leads to genomic instability and predisposes to cancer development, such as germline mutations of BRCA1/2 leading to breast and ovarian cancers. During tumorigenesis, HR repair deficiency may precipitate secondary genetic alterations, such as loss of 53BP1, which can rewire the HR repair network and reverse HR repair deficiency (Bouwman et al., 2010; Bunting et al., 2010). The present results further support the notion that the HR repair network can be extensively rewired during tumor progression. By using gene signature analysis, it was found that although HCC1937 and MDA-MB-436 breast cancer cell lines contain BRCA1 mutations, they did not exhibit HR repair deficiency and sensitivity to PARP inhibitor treatment. The underlying mechanism could be that co-existing loss of PTEN in BRCA1-deficient cells reverses HR repair by regulating key genes involved in HR, such as TTK. The present study reveals that the combined effects of co-mutations/co-genetic alterations in cancer cells could be more determinative than the effects of individual alterations in terms of the molecular behavior of cancer cells. The phenotypes may not be the simple sum of each genetic change in cancer cells. With the advent of next-generation sequencing, it may be possible to catalogue all the individual genetic alterations in a given tumor sample. However, to decipher the overall impact of these genetic alterations will likely require analyses of functional networks, which are perturbed by these genetic alterations from a systems biology level, instead of dissection of the functions of individual genetic alterations independently.

Druggable Targets for Combating Resistance to PARP Inhibitor Treatment. Intrinsic resistance and the development of acquired resistance in the metastatic setting have both been observed in clinical trials of PARP inhibitors in BRCA1/2 mutation carriers (Maxwell and Domchek, 2012). In the present study, analysis of the HR repair network by gene expression profiling allowed the identification of potential resistance mechanisms and druggable targets to increase PARP sensitivity and potentially to counteract PARP inhibitor resistance. Chemical inhibitors of TTK, mTOR, and PI3K could increase PARP inhibitor sensitivity and potentially extend the spectrum of tumors that would benefit from synthetic lethality beyond those with BRCA1/2 defects or intrinsic HR deficiency. Combining TTK or mTOR inhibitors with PARP inhibitor could also be a promising approach to improve responses to PARP inhibitor treatment.

Recent clinical trials of PARP inhibitors have shown a poor response rate (Audeh et al., 2010; Fong et al., 2009; Gelmon et al., 2011) in BRCA1/2-deficient cancer patients, suggesting that only a portion of patients with BRCA1/2 mutations respond and unfortunately responses are usually short-lived. In the present study, analysis of the HR repair network by gene expression profiling allowed us to identify chemicals targeting HR repair process. These findings suggest that combining TTK, mTOR, PI3K, HDAC, or Hsp90 inhibitors with PARP inhibitors could also be promising approaches to improve responses to PARP inhibitor treatment, or more generally to DNA damage-inducing treatment, such as radiation therapy and chemotherapy with cisplatin. A recent study showed that PARP-1 inhibition leads to activation of mTORC1 complex due to reduced AMPK activity (Zhou et al., 2013). This result together with the present findings strongly suggest that the therapeutic benefit of combining PARP inhibitor with mTOR inhibitor may be mediated by targeting both HR repair pathway and the PARP inhibitor-induced suppression of AMPK pathway.

II. Methods of Treating

Certain aspects of the present invention can be used to identify and/or treat a disease or disorder based on the presence of a homologous recombination (HR) repair defect (HRD) as identified by the presence of an HRD gene signature. Other aspects of the present invention provide for sensitizing a subject with cancer to treatment with PARP inhibitors.

The term "subject" or "patient" as used herein refers to any individual to which the subject methods are performed. Generally the patient is human, although as will be appreciated by those in the art, the patient may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of patient.

"Treatment" and "treating" refer to administration or application of a therapeutic agent to a subject or performance of a procedure or modality on a subject for the purpose of obtaining a therapeutic benefit of a disease or health-related condition. For example, a treatment may include administration chemotherapy, immunotherapy, radiotherapy, performance of surgery, or any combination thereof.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the invasiveness of a tumor, reduction in the growth rate of the cancer, or prevention of metastasis. Treatment of cancer may also refer to prolonging survival of a subject with cancer.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect. A tissue, tumor, or cell can be contacted with one or more compositions or pharmacological formulation(s) comprising one or more of the agents, or by contacting the tissue, tumor, and/or cell with two or more distinct compositions or formulations. Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

The methods described herein are useful in treating cancer, particularly, HR repair deficient cancer. Generally, the terms "cancer" and "cancerous" refer to or describe the physiological condition in mammals that is typically characterized by unregulated cell growth. More specifically, cancers that are treated using any one or more PARP inhibitors, or variants thereof, and in connection with the methods provided herein include, but are not limited to, carcinoma, lymphoma, blastoma, sarcoma, leukemia, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer and gastrointestinal stromal cancer), pancreatic cancer, glioblastoma, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, melanoma, superficial spreading melanoma, lentigo maligna melanoma, acral lentiginous melanomas, nodular melanomas, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

An effective response of a patient or a patient's "responsiveness" to treatment refers to the clinical or therapeutic benefit imparted to a patient at risk for, or suffering from, a disease or disorder. Such benefit may include cellular or biological responses, a complete response, a partial response, a stable disease (without progression or relapse), or a response with a later relapse. For example, an effective response can be reduced tumor size or progression-free survival in a patient diagnosed with cancer.

Poly(ADP-ribose)polymerase has an essential role in facilitating DNA repair, controlling RNA transcription, mediating cell death, and regulating immune response. PARP inhibitors are a group of pharmacological inhibitors of the enzyme PARP. In various preclinical cancer models and human clinical trials, PARP inhibitors have been shown to potentiate radiation and chemotherapy by increasing apoptosis of cancer cells, limiting tumor growth, decreasing metastasis, and prolonging the survival of tumor-bearing subjects. (WO 2007/084532; Donawho et al., 2007; Kummar et al., 2009). By way of example, PARP inhibitors include, but are not limited to, olaparib (AZD-2281), veliparib (ABT-888), iniparib (BSI-201), rucaparib (AG014699, PF-01367338), AG14361, INO-1001, A-966492, PJ34, MK-4827, CEP 9722, BNM-673, 3-aminobenzamide, and those disclosed in U.S. Pat. Nos. 7,928,105; 8,124,606; 8,236,802; 8,450,323; WO 2006/110816; WO 2008/083027; and WO 2011/014681.

TTK, a dual serine-threonine kinase involved in mitotic spindle assembly checkpoint, is encoded by the human protein kinase monopolar spindle 1 (hMps1/TTK) gene. By way of example, TTK inhibitors include, but are not limited to, MPI-0479605, AZ3146, and those disclosed in US2003/0045491; US2011/0002923; WO 2009/024824; WO2010/007756; WO 2011/064328; WO 2011/063907; and WO 2011/063908.

Mammalian target of rapamycin (mTOR) is a serine/threonine kinase, which belongs to the phosphatidylinositol-3 kinase (PI3K) related kinases (PIKKs) family. It regulates cellular metabolism, growth, and proliferation. An mTOR inhibitor may be an allosteric or catalytic inhibitor. By way of example, mTOR inhibitors include, but are not limited to, OSI-027, rapamycin, sirolimus, deforolimus (AP23573), everolimus (RAD001), temsirolimus (CCI-779), INK128; OXA-01 (OSI-950), PP-242, PP-30, AZD2014; AZD8055, INK-128, Torin-1, WYE-132, GSK-2126458, and those disclosed in US 2007/0112005; US 2010/0048547; WO2010/006072; US 2009/0312319; US 2010/0015140; US 2007/0254883; US 2007/0149521.

A Phosphoinositide 3-kinase inhibitor (PI3K inhibitor) is a drug that functions by inhibiting a PI3K, which, through inhibition, often results in tumor suppression. By way of example, PI3K inhibitors include, but are not limited to LY-294002, wortmannin, BKM120, demethoxyviridin, perifosine; PX-866; IPI-145; BAY 80-6946; idelalisib; BEZ235; BYL 719; RP6530; TGR 1202; INK1117; GDC-0941; GDC-0980; XL147; XL765; palomid 529; GSK1059615; ZSTK474; PWT33597; IC87114; TG100-115; CAL263; RP6503; PI-103; GNE-477; CUDC-907; AEZS-136 and those disclosed in U.S. Pat. No. 8,586,574; WO 2012/082997 and WO 2014/005182.

Regarding neoplastic condition treatment, depending on the stage of the neoplastic condition, neoplastic condition treatment involves one or a combination of the following therapies: surgery to remove the neoplastic tissue, radiation therapy, and chemotherapy. Other therapeutic regimens may be combined with the administration of the anticancer agents, e.g., therapeutic compositions and chemotherapeutic agents. For example, the patient to be treated with such anti-cancer agents may also receive radiation therapy and/or may undergo surgery.

For the prevention or treatment of disease, the appropriate dosage of a therapeutic composition, e.g., a PARD inhibitor, will depend on the type of disease to be treated, as defined above, the severity and course of the disease, whether the agent is administered for preventive or therapeutic purposes, previous therapy, the patient's clinical history and response to the agent, and the discretion of the physician. The agent is suitably administered to the patient at one time or over a series of treatments.

A. Combination Treatments

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. A tissue, tumor, or cell can be contacted with one or more compositions or pharmacological formulation(s) comprising one or more of the agents or by contacting the tissue, tumor, and/or cell with two or more distinct compositions or formulations. Also, it is contemplated that such a combination therapy can be used in conjunction with radiotherapy, surgical therapy, or immunotherapy.

Administration in combination can include simultaneous administration of two or more agents in the same dosage form, simultaneous administration in separate dosage forms, and separate administration. That is, the subject therapeutic composition and another therapeutic agent can be formulated together in the same dosage form and administered simultaneously. Alternatively, subject therapeutic composition and another therapeutic agent can be simultaneously administered, wherein both the agents are present in separate formulations. In another alternative, the therapeutic agent can be administered just followed by the other therapeutic agent or vice versa. In the separate administration protocol, the subject therapeutic composition and another therapeutic agent may be administered a few minutes apart, or a few hours apart, or a few days apart.

An anti-cancer first treatment may be administered before, during, after, or in various combinations relative to a second anti-cancer treatment. The administrations may be in intervals ranging from concurrently to minutes to days to weeks. In embodiments where the first treatment is provided to a patient separately from the second treatment, one would generally ensure that a significant period of time did not expire between the time of each delivery, such that the two compounds would still be able to exert an advantageously combined effect on the patient. In such instances, it is contemplated that one may provide a patient with the first therapy and the second therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below an antibody therapy is "A" and an anti-cancer therapy is "B":

| | | | | | |
|---|---|---|---|---|---|
| A/B/A | B/A/B | B/B/A | A/A/B | A/B/B | B/A/A |
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

Administration of any compound or therapy of the present invention to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the invention. In the context of cancer treatment, immunotherapeutics, generally, rely on the use of immune effector cells and molecules to target and destroy cancer cells. Rituximab (Rituxan®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present invention, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present invention to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present invention to improve the anti-hyperproliferative efficacy of the treatments Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present invention to improve the treatment efficacy.

III. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

A Robust Gene Signature Predicting Deficient Homologous Recombination DNA Repair HR repair involves a variety of proteins that detect, signal, and repair DSBs (Moynahan and Jasin, 2010; San Filippo et al., 2008). Repair of DSBs is initiated by resection of the 5' strands that generates 3' single-stranded DNA tails at the DSB ends. DSB end resection facilitated by BRCA1 allows loading of single-strand binding protein RPA (Yun and Hiom, 2009). RPA is then replaced by key enzyme RAD51 with the help of BRCA2, which mediates homology search and restores damaged DNA (Jensen et al., 2010; Yun and Hiom, 2009). The HR repair process is coordinated by many cellular responses, such as cell cycle checkpoint, transcriptional activation, epigenetic regulation, and various posttranslational modifications (Ciccia and Elledge, 2010; Helleday et al., 2008; Huen and Chen, 2008; Jackson and Bartek, 2009; Lukas et al., 2011). The number of genes known to be involved in HR repair is constantly expanding with recent genome-wide surveys of HR repair proteins using RNA interference revealing hundreds of genes involved in HR repair (Adamson et al., 2012; Slabicki et al., 2010), dysfunction of any of which may lead to altered HR repair. As such, it would be virtually impossible to use conventional single-gene approaches (e.g., immunohistochemical staining or mutation sequencing) to identify every possible genetic alteration that might lead to HR repair deficiency.

Therefore, a transcriptional profiling-based approach was implemented to systematically identify common molecular changes associated with defective HR repair and generate an HRD gene signature. Then, the clinical relevance of the HRD gene signature was explored in multiple independent patient datasets and it was found that it robustly predicted clinical outcome across tumor lineages. It was further validated that the HRD gene signature predicted HR status and sensitivity to PARP inhibitors in human cancer cells. More important, the HRD gene signature was able to be used to identify mechanisms underlying resistance to PARP inhibitors and identify rational combination therapies predicted to synergize with PARP inhibitors. The clinical relevance of the HRD gene signature was also explored in multiple independent patient datasets and it was found that it correlated with overall survival across tumor lineages. In summary, a gene signature was identified, which can be used both to predict defective HRD repair and clinical outcome in cancer patients.

Figure 6A:
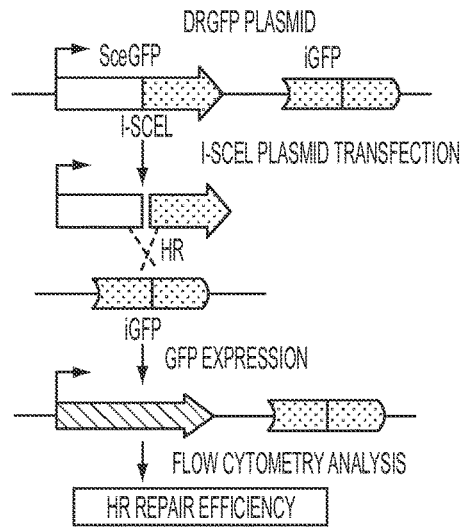
FIGS. 6A-C. Establish HRD cell lines to generate "the HRD gene signature." (A) Schematic diagram of HR repair assay. The DRGFP reporter substrate was integrated into cellular genomic DNA. SceGFP contains an I-SceI endonuclease site within the coding region, which abolishes GFP expression. iGFP is a truncated GFP, which contains homologous sequence for the SceGFP. Expression of I-SceI induces a single DSB in the genome. When this DSB is repaired by HR, the expression of GFP can be restored and analyzed by flow cytometry to indicate the efficiency of HR repair. (B) MCF-10A cells were infected with lentiviral particles targeting BRCA1, RAD51 or BRIT1. Cells were selected in puromycin (1 µg/mL) for 10-15 days. Selected stable clones were subject to HR repair assay as described above. Each value is relative to the percentage of GFP-positive (GFP+) cells in I-SceI-transfected control cells.
Figure 6B:
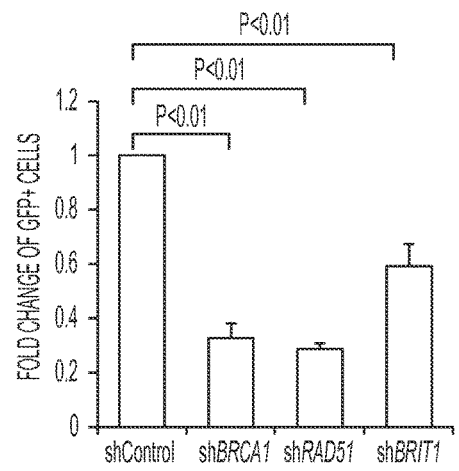
Figure 6C:
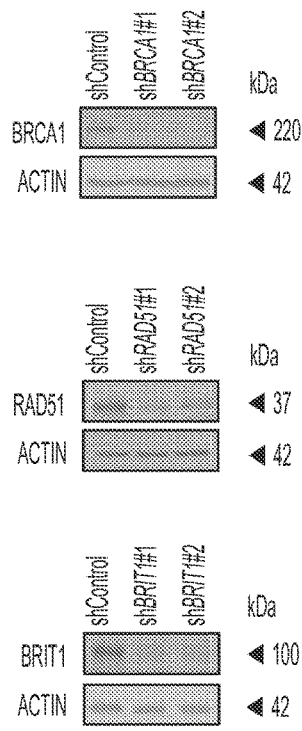
Figure 6C:
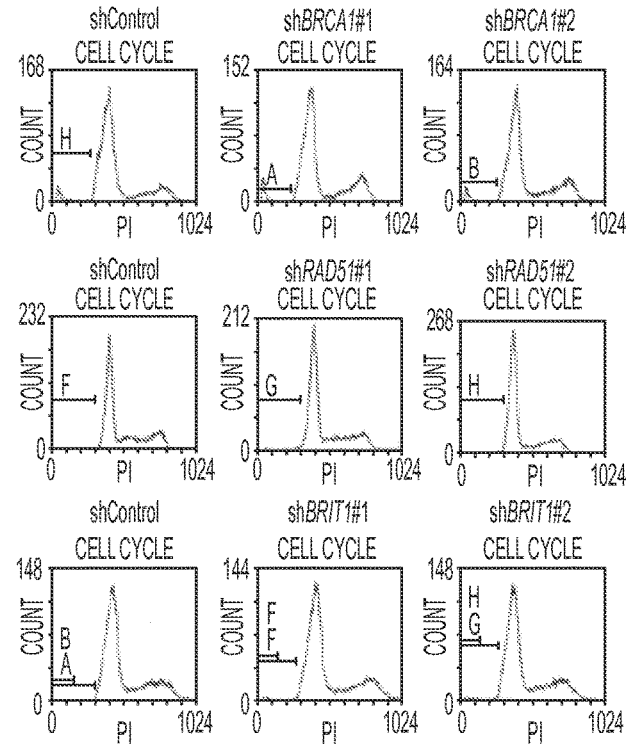

Identification of an HRD Gene Signature. To obtain a comprehensive molecular understanding of the HR repair process, rather than taking a single gene approach to analyze HR repair in cells, a genome-wide gene expression profiling approach was used to systematically measure the cellular transcriptome reprogramming in HR-deficient cells. Normal breast epithelial MCF-10A cells, an immortal human mammary epithelial cell line of nonmalignant origin, were used to establish isogenic cell lines with deficiency individually in three independent HR repair genes: BRCA1, RAD51, and BRIT1 (MCPH1). These genes were chosen due to their regulating of HR repair at different steps via distinct mechanisms. BRCA1 plays a critical role in DNA damage response and the initial step of HR repair, DSB end resection (Moynahan and Jasin, 2010; Yun and Hiom, 2009). RAD51 is the key recombinase enzyme for homologous sequence searching and recombination (Jensen et al., 2010; Sonoda et al., 1998). BRIT1 mediates HR repair, likely through regulating chromatin structure and facilitating loading of DNA repair proteins (Peng et al., 2009; Wood et al., 2008). As expected, the cell lines with deficiency in BRCA1, RAD51, and BRIT1 had significantly reduced HR repair efficiency (FIG. 6B) and greatly increased cellular sensitivity to PARP inhibitors compared to parental vector transfected cells (FIG. 11A). Importantly, all the knockdown cell lines exhibited cell cycle distribution similar to that of the control cells (FIG. 6C), which excluded effects caused by changes in cell cycle progression.

Figure 1A:
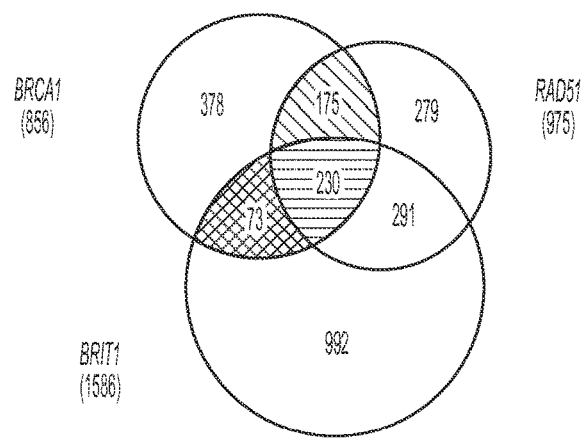
FIGS. 1A-B. Gene Expression Analysis Identifies an HRD Gene Signature that Functionally Predicts the Status of HR Repair Deficiency. (A) (Left) Venn diagram indicating numbers of genes whose expression differed between each HRD cell line and the other HRD cell lines and the control cells. The analysis was performed using BRB-ArrayTools. (B) U2OS cells were transfected with ZNF668 siRNA or control siRNA and analyzed for HR repair efficiency. The HR repair efficiency of I-SceI-induced DSBs was measured by flow cytometry analysis of GFP-positive cells. Each value is relative to the percentage of GFP-positive cells in I-SceI-transfected control cells. Results are show as mean±SD from three independent experiments; Student's t-test was used to test statistical significance. Western blots demonstrating effective knockdown are shown to the upper right and cell cycle analysis with propidium iodide staining performed seventy-two hours after transfection are shown to the lower right.
Figure 1B:
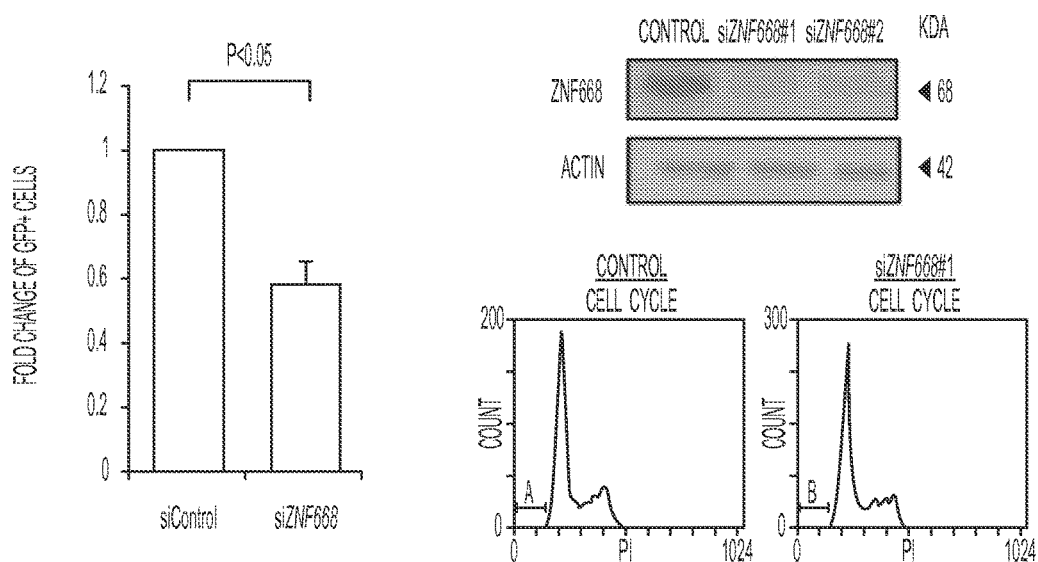

Microarrays were conducted in 7 independent samples of control cells and 4 independent samples of each individual knockdown cell line. Microarray analyses were then used to search for genes differentially expressed between control and HRD cell lines. A set of 230 genes (listed in Table 2) whose expression differed by a factor of 2 or more (P<0.001 by Student's t-test) between each of the HRD cell lines and control cells were selected and designated the HRD gene signature. Importantly, expression of these genes is coordinately upregulated or downregulated in cell lines with HRD induced by independent HR genes that have different mechanisms of action (FIG. 1A).

As expected, a high proportion of genes in the HRD gene signature were involved in cell cycle regulation, DNA replication, and DNA recombination and repair pathways (Table 1). In addition, a high proportion of genes in the HRD gene signature were in canonical pathways involved in mismatch repair, the function of BRCA1 and CHK proteins in DNA damage response, and cell cycle checkpoint control (Table 1).

TABLE 1

Gene-set enrichment analysis by Ingenuity program.

Molecular and Cellular Functions

| Name | p-value | # Molecules |
|---|---|---|
| Cell Cycle | 6.87E–13-1.94E–02 | 68 |
| DNA Replication, Recombination, and Repair | 2.06E–11-1.74E–02 | 69 |
| Cellular Assembly and Organization | 8.93E–10-1.73E–02 | 46 |
| Cellular Function and Maintenance | 1.24E–07-1.94E–02 | 28 |
| Cell Death | 7.87E–04-1.94E–02 | 79 |

Top Canonical Pathways

| Name | p-value | Ratio |
|---|---|---|
| Mismatch Repair in Eukaryotes | 7.92E–14 | 9/24 (0.375) |
| Role of BRCA1 in DNA Damage Response | 6.30E–08 | 9/65 (0.138) |
| Hereditary Breast Cancer Signaling | 2.13E–06 | 10/127 (0.079) |
| Role of CHK Proteins in Cell Cycle Checkpoint Control | 5.29E–06 | 7/56 (0.125) |
| Pyrimidine Metabolism | 1.17E–05 | 10/215 (0.047) |

Importantly, expression of these genes was coordinately up-regulated or down-regulated in cells with HR-deficiency induced by depletion of independent HR genes that have different mechanisms of action (Table 2). For example, the expression levels of three DSB end resection enzymes, BLM, DNA2, and EXO1, were all markedly reduced in HR-deficient cells, indicating DSB end resection efficiency would be expected to be correspondingly reduced by transcriptional regulation of resection enzymes. This observation showed that HR-deficiency, independent of the specific mediator, leads to similar transcriptional changes. Thus, in cells with deficiency in other components of HR repair, such as BRCA1 and RAD51, DSB end resection efficiency would be expected to be correspondingly reduced by transcriptional regulation of resection enzymes. To exclude the possibility that the HRD gene signature is the result of cellular transcriptome reprogramming during stable selection, further transient transfection of BRCA1 siRNA in MCF10A cells was conducted and microarray analysis performed to verify accuracy and specificity of the HRD gene signature. Using supervised clustering analysis, we demonstrated that knocking down BRCA1 by siRNA in MCF10A (FIG. 8) also led to the HRD gene signature. All these findings strongly suggest that the molecular components involved in HR repair are interconnected and increase the likelihood that the HRD gene signature will capture defects in HR repair independent of the underlying mediator. This result further supports the contention that the HRD gene signature could allow for interrogation of the status of HR repair deficiency induced by multiple different mechanisms.

TABLE 2

List of 230 HR genes.

| UniqID | Symbol | BRCA1/Control | Rad51/Control | BRIT1/Control |
|---|---|---|---|---|
| Table 2A - Genes with reduced expression | | | | |
| ILMN_1769388 | GJB2 | 0.13778637 | 0.174157773 | 0.197887008 |
| ILMN_1738027 | BRCA1 | 0.158563144 | 0.307140816 | 0.25875128 |
| ILMN_1715401 | MT1G | 0.159370727 | 0.079830027 | 0.373634708 |
| ILMN_1737184 | CDCA7 | 0.169231795 | 0.113149704 | 0.149774939 |
| ILMN_1730794 | SERTAD4 | 0.18207468 | 0.193247708 | 0.273485421 |
| ILMN_1663195 | MCM7 | 0.188847528 | 0.221608234 | 0.400174601 |
| ILMN_1774336 | POLE2 | 0.198641319 | 0.149833983 | 0.214157747 |
| ILMN_1776577 | DCC1 | 0.206451446 | 0.161108091 | 0.200721172 |
| ILMN_1677765 | LRP8 | 0.2119 | 0.161517705 | 0.11377922 |
| ILMN_1739645 | ANLN | 0.220233364 | 0.323484705 | 0.208461603 |
| ILMN_1772131 | IL1R2 | 0.225339229 | 0.182284339 | 0.406780327 |
| ILMN_1786065 | UHRF1 | 0.227961697 | 0.169696234 | 0.176490453 |
| ILMN_1761322 | FHOD3 | 0.213409863 | 0.286505481 | 0.287331079 |
| ILMN_1806818 | MCM3 | 0.228162447 | 0.293029488 | 0.280171156 |
| ILMN_1814281 | SPC25 | 0.233682075 | 0.191563171 | 0.255831346 |
| ILMN_1777233 | E2F2 | 0.230691242 | 0.202943728 | 0.244206305 |
| ILMN_1658027 | RAD54L | 0.247156598 | 0.214165498 | 0.294672815 |
| ILMN_1667825 | MLKL | 0.240197193 | 0.194387917 | 0.308172247 |
| ILMN_1681503 | MCM2 | 0.26377616 | 0.24873919 | 0.466051283 |
| ILMN_1809590 | GINS2 | 0.265087383 | 0.136268471 | 0.199445581 |
| ILMN_1733519 | HMGB3 | 0.267665767 | 0.354663089 | 0.331624044 |
| ILMN_1741801 | CDC7 | 0.272959484 | 0.308105119 | 0.277675657 |
| ILMN_1754272 | GINS3 | 0.279368216 | 0.294180907 | 0.40781609 |
| ILMN_1652580 | POLD1 | 0.284141798 | 0.31499608 | 0.46657568 |
| ILMN_1749829 | DLG7 | 0.282026557 | 0.189652897 | 0.326482387 |
| ILMN_1732688 | DUT | 0.279152938 | 0.322002496 | 0.300012948 |
| ILMN_1693410 | BRI3BP | 0.284146678 | 0.251749729 | 0.201364129 |
| ILMN_1772869 | C20orf82 | 0.282047868 | 0.388623477 | 0.43533254 |
| ILMN_1659364 | RFC5 | 0.288510894 | 0.276698012 | 0.39454717 |
| ILMN_1673721 | EXO1 | 0.283496273 | 0.214511063 | 0.210743816 |
| ILMN_1695414 | ASF1B | 0.287942058 | 0.271904934 | 0.423418935 |
| ILMN_1782813 | DHFR | 0.281528978 | 0.278337826 | 0.29366923 |
| ILMN_1799106 | MOSC1 | 0.283870844 | 0.258415955 | 0.415193499 |
| ILMN_1703617 | AHSA1 | 0.291138066 | 0.461385918 | 0.296262701 |
| ILMN_1683450 | CDCA5 | 0.298787966 | 0.205763154 | 0.474861479 |
| ILMN_1770044 | CHRNA5 | 0.292676616 | 0.274383065 | 0.326525378 |
| ILMN_1737728 | CDCA3 | 0.306614829 | 0.249790154 | 0.376917804 |
| ILMN_1806040 | TYMS | 0.306860622 | 0.338928211 | 0.390962898 |
| ILMN_1678669 | RRM2 | 0.293807027 | 0.177435017 | 0.167233833 |
| ILMN_1661776 | CENPJ | 0.310824975 | 0.328384339 | 0.419963352 |
| ILMN_1792947 | ESCO2 | 0.313473636 | 0.267124278 | 0.227313281 |
| ILMN_1696347 | CTSC | 0.319021588 | 0.476264527 | 0.373915789 |
| ILMN_1696713 | POLA2 | 0.32127739 | 0.236700726 | 0.270346496 |
| ILMN_1729051 | MSH6 | 0.328747507 | 0.367575223 | 0.387901586 |
| ILMN_1747303 | DDX39 | 0.331798817 | 0.340884494 | 0.429237287 |
| ILMN_1726114 | SLC45A3 | 0.324061764 | 0.251845416 | 0.347337365 |
| ILMN_1740291 | POLQ | 0.330791018 | 0.295203328 | 0.236022922 |
| ILMN_1786125 | CCNA2 | 0.332440562 | 0.253578188 | 0.213349768 |
| ILMN_1668012 | SLC25A13 | 0.3253731 | 0.318201406 | 0.305206171 |
| ILMN_1694177 | PCNA | 0.340403373 | 0.497534609 | 0.270480217 |
| ILMN_1806037 | TK1 | 0.342473588 | 0.199722221 | 0.367366618 |
| ILMN_1795852 | CCNE1 | 0.343650087 | 0.350316184 | 0.419104484 |
| ILMN_1679438 | MLF1IP | 0.346703192 | 0.316591946 | 0.424337986 |
| ILMN_1796589 | TRIP13 | 0.347862987 | 0.212376632 | 0.254101143 |
| ILMN_1709484 | BLM | 0.348773858 | 0.324850004 | 0.34527865 |
| ILMN_1755834 | FEN1 | 0.334630816 | 0.253618062 | 0.206682803 |
| ILMN_1728934 | PRC1 | 0.352953919 | 0.279680521 | 0.490738832 |
| ILMN_1804248 | FDPS | 0.353597022 | 0.391265546 | 0.364043512 |
| ILMN_1815169 | MCM5 | 0.361122949 | 0.193870402 | 0.376173673 |
| ILMN_1807501 | GINS4 | 0.34992914 | 0.254662123 | 0.397590206 |
| ILMN_1737413 | MSH2 | 0.354612642 | 0.447705808 | 0.364330801 |
| ILMN_1683441 | NCAPD3 | 0.364830202 | 0.363006721 | 0.319214047 |
| ILMN_1693669 | WDR79 | 0.364409741 | 0.36745668 | 0.427644086 |
| ILMN_1664682 | DNA2L | 0.356982629 | 0.437391638 | 0.332038826 |
| ILMN_1655642 | FANCI | 0.362953568 | 0.255292986 | 0.27714391 |
| ILMN_1781943 | FAM83D | 0.369533225 | 0.387770227 | 0.356804634 |
| ILMN_1703324 | PDSS1 | 0.370073998 | 0.408470374 | 0.240810306 |
| ILMN_1664630 | CHEK1 | 0.372374773 | 0.331214111 | 0.386067868 |
| ILMN_1722127 | RAD54B | 0.367827083 | 0.432305457 | 0.409954771 |
| ILMN_1729288 | C1QTNF6 | 0.371633949 | 0.472534482 | 0.467885864 |
| ILMN_1794539 | KIF11 | 0.378590319 | 0.370572868 | 0.441673691 |
| ILMN_1804090 | SLC25A10 | 0.366757353 | 0.413663231 | 0.385938871 |
| ILMN_1669842 | CHAF1A | 0.37843314 | 0.279655253 | 0.336662265 |
| ILMN_1780769 | TUBB2C | 0.379517932 | 0.310280945 | 0.276899674 |

TABLE 2-continued

List of 230 HR genes.

| UniqID | Symbol | BRCA1/Control | Rad51/Control | BRIT1/Control |
|---|---|---|---|---|
| ILMN_1656452 | C16orf59 | 0.387077719 | 0.308330282 | 0.348590363 |
| ILMN_1720266 | LOC91431 | 0.385916163 | 0.402322811 | 0.366862555 |
| ILMN_1793474 | INSIG1 | 0.381245218 | 0.439011773 | 0.334432531 |
| ILMN_1696407 | SFRS2 | 0.390532688 | 0.424946817 | 0.316329318 |
| ILMN_1655635 | METTL3 | 0.385454605 | 0.430111683 | 0.412052777 |
| ILMN_1674231 | CHAF1B | 0.385398925 | 0.299616787 | 0.301179025 |
| ILMN_1759277 | OIP5 | 0.394631063 | 0.310541835 | 0.434913387 |
| ILMN_1811470 | PLEK2 | 0.385948815 | 0.13807659 | 0.253868122 |
| ILMN_1762275 | CSE1L | 0.394431066 | 0.441932337 | 0.271888069 |
| ILMN_1673673 | PBK | 0.383136451 | 0.435281366 | 0.240156165 |
| ILMN_1792455 | TMEM158 | 0.371872199 | 0.367480038 | 0.194658041 |
| ILMN_1803775 | HSPE1 | 0.390678428 | 0.469749214 | 0.41326361 |
| ILMN_1674662 | C15orf42 | 0.40006462 | 0.354142825 | 0.467109046 |
| ILMN_1784860 | RFC3 | 0.398641422 | 0.286821323 | 0.241213108 |
| ILMN_1684217 | AURKB | 0.402971907 | 0.242753108 | 0.401651106 |
| ILMN_1676036 | LOC649679 | 0.395338751 | 0.336174548 | 0.255523906 |
| ILMN_1703906 | DKFZp762E1312 | 0.400595072 | 0.342230576 | 0.329481242 |
| ILMN_1783610 | HELLS | 0.403845101 | 0.337962329 | 0.28088811 |
| ILMN_1660793 | PAQR4 | 0.403637533 | 0.245923791 | 0.325099965 |
| ILMN_1808071 | KIF14 | 0.410810049 | 0.302687355 | 0.250165238 |
| ILMN_1757697 | NEIL3 | 0.400829876 | 0.316569365 | 0.340233684 |
| ILMN_1810901 | RNASEH2A | 0.413995749 | 0.29363356 | 0.462917657 |
| ILMN_1724407 | TACC3 | 0.408404594 | 0.26775563 | 0.406554646 |
| ILMN_1784300 | TUBA4A | 0.412249298 | 0.392498538 | 0.299658729 |
| ILMN_1685916 | KIF2C | 0.418667418 | 0.323762647 | 0.448261475 |
| ILMN_1767260 | CCDC138 | 0.419424514 | 0.385597836 | 0.430872244 |
| ILMN_1732516 | KNTC1 | 0.424654967 | 0.443964634 | 0.413041207 |
| ILMN_1684802 | TAF5 | 0.425569854 | 0.377222293 | 0.479227521 |
| ILMN_1781479 | SUV39H1 | 0.423203551 | 0.318140151 | 0.432156373 |
| ILMN_1727540 | C1orf112 | 0.420918188 | 0.262825244 | 0.324277978 |
| ILMN_1801664 | POLR3K | 0.422497011 | 0.30762982 | 0.217136309 |
| ILMN_1805828 | VRK1 | 0.423989177 | 0.313617272 | 0.338598343 |
| ILMN_1788166 | TTK | 0.426424331 | 0.268271092 | 0.31057514 |
| ILMN_1703092 | RECQL4 | 0.428574832 | 0.406628583 | 0.43317599 |
| ILMN_1736441 | PDXP | 0.431043682 | 0.456179259 | 0.263717857 |
| ILMN_1750100 | TUBB4Q | 0.423296897 | 0.322564498 | 0.295043254 |
| ILMN_1673962 | NUP205 | 0.430884869 | 0.418984732 | 0.320644827 |
| ILMN_1699623 | FAM81A | 0.424131071 | 0.427681384 | 0.420442615 |
| ILMN_1742145 | ESPL1 | 0.438541867 | 0.326763295 | 0.477971948 |
| ILMN_1690464 | TMEM20 | 0.436129606 | 0.425239244 | 0.339034609 |
| ILMN_1777397 | MSX1 | 0.438567738 | 0.402120624 | 0.435636939 |
| ILMN_1789123 | PLK4 | 0.434079417 | 0.2573706 | 0.214727663 |
| ILMN_1660654 | CDCA2 | 0.443962977 | 0.398038364 | 0.311930759 |
| ILMN_1728009 | TMEM171 | 0.436850004 | 0.35272047 | 0.397406358 |
| ILMN_1815184 | ASPM | 0.443153553 | 0.340791181 | 0.293972923 |
| ILMN_1721354 | KRT6B | 0.442537237 | 0.355081321 | 0.228058829 |
| ILMN_1736816 | C13orf3 | 0.445754679 | 0.3407389 | 0.327124395 |
| ILMN_1761463 | EFHD2 | 0.44862624 | 0.358388707 | 0.461810762 |
| ILMN_1735093 | TIMELESS | 0.452567432 | 0.326599289 | 0.315361239 |
| ILMN_1758629 | DONSON | 0.453743753 | 0.430161673 | 0.391871865 |
| ILMN_1712803 | CCNB1 | 0.455416335 | 0.377863374 | 0.371344069 |
| ILMN_1756043 | WDHD1 | 0.453924776 | 0.494572487 | 0.474699598 |
| ILMN_1686835 | C17orf41 | 0.455972071 | 0.437616789 | 0.378669917 |
| ILMN_1709294 | CDCA8 | 0.458009337 | 0.337054896 | 0.468274295 |
| ILMN_1806825 | C14orf145 | 0.460067907 | 0.417533953 | 0.474498081 |
| ILMN_1685413 | ALG8 | 0.459931384 | 0.397772753 | 0.34249794 |
| ILMN_1708101 | LMNB2 | 0.465656986 | 0.353158388 | 0.323818461 |
| ILMN_1707484 | GEMIN6 | 0.463668631 | 0.471112511 | 0.454838668 |
| ILMN_1715616 | PPIL5 | 0.466143455 | 0.324018395 | 0.20799048 |
| ILMN_1766658 | PKMYT1 | 0.473174259 | 0.267276819 | 0.326059317 |
| ILMN_1790100 | C11orf82 | 0.473975374 | 0.286688513 | 0.183979576 |
| ILMN_1726986 | AADAT | 0.471246673 | 0.427892763 | 0.432906783 |
| ILMN_1660222 | MTBP | 0.464321314 | 0.418207354 | 0.372819049 |
| ILMN_1709162 | SHCBP1 | 0.467173825 | 0.314352357 | 0.27257067 |
| ILMN_1689800 | MRTO4 | 0.477619318 | 0.421911841 | 0.343540806 |
| ILMN_1724489 | RFC4 | 0.476683584 | 0.377056541 | 0.342311821 |
| ILMN_1769931 | SFPQ | 0.481054817 | 0.459886633 | 0.439841148 |
| ILMN_1761411 | C10orf119 | 0.484065665 | 0.419366671 | 0.379577859 |
| ILMN_1760201 | DNMT1 | 0.485424175 | 0.313246431 | 0.182510347 |
| ILMN_1656274 | PRPF38A | 0.490689798 | 0.475948808 | 0.408319042 |
| ILMN_1760849 | NETO2 | 0.493065798 | 0.440610717 | 0.252902098 |
| ILMN_1802819 | DEPDC1 | 0.497440983 | 0.30696359 | 0.32884443 |
| ILMN_1679262 | DPYSL3 | 0.497744786 | 0.44701117 | 0.485819178 |
| ILMN_1700810 | HSPCAL3 | 0.493118902 | 0.423123036 | 0.161605784 |

TABLE 2-continued

List of 230 HR genes.

| UniqID | Symbol | BRCA1/Control | Rad51/Control | BRIT1/Control |
|---|---|---|---|---|
| Table 2B - Genes with increased expression ||||||

| UniqID | Symbol | BRCA1/Control | Rad51/Control | BRIT1/Control |
|---|---|---|---|---|
| ILMN_1731107 | CCDC92 | 1.988802427 | 2.162093159 | 2.371967747 |
| ILMN_1711069 | YPEL5 | 2.053624187 | 2.837300869 | 3.323701875 |
| ILMN_1658290 | C16orf68 | 2.03686802 | 2.268657709 | 2.100196149 |
| ILMN_1791580 | FXYD3 | 2.034946132 | 4.247457281 | 2.345240468 |
| ILMN_1702231 | C1orf54 | 2.086238116 | 2.331730985 | 2.204903467 |
| ILMN_1731113 | ZBTB43 | 2.074065723 | 3.15142501 | 2.718191208 |
| ILMN_1791912 | SIDT2 | 2.112281647 | 2.598423947 | 3.533338894 |
| ILMN_1731374 | CPE | 2.042128622 | 3.984208119 | 3.362317582 |
| ILMN_1695852 | C5orf38 | 2.118568019 | 3.252541727 | 2.570042221 |
| ILMN_1729208 | NGFRAP1 | 2.125393091 | 3.154848577 | 2.155877241 |
| ILMN_1659106 | PHLDA3 | 2.097599889 | 2.132099887 | 2.194606519 |
| ILMN_1790807 | XPC | 2.121985007 | 2.974242792 | 2.38238061 |
| ILMN_1693233 | KIAA0513 | 2.143071941 | 3.093698084 | 3.793709125 |
| ILMN_1739450 | NFE2L1 | 2.134717132 | 3.637359064 | 3.102526832 |
| ILMN_1694432 | CRIP2 | 2.145092145 | 2.591143524 | 7.806921586 |
| ILMN_1765258 | HLA-E | 2.167692279 | 2.215810949 | 2.634597676 |
| ILMN_1752968 | LAMB2 | 2.170610365 | 3.145643766 | 5.262791822 |
| ILMN_1809467 | VAMP5 | 2.155872871 | 2.608012186 | 2.337641787 |
| ILMN_1844692 | FOXO3 | 2.205289859 | 2.559626347 | 2.270554737 |
| ILMN_1752199 | LHPP | 2.246935602 | 2.825880934 | 1.994855038 |
| ILMN_1752394 | CCNB1IP1 | 2.260486552 | 2.830265363 | 3.520711353 |
| ILMN_1658706 | ST6GALNAC2 | 2.275729691 | 5.24415164 | 3.793785344 |
| ILMN_1746917 | LOC729843 | 2.240952378 | 3.099275042 | 4.003816651 |
| ILMN_1744534 | LYRM5 | 2.30296076 | 2.739089349 | 2.116004462 |
| ILMN_1671478 | CKB | 2.312561594 | 2.274518116 | 7.575166667 |
| ILMN_1734929 | BBOX1 | 2.251985602 | 2.749547001 | 5.101010704 |
| ILMN_1775743 | BTG1 | 2.328370191 | 2.657785691 | 3.436277395 |
| ILMN_1678170 | MME | 2.339763099 | 5.536882134 | 6.618886123 |
| ILMN_1779015 | ZNF467 | 2.339376189 | 2.293554436 | 9.782257743 |
| ILMN_1697409 | TNFRSF14 | 2.33571907 | 2.549978958 | 2.137889646 |
| ILMN_1701918 | KLHDC9 | 2.450057928 | 3.207885709 | 3.623070326 |
| ILMN_1706015 | FAM43A | 2.456029939 | 2.050305714 | 2.108117225 |
| ILMN_1811330 | FAM134B | 2.482458403 | 4.529869331 | 3.930706724 |
| ILMN_1708340 | DAPK1 | 2.574357992 | 5.796199587 | 2.406259316 |
| ILMN_1685580 | CBLB | 2.54518407 | 2.122823389 | 2.291347694 |
| ILMN_1699772 | RRAGD | 2.62423036 | 3.019393392 | 10.52803111 |
| ILMN_1718565 | CDKN1C | 2.653156246 | 2.911245812 | 5.001456828 |
| ILMN_1707312 | NFIL3 | 2.604806284 | 3.162883243 | 2.88326635 |
| ILMN_1697420 | TINF2 | 2.706579645 | 2.261593028 | 2.452682168 |
| ILMN_1685441 | DDEFL1 | 2.831304908 | 4.569974752 | 2.330241437 |
| ILMN_1715324 | HSD17B8 | 2.875672637 | 3.086925414 | 2.062796161 |
| ILMN_1770085 | BTG2 | 2.834902128 | 4.627634029 | 2.640251946 |
| ILMN_1738047 | C10orf73 | 2.86756586 | 2.580412469 | 3.010173261 |
| ILMN_1781386 | WIPI1 | 2.856431861 | 3.01597785 | 2.139754972 |
| ILMN_1684873 | ARSD | 2.685153685 | 2.945231199 | 3.551956525 |
| ILMN_1722713 | FBLN1 | 2.900641315 | 1.987562154 | 3.547087241 |
| ILMN_1770410 | LOC554223 | 2.957286603 | 2.771217512 | 2.079672605 |
| ILMN_1776788 | LOC153222 | 3.010405852 | 3.772841847 | 5.484720047 |
| ILMN_1805665 | FLRT3 | 3.018533191 | 3.492711406 | 2.096828365 |
| ILMN_1710000 | PEX11G | 3.143788641 | 2.79161817 | 2.225466822 |
| ILMN_1769394 | PLCD1 | 3.103719883 | 2.893487038 | 2.714776962 |
| ILMN_1785284 | ALDH6A1 | 3.236368847 | 3.79262783 | 5.167951941 |
| ILMN_1724700 | RIOK3 | 3.32215702 | 2.058417875 | 2.605796727 |
| ILMN_1654609 | TIGA1 | 3.35887033 | 3.656989703 | 4.303485007 |
| ILMN_1779536 | C20orf19 | 3.47770913 | 5.518372187 | 2.553267054 |
| ILMN_1694847 | TERF1 | 3.482586178 | 2.574171086 | 1.991253458 |
| ILMN_1671928 | PROS1 | 3.552265771 | 7.543219112 | 8.242123767 |
| ILMN_1690921 | STAT2 | 3.442006522 | 3.321983458 | 3.884351895 |
| ILMN_1708934 | ADM | 3.507136497 | 5.103009422 | 2.790489783 |
| ILMN_1813350 | HSD11B2 | 3.685418769 | 5.559761996 | 10.68222189 |
| ILMN_1729216 | CRYAB | 3.459757302 | 8.854932 | 4.33880944 |
| ILMN_1711092 | KCNB1 | 3.512882407 | 4.672669362 | 4.27557549 |
| ILMN_1757406 | HIST1H1C | 3.986331976 | 4.583124921 | 4.955179276 |
| ILMN_1764769 | LOH11CR2A | 4.141721251 | 3.288707215 | 3.883009111 |
| ILMN_1768227 | DCN | 4.181060184 | 4.044213258 | 12.01697678 |
| ILMN_1714861 | CD68 | 4.250032949 | 2.314747981 | 3.959001885 |
| ILMN_1803219 | TMC4 | 4.228104654 | 2.844461056 | 4.020721003 |
| ILMN_1713892 | C4orf34 | 4.236108296 | 2.959724102 | 2.075490432 |
| ILMN_1758623 | HIST1H2BD | 4.101156716 | 2.681156506 | 4.597808603 |
| ILMN_1659047 | HIST2H2AA3 | 4.324044056 | 3.503177792 | 4.473779701 |
| ILMN_1736190 | CYP4F3 | 4.368530719 | 3.849261788 | 9.630675504 |
| ILMN_1705107 | SDCBP2 | 4.968487042 | 2.631710935 | 2.461071006 |
| ILMN_1806030 | PPL | 5.042821577 | 4.205350749 | 5.927355588 |
| ILMN_1657451 | SRPK2 | 5.325304387 | 8.156428509 | 2.258578768 |

TABLE 2-continued

List of 230 HR genes.

| UniqID | Symbol | BRCA1/Control | Rad51/Control | BRIT1/Control |
| --- | --- | --- | --- | --- |
| ILMN_1728662 | ALDH3B1 | 5.644456865 | 3.777395591 | 7.888853059 |
| ILMN_1709307 | GPSM1 | 5.576670286 | 5.372485521 | 4.673408574 |
| ILMN_1766446 | C6orf48 | 6.593923999 | 5.909138584 | 2.673042098 |
| ILMN_1676984 | DDIT3 | 7.12143311 | 5.347949296 | 3.241077612 |
| ILMN_1732071 | HIST2H2BE | 6.792939944 | 7.133869903 | 3.042201085 |
| ILMN_1697448 | TXNIP | 7.639216083 | 7.310636174 | 7.211355318 |
| ILMN_1785444 | LEMD1 | 8.298821835 | 3.005963377 | 4.393202458 |
| ILMN_1698804 | ATP10B | 11.45032332 | 2.619587325 | 2.807987684 |

These data were generated using GEO accession numbers GSE54264 and GSE54266, which are incorporated herein by reference in their entirety.

The HRD Gene Signature Predicts HR-Deficiency in Cells. Next, whether the HRD gene signature was generalizable and able to predict HR-deficiency induced by deficiency in independent HR-related genes was determined Gene expression profiles were generated from isogenic MCF-10A cells with deficiency of various known key DNA damage response proteins, including ATM, ATR, CHK1, CHK2, or 53BP1, which regulate DNA damage signaling, cell cycle checkpoint activation, and DNA end resection (Ciccia and Elledge, 2010), by both shRNA stable and siRNA transient knockdown (FIGS. 9A and B). For these experiments, MCF-10A cells were infected by lentiviral particles targeting ATM, ATR, CHK1, CHK2, or 53BP1. Alternatively, MCF-10A cells were transiently transfected with siRNAs targeting ATM, ATR, CHK2, or 53BP1. Microarray analyses were conducted to verify accuracy and specificity of the HRD gene signature by supervised clustering analysis. These gene expression profiles are available as GEO accession number GSE54268, which is incorporated herein by reference in its entirety. ATM-, ATR-, CHK1-, and CHK2-deficient cells formed a cluster with the HRD gene signature. In contrast, absence of the HRD gene signature was found in 53BP1-deficienct cells. These observations are consistent with the well-established roles of the ATM-CHK2 and ATR-CHK1 pathways in regulating HR repair and the notion that 53BP1 functions as a negative regulator of DSB resection and HR repair. In order to demonstrate that such observations are not specific to MCF10A cells, transient and stable CHK1 knockdown U2OS cells, which is a human osteosarcoma cell lines and commonly used in the studies of DNA damage response and repair, were established. Separate samples of U2OS cells were either infected by lentiviral particles targeting CHK1 or transfected by the ON-TARGET-plus CHK1 siRNAs. CHK1 is a key regulator of the intra-S and G2/M DNA damage checkpoints that arrest the cell cycle and allow time for DNA repair. Microarray analyses were conducted by supervised clustering analysis. CHK1-deficient U2OS cells exhibited the same pattern of gene expression changes as those in the HRD gene signature derived from MCF10A cells. These gene expression profiles are available as GEO accession number GSE54267, which is incorporated herein by reference in its entirety. In addition, stable BRCA2-deficient MCF10A cell lines (i.e., MCF-10A cells transfected with shRNA targeting BRCA2) also exhibited the HRD gene signature. Two BRCA2 defective breast cancer cell lines were selected for supervised clustering analysis with HRD gene signature. Consistent with the above findings, these cell lines, HCC1428 and HCC1369, showed the HRD signature pattern. HCC1428 has a 6174delT mutation resulting in a 2135-base-pair deletion. HCC1369 has a nonsense mutation that causes protein truncation at E1593. Collectively, these data demonstrated that the HRD gene signature differentiates HR-deficient cells from HR-intact cells and suggest that the HRD gene signature may represent a common molecular feature among different mechanisms or cell origins of generating HR-deficiency.

Figure 10A:
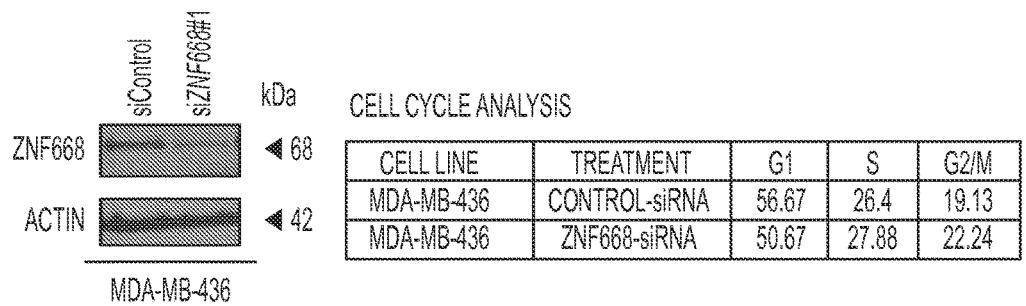
Figure 10B:
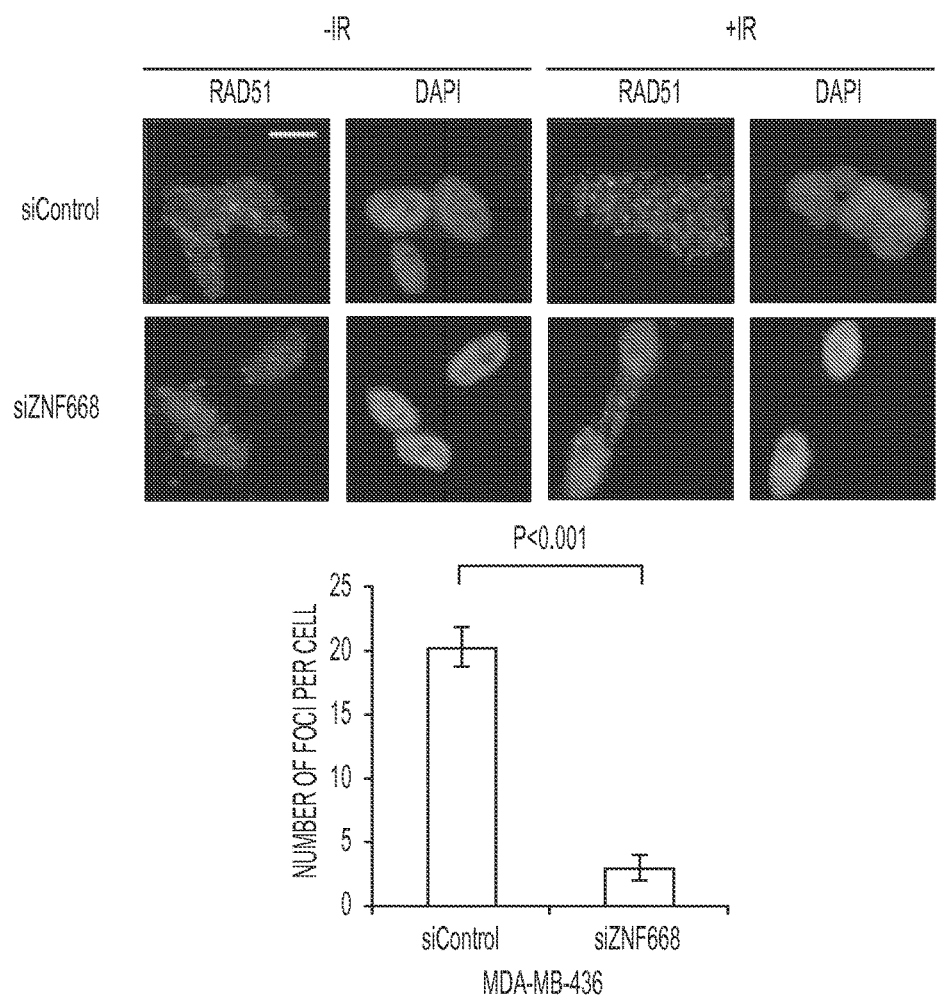
Figure 10C:
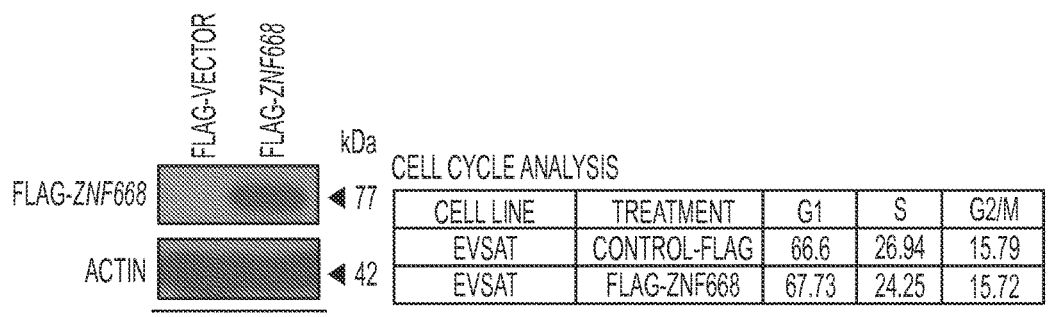
Figure 10D:
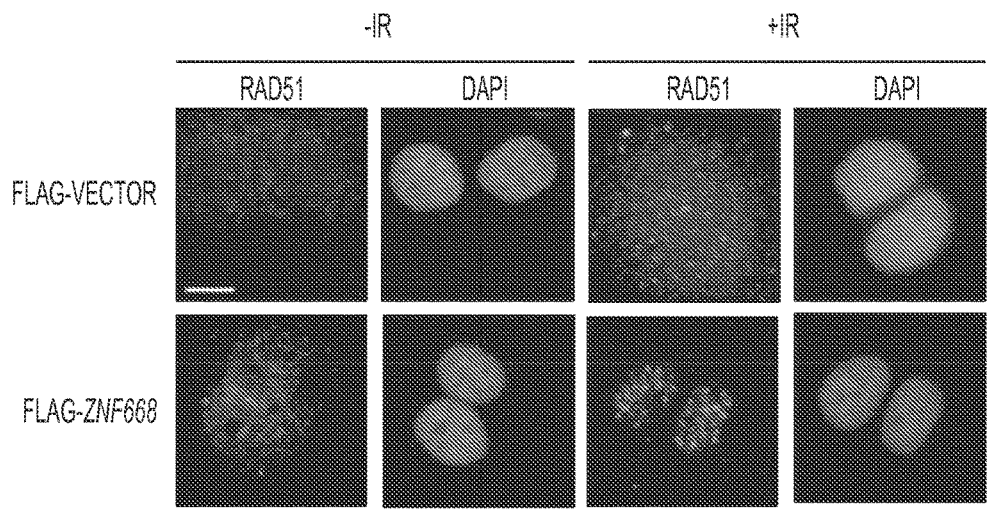
Figure 10D:
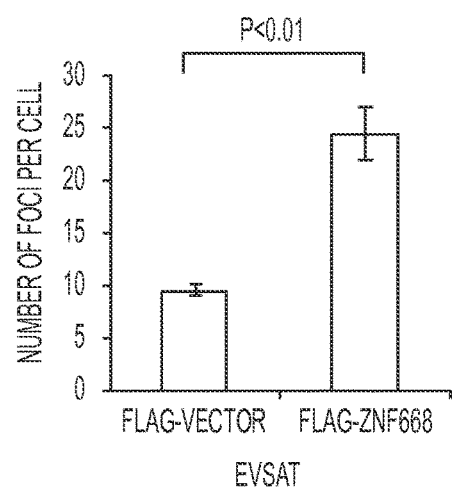

To further examine whether the HRD gene signature is functionally linked to HR repair-deficient status in cells, it was tested if it could determine whether genes with previously unknown function in HR repair are or are not involved in this process. Zinc finger protein 668 (ZNF668) was used as an example. ZNF668 was identified by genome-wide sequencing analysis as a frequently mutated gene in breast cancer (Sjoblom et al., 2006; Wood et al., 2007), and it was recently demonstrated that ZNF668 regulates p53 stability (Hu et al., 2011). However, molecular mechanisms underlying its tumor suppression function remain elusive. MCF-10A cells were transfected by the ON-TARGET-plus ZNF668 siRNAs. Microarray analyses of ZNF668-deficient cells were conducted and supervised clustering analysis was used to assess whether ZNF668-deficient cells exhibited the HRD gene signature. Although individual HR repair factors, such as BRCA1/2, RAD51, BRIT1, ATM, ATR, CHK1, and CHK2, were not identified as top candidate genes based on expression changes in ZNF668-knockdown cells, these cells clearly exhibited the HRD gene signature. Based on a classic HR repair assay, ZNF668 knockdown significantly impaired HR repair efficiency (FIG. 1E). Cell cycle analysis of ZNF668 knockdown cells showed no apparent difference in cell cycle distribution compared to control cells, which excluded an effect of cell cycle progression on HR repair (FIG. 1E). ZNF668 was also knocked down in MDA-MB-436 breast cancer cells, which have a relatively high expression of ZNF668 compared to other breast cancer cell lines. ZNF668 depletion significantly reduced RAD51 foci formation after IR treatment, without affecting cell cycle distribution (FIGS. 10A and B). In addition, ZNF668 expression was reconstituted in a breast cancer cell line, EVSAT, which contains a ZNF668 nonsense mutation. The restored expression of ZNF668 remarkably increased IR-induced RAD51 foci formation compared to control cells reconstituted with an empty vector with no apparent effect on cell cycles distribution (FIGS. 10C and D). These results showed that the HRD gene signature can functionally link gene expression patterns with HR-deficiency not only in a genetic engineered model systems but also various cancer cell lines, providing an opportunity to identify unexpected key players in HR repair.

The HRD Gene Signature Predicts HR Repair Deficiency and Sensitivity to PARP Inhibitor Treatment in Human Cancer Cells with Diverse Genetic Backgrounds. Poly (ADP-ribose) polymerase (PARP) inhibitors are recently identified targeted therapeutic drugs that specifically kill HR-repair deficient cells via a synthetic lethality interaction (Bryant et al., 2005; Farmer et al., 2005). As expected, BRAC1-, RAD51-, and BRIT1-deficient cells exhibited greatly increased cellular sensitivity to PARP inhibitor olaparib (FIG. 11A). Thus, it was reasoned that if the HRD gene signature is functionally linked to HR-deficiency, it may serve as a powerful tool to predict the sensitivity of human cancer cells with diverse genetic backgrounds to PARP inhibitors.

Figure 2A:
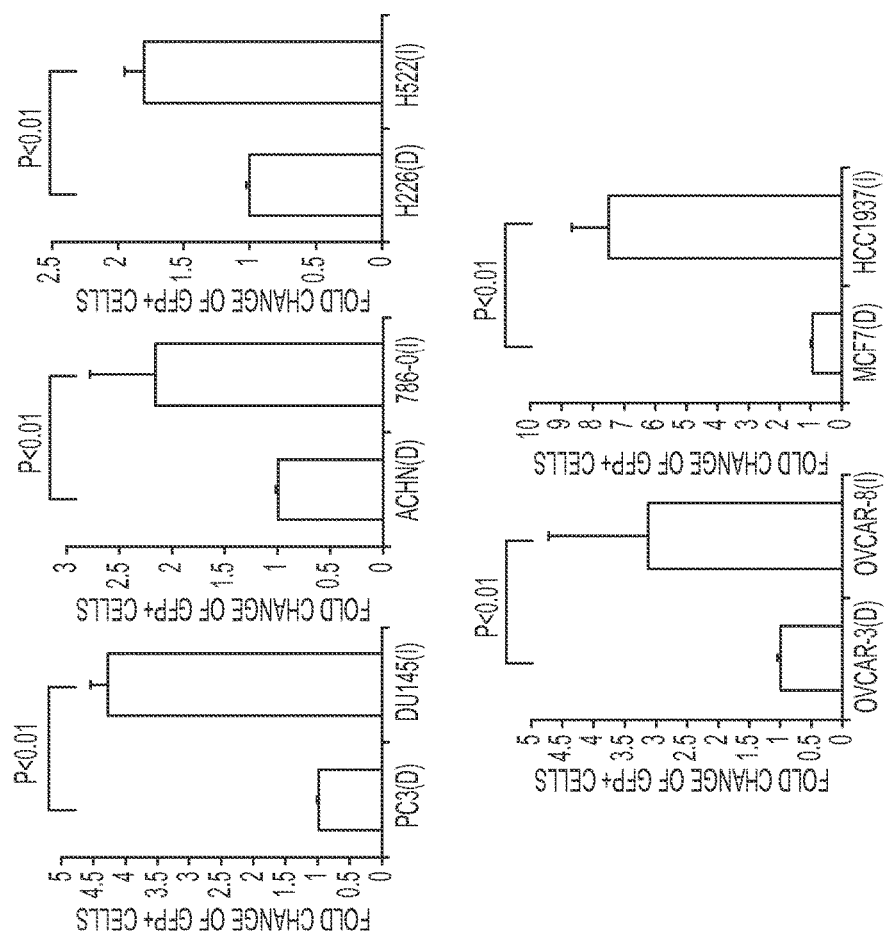
FIGS. 2A-D. The HRD Gene Signature Predicts Sensitivity to PARP Inhibitors in Cancer Cells. (A) Cell lines with intact HR (I) and defective HR (D) were selected for five cancer types as follows: prostate cancer: PC-3 (D) and DU-145 (I); renal cancer: ACHN (D) and 7860-O (I); lung cancer: H266 (D) and H522 (I); ovarian cancer: OVCAR-3 (D) and OVCAR-8 (I); and breast cancer: MCF7 (D), MDA-MB-231 (I), and HCC1937 (I). Modified HR repair assay was performed by transfecting cells with DRGFP DSB substrate plasmid and I-SceI plasmid through electroporation at 270V, 975uF using a BioRad genepulsar II. Flow cytometry analysis was performed 48 to 72 hours later to detect GFP-positive cells. Each value is relative to the percentage of GFP-positive cells in I-SceI-transfected control cells. Each value is shown as mean±SD for three independent experiments. Student's t-test was used to test statistical significance. (B-D) Colony formation assay was performed with the indicated concentrations of olaparib (B) or rucaparib (C), or (D) cell lines were seeded in 96-well plates, treated with olaparib at the indicated concentrations for 5 days, and then analyzed by MTT assay. Each value is relative to the value in the cells treated with vehicle control. Results are shown as mean±SD from three independent experiments. Student's t-test showed that the drug response to PARP inhibitors differed between cancer cell lines with and without the HRD gene signature ($P<0.05$ through panels B and C).

To test this possibility, two cell-line panels were used: National Cancer Institute 60 (NCI60) (Shoemaker, 2006) and a collection of 51 breast cancer lines (ICBP51) (Neve et al., 2006), which consist of cell lines from diverse human cancers that have been well characterized genetically and molecularly. Gene expression profiles of NCI60 (available as GEO accession number GSE32474, which is incorporated by reference in its entirety) and breast cancer 51 cell lines (see Neve et al., 2006, which is incorporated herein by reference in its entirety) were clustered hierarchically into two groups on the basis of their similarity to the HRD gene signature. For prostate, renal, lung, ovarian, and breast cancers, cell lines were selected with intact and defective HR repair as predicted by the HRD gene signature and HR repair efficiency was determined using a classical HR repair assay. Importantly, cell lines with the HRD gene signature showed reduced HR repair efficiency compared to their counterparts without the signature in each cancer type (FIG. 2A). Therefore, the sensitivity of these cell lines to PARP inhibitor treatment, which is synthetic lethal in HR-deficient cells, was tested. Consistent with the results from the HR repair assay, cell lines with the HRD gene signature were more sensitive to PARP inhibitors olaparib (FIGS. 2B and 2D) or recaparib (FIG. 2C) treatment than cell lines with intact HR repair. It is very likely that PARP inhibitors will also be used in combination with standard DNA damaging agents in the clinic. Therefore, it was further tested whether cell lines with the HRD gene signature would be more sensitive to the treatment combining PARP inhibitors with temazolomide, a standard chemotherapy regimen. As shown in FIG. 11B, consistent with the results from PARP inhibitor monotherapy, the HR-deficient cell line showed enhanced sensitivity compared to the HR-intact cell line.

Having determined the association between the HRD gene signature and HR repair capacity in cancer cell lines, it was next asked whether the changes of the HRD gene signature at the transcriptional levels were correlated with their changes at the protein level in cancer cells. To answer this question, systematic proteomic profiling data was obtained through a mass spectrometry analysis from breast cancer cell lines, which are identified as HR-deficient or HR-intact cell lines by gene signature analysis. We then compared the difference of protein expression levels between HR-deficient and HR-intact cell lines (Table 3). The change at the protein level is closely correlated with the changes at the transcriptional level. In FIGS. 12A and B and Table 4, we further showed that similar functional pathways and networks were identified from proteomic data analysis compared to the microarray data analysis (FIGS. 7A and B and Table 1).

Together, these data suggest that gene expression profile analysis may permit functional identification of HR-deficiency without the need for identification of the specific genetic or epigenetic aberrations in the HR repair network and, more importantly, that the HRD gene signature may be used to predict the sensitivity of tumor cells to targeted therapeutics for HR deficiency, such as PARP inhibitors.

TABLE 3

Difference in protein expression levels between HR-deficient and HR-intact cell lines.

| Gene Symbol | Fold change of protein expression (log2; HRD-HRI) |
|---|---|
| HIST2H2BE | 2.556334151 |
| CRIP2 | 1.39199774 |
| HIST1H1C | 0.964876083 |
| CKB | 0.933599789 |
| HSD17B8 | 0.869685769 |
| SRPK2 | 0.82521573 |
| CDKN1C | 0.622791483 |
| TMC4 | 0.482100578 |
| BBOX1 | 0.477039883 |
| ATP10B | 0.370033598 |
| ADM | 0.304107288 |
| BTG1 | 0.304107288 |
| ZNF467 | 0.304107288 |
| FOXO3 | 0.283759237 |
| LAMB2 | 0.283048896 |
| NFIL3 | 0.266214297 |
| HLA-E | 0.261664324 |
| STAT2 | 0.246909199 |
| CCDC92 | 0.235994459 |
| ALDH6A1 | 0.219494635 |
| TINF2 | 0.20988541 |
| FAM134B | 0.204056964 |
| WIPI1 | 0.204056964 |
| RIOK3 | 0.173404758 |
| XPC | 0.160120276 |
| ARSD | 0.159716707 |
| SDCBP2 | 0.149647189 |
| ALDH3B1 | 0.100518239 |
| TNFRSF14 | 0.066606971 |
| VAMP5 | 0.066606974 |
| KIAA0513 | 0.058775178 |
| CD68 | 0.054910808 |
| PLCD1 | 0.054910808 |
| ST6GALNAC2 | 0.041966278 |
| CBLB | 0.035595689 |
| RFC4 | −0.006349747 |
| TMEM158 | −0.011627835 |
| LRP8 | −0.017292496 |
| DONSON | −0.021600071 |
| ASF1B | −0.033199971 |
| MT1G | −0.050323523 |
| TUB4Q | −0.053956643 |
| CCNE1 | −0.083270614 |
| POLD1 | −0.090682089 |
| GINS4 | −0.094387468 |
| PLEK2 | −0.117094537 |
| POLQ | −0.126312198 |
| RNASEH2A | −0.12809325 |
| PRC1 | −0.131410255 |
| MSH6 | −0.140207518 |
| TYMS | −0.174623925 |
| FANCI | −0.194487889 |
| WDHD1 | −0.19879118 |
| BLM | −0.208861963 |
| C11orf82 | −0.218339806 |
| RFC3 | −0.29024922 |
| DPYSL3 | −0.317597756 |
| C14orf145 | −0.365709844 |
| ASPM | −0.444256783 |
| PDXP | −0.44573542 |
| CDCA2 | −0.455143465 |
| MRTO4 | −0.51528056 |
| DNMT1 | −0.555028316 |
| SLC25A13 | −0.566738014 |
| KIF14 | −0.596530669 |
| CCNA2 | −0.648020185 |
| CCNB1 | −0.759072146 |
| MCM5 | −0.798476624 |
| KIF2C | −0.836327094 |
| ANLN | −0.965423785 |
| MSH2 | −0.966949371 |
| CTSC | −1.001087875 |
| C10orf119 | −1.129001934 |
| NUP205 | −1.235251204 |

TABLE 3-continued

Difference in protein expression levels between
HR-deficient and HR-intact cell lines.

| Gene Symbol | Fold change of protein expression (log2; HRD-HRI) |
|---|---|
| TUBA4A | −1.307098927 |
| HMGB3 | −1.32621119 |
| LMNB2 | −1.826436807 |
| FDPS | −1.935751084 |

TABLE 4

Protein-set enrichment analysis by Ingenuity program.

| Name | p-value |
|---|---|
| Molecular and Cellular Functions | |
| Cell Cycle | 8.63E−09−1.69E−02 |
| DNA Replication, Recombination, and Repair | 2.16E−07−1.58E−02 |
| Nucleic Acid Metabolism | 2.05E−05−1.27E−02 |
| Small Molecule Biochemistry | 2.05E−05−1.27E−02 |
| Cellular Assembly and Organization | 5.00E−05−1.69E−02 |
| Top Canonical Pathways | |
| Mismatch Repair in Eukaryotes | 5.15E−09 |
| Hereditary Breast Cancer Signaling | 3.24E−08 |
| Role of BRCA1 in DNA Damage Response | 2.03E−07 |
| DNA Damage-induced 14-3-3σ Signaling | 6.85E−05 |
| GADD45 Signaling | 8.03E−05 |

Figure 2B:
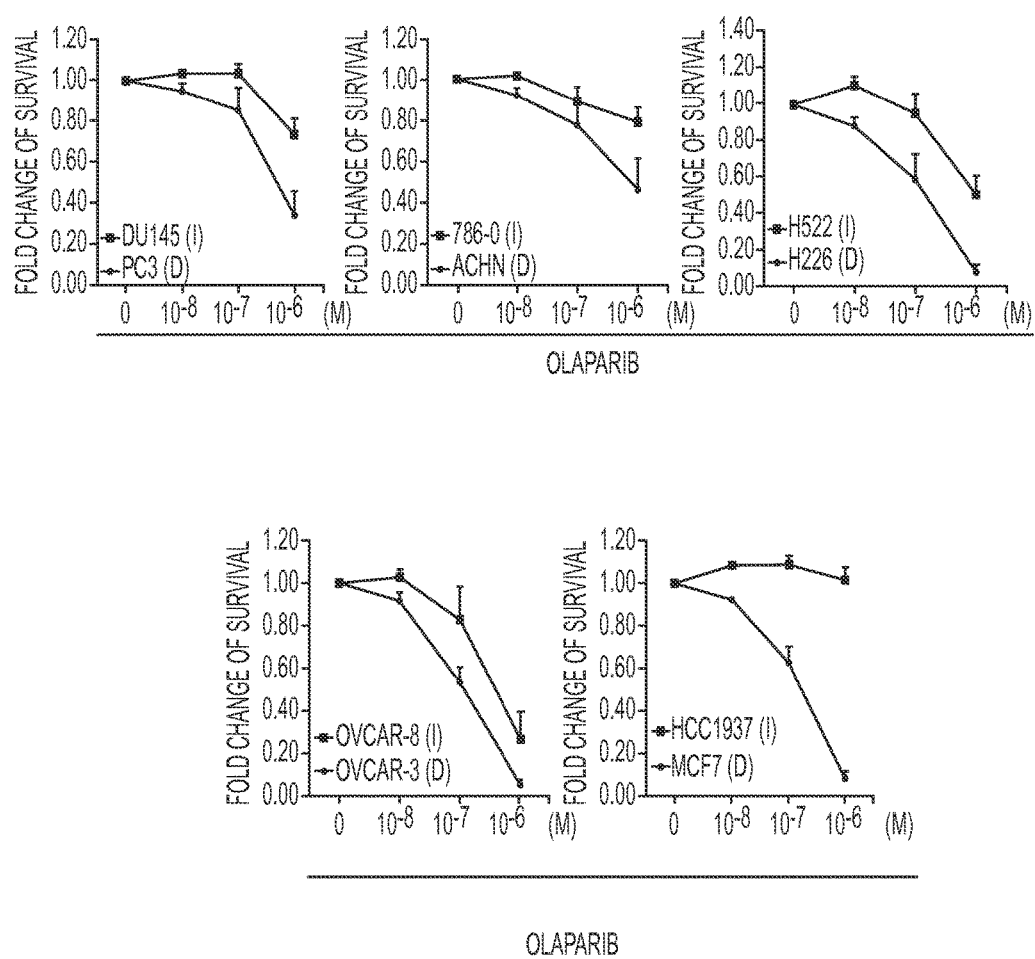
Figure 2C:
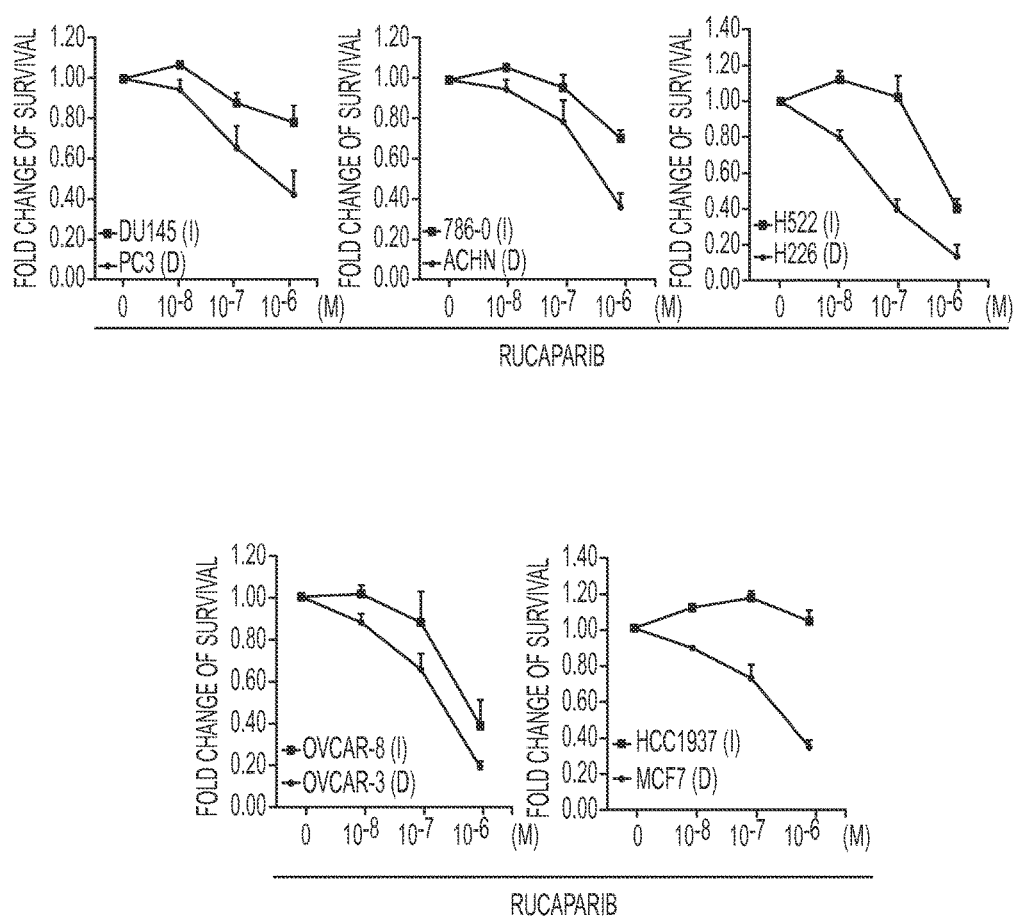
Figure 2D:
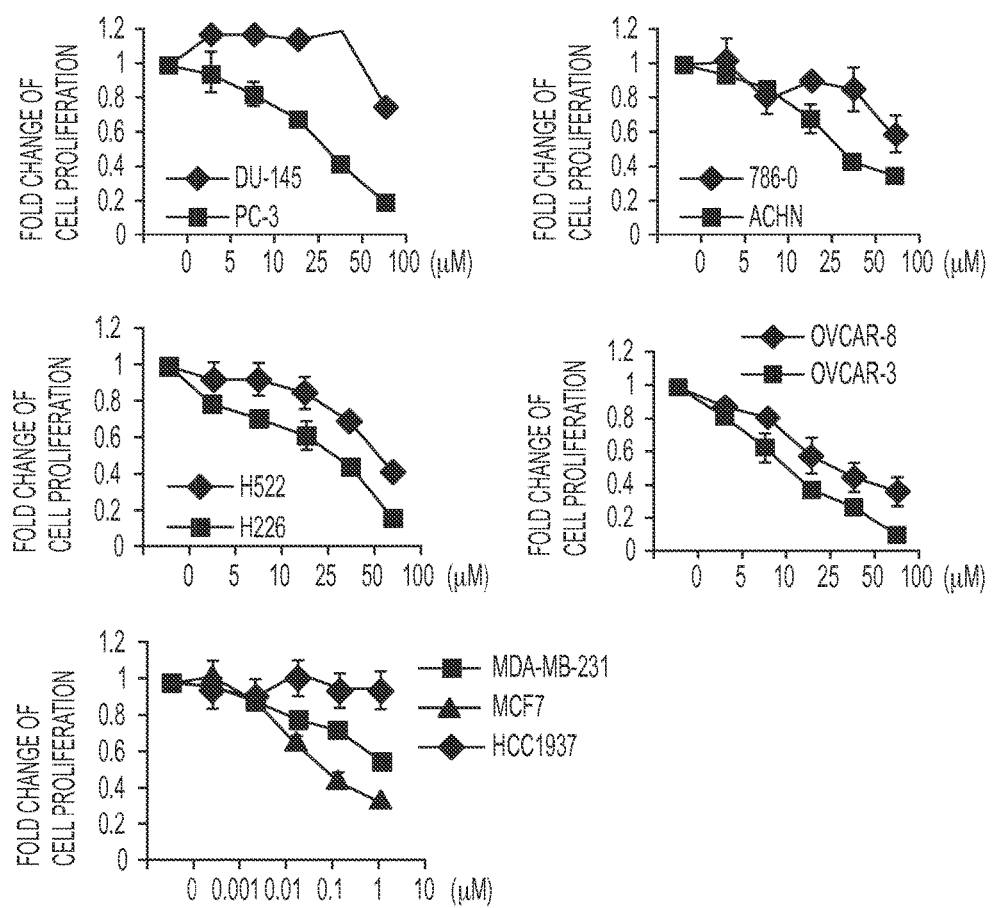

Reversal of HR-Deficiency in BRCA1-Depleted Cells. Interestingly, analyses showed that breast cancer cell line HCT1937, which has BRCA1 mutations, did not exhibit the HRD gene signature, did not exhibit HR repair deficiency, and did not exhibit increased sensitivity to PARP inhibitor treatment compared to MCF-7 cells with wild-type BRCA1 (FIGS. 2A-C). Furthermore, another breast cancer cell line with BRCA1 mutations, MDA-MB-436, also did not have the HRD gene signature. It was sought to identify the mechanisms underlying the lack of HRD gene signature in these BRCA1-mutated cells.

It was suspected that due to impaired DNA repair, additional genetic alterations may accumulate in these BRCA1-mutated cells that, in turn, restore HR repair deficiency. PTEN regulates HR repair through altering RAD51 expression and through checkpoint control (Gupta et al., 2009; Shen et al., 2007), and PTEN deficiency sensitizes cancer cells to PARP inhibitor treatment (Mendes-Pereira et al., 2009). However, a recent study indicated that PTEN status is not a direct mediator of HR repair status in prostate cancer (Fraser et al., 2012). These data suggest that the effects of PTEN loss on HR repair might depend on cell type or genetic context. A recent study has reported that PTEN is frequently mutation in BRCA1-deficient tumors, and is indeed mutated in HCC1937 (Saal et al., 2008). In light of these observations, it was asked whether PTEN loss might affect HR repair in BRCA1-deficient cells.

BRCA1 knockdown, PTEN knockdown, and BRCA1-PTEN double knockdown cells were generated in the MCF-10A background by infection with lentiviral particles targeting the indicated genes, and these cell lines were subjected to microarray analyses. These expression profiles are available as GEO accession number GSE54265, which is incorporated herein by reference in its entirety. Expression of these genes was significantly reduced in the knockdown cells, and deficiency of these genes did not affect the cell cycle distribution under normal culture conditions (FIG. 13).

Interestingly, cells with BRCA1 deficiency or PTEN deficiency formed a cluster with the HRD gene signature. However, BRCA1-PTEN double knockdown cells, such as HCC1937, had a gene signature similar to that of control cells, suggesting that co-concurrent loss of PTEN and BRCA1 could potentially restore the HR repair efficiency in cells with defection of either BRCA1 or PTEN gene alone.

Figure 3A:
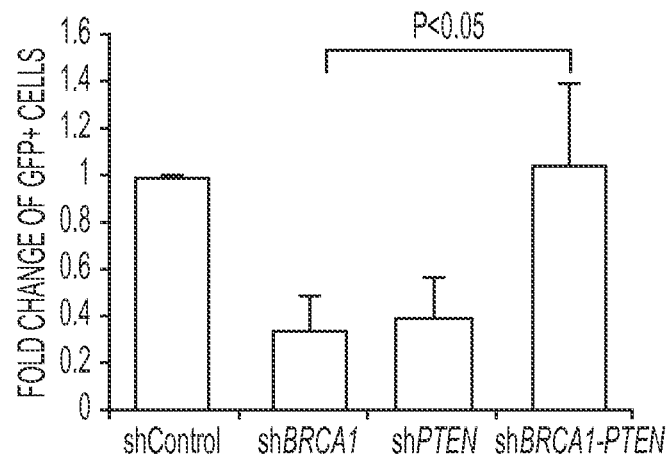
FIGS. 3A-C. Loss of PTEN Reverses HRD and Confers PARP Inhibitor Resistance to BRCA1-Depleted Cells through Over-expression of TTK. (A) Modified HR repair assay was performed in MCF-10A cells by transfecting cells with DRGFP DSB substrate plasmid and I-SceI plasmid through electroporation, followed by analysis of GFP-positive cells by flow cytometry 48 to 72 hours later. Each value is relative to the percentage of GFP-positive cells in I-SceI-transfected control cells. Results are show as mean±SD from three independent experiments. Student's t-test was performed from results of three independent experiments. (B) Cells were seeded at a very low density and treated with indicated concentrations of olaparib for 10 to 15 days to allow colony formation. The rate of cell survival in response to olaparib was determined by colony formation assay. Each value was relative to control cells without treatment and represents the mean±SD from three independent experiments. Student's t-test showed that treatment response differed between BRCA1-PTEN double knockdown cells and single knockdown cells ($P<0.001$). (C) Quantitative analysis of HR repair assay in cells transfected with TTK plasmids or the indicated siRNAs. Each value is relative to the percentage of GFP-positive cells in I-SceI-transfected control cells. Results are shown as mean±SD from three independent experiments. Student's t-test showed that overexpression of TTK significantly increased HR repair efficiency ($P<0.05$). BRCA1 SMARTpool siRNA was used as a positive control. Western blots demonstrating effective knockdown are shown to the bottom.
Figure 3B:
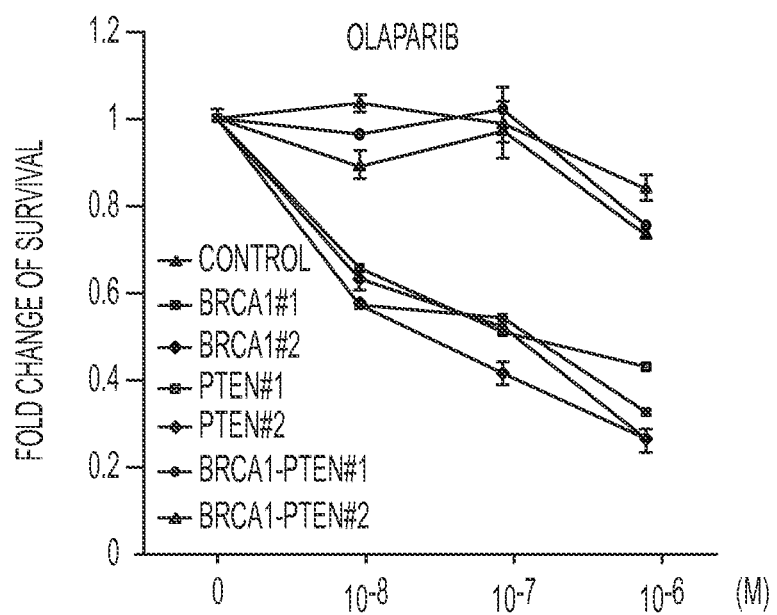
Figure 3C:
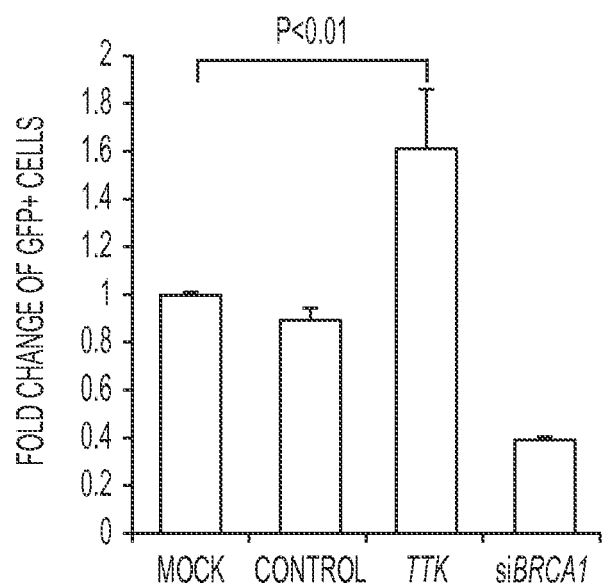
Figure 3C:
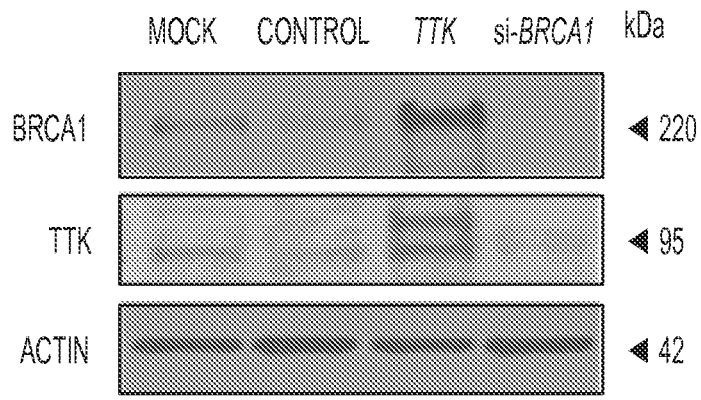

To further test this possibility, functional HR repair assays were conducted in the knockdown cell lines. As expected, PTEN-BRCA1 double knockdown cells showed an increase in HR repair efficiency (or restored HR repair efficiency) compared with BRCA1 or PTEN knockdown cells (FIG. 3B). Then, the sensitivity of these cells to PARP inhibitor treatment was tested. BRCA1 and PTEN deficiency independently sensitized cells to olaparib treatment (FIG. 3C), consistent with previously reported functions of BRCA1 and PTEN in regulating HR repair (Bryant et al., 2005; Farmer et al., 2005; Mendes-Pereira et al., 2009; Shen et al., 2007). However, BRCA1-PTEN double knockdown did not sensitize cells to PARP inhibitor treatment (FIG. 3C) and indeed were indistinguishable from parental cells. Collectively, these data strongly support the concept that additional genetic alterations, such as loss of PTEN, can reverse HR-deficiency in BRCA1-deficient cells, suggesting that analysis of genetic alterations in individual genes involved in HR repair may not reflect the overall functional status of the HR repair network. In contrast, the HRD signature can provide a functional assessment of HR repair status that integrates inputs form multiple upstream mediators.

Next, it was sought to understand the molecular mechanism underlying the enhanced HR repair in PTEN-BRCA1 double knockdown cells. Twenty-six genes were identified in the HRD signature that had the greatest differences in expression between BRCA1-PTEN double knockdown cells and single-gene-knockdown cells, using a scoring system described in Example 3 (Table 5). Among these candidate genes, kinases were focused on as they represent the most druggable targets for chemical modulation of the HR repair network. Expression levels of the TTK protein kinase (Mills et al., 1992) was downregulated in PTEN and BRCA1 single-gene-knockdown cells. However, TTK expression was increased in BRCA1-PTEN double knockdown cells (Table 5). As co-mutations of BRCA1 and PTEN are frequently observed in basal-like breast cancer (Saal et al., 2008), TTK expression was analyzed in this breast cancer subtype. Microarray data from 295 breast cancers (see van de Vijver et al., 2002) were clustered into basal-like, Her2-positive (Her2), luminal A, luminal B, and normal breast-like. TTK expression was found to be significantly enriched in basal-like breast cancer compared to other breast cancer subtypes. In addition, the basal-like breast cancer cell lines, HCC1937 and MDA-MB-436, which contain both BRCA1 and PTEN mutations, had a higher TTK expression levels than other breast cancer cell lines (FIG. 14A). TTK is a dual-specificity protein kinase that can phosphorylate tyrosine, serine, and threonine (Mills et al., 1992). TTK is associated with cell proliferation and regulates chromosome alignment and segregation during mitosis (Mills et al., 1992; Saurin et al., 2011; Stucke et al., 2002). It remains unknown whether TTK plays a direct role in DNA repair. Thus, it was tested whether TTK regulates HR repair. As expected, over-expression of TTK increased HR repair (FIG. 3F). These results suggested that increased expression of TTK may contribute to increased HR repair efficiency in BRCA1-PTEN double knockdown cells. Moreover, TTK inhibitor AZ3146 enhanced olaparib-induced apoptosis in HCC1937 cells (FIG. 14B). Altogether these data demonstrated that concurrent loss of PTEN and BRCA1 might rewire the HR repair network through regulating the expression of key genes, such as TTK, which may be responsible for PARP inhibitor resistance observed in clinical trials in basal-like breast cancer or TNBC carrying a high frequency of dysfunctional BRCA1 and PTEN (Saal et al., 2008).

Next, it was tested whether genetic and chemical inhibition of TTK could sensitize HCC1937 and MDA-MB-436 cells to PARP inhibitor treatment. In MDA-MB-436 cells, TTK knockdown significantly increased apoptosis induced by PARP inhibitor treatment and reduced cell proliferation as measured by BrdU incorporation (FIG. 17A). Consistent with these observations, TTK inhibitor enhanced PARP inhibitor-induced apoptosis in HCC1937 cells (FIG. 17B). These findings suggested that combining a TTK inhibitor with a PARP inhibitor might overcome resistance of these cancers to PARP inhibitor treatment or alternatively prevent the emergence of resistance.

TABLE 5

PTEN-BRAC1 scores.

| UNIQID | NAME | control1.2nd | control2.2nd | control3.2nd | control4.2nd | BRCA1.42.2nd | BRCA1.43.2nd | BRCA1.44.2nd |
|---|---|---|---|---|---|---|---|---|
| ILMN_1659047 | HIST2H2AA3 | 1151.42 | 1538.87 | 1693.96 | 837.07 | 2107.58 | 1912.38 | 1480.44 |
| ILMN_1672536 | FBLN1 | 3623.76 | 3805.65 | 3742.74 | 2047.05 | 2484.57 | 2427.46 | 2256.82 |
| ILMN_1757406 | HIST1H1C | 422.57 | 452.08 | 480.41 | 313.98 | 857.42 | 801.9 | 877.58 |
| ILMN_1708934 | ADM | 4022.85 | 3993.04 | 4228.48 | 2401.63 | 2154.42 | 3403.32 | 3163.52 |
| ILMN_1706015 | FAM43A | 310.23 | 319.83 | 280.18 | 230.66 | 956.95 | 837.36 | 784.9 |
| ILMN_1739645 | ANLN | 1040.26 | 1018.23 | 990.57 | 1627.48 | 870.62 | 726.26 | 808.11 |
| ILMN_1651496 | HIST1H2BD | 978.73 | 997.76 | 1052.84 | 667.58 | 1983.74 | 1506.71 | 1430.56 |
| ILMN_1694432 | CRIP2 | 130.62 | 119.08 | 144.12 | 200.46 | 491.74 | 420.44 | 300.1 |
| ILMN_1788166 | TTK | 1058.25 | 983.66 | 977.34 | 933 | 657.51 | 601.87 | 582.91 |
| ILMN_1802819 | DEPDC1 | 452.2 | 367.33 | 367.96 | 509.07 | 315.71 | 268.58 | 289.61 |
| ILMN_1749829 | DLG7 | 845.6 | 677.61 | 671.45 | 800.71 | 568.37 | 588.69 | 608.85 |
| ILMN_1671928 | PROS1 | 391.99 | 342.55 | 408.4 | 293.79 | 534.54 | 733.27 | 880.41 |
| ILMN_1678170 | MME | 186.33 | 177.5 | 212.96 | 176.85 | 1101.22 | 722.05 | 697.39 |
| ILMN_1731107 | CCDC92 | 684.75 | 756.67 | 739.61 | 637.66 | 945.23 | 1060.41 | 952.93 |
| ILMN_1654609 | TIGA1 | 3735.56 | 4174.71 | 4527.37 | 2765.67 | 2800.16 | 3703.23 | 3517.83 |
| ILMN_1804090 | SLC25A10 | 553.61 | 510.91 | 587.18 | 784.9 | 627.24 | 696.71 | 570.98 |
| ILMN_1801664 | POLR3K | 892.94 | 868.6 | 910.39 | 1016.81 | 1005.56 | 1001.21 | 923.02 |
| ILMN_1808071 | KIF14 | 601.72 | 580.47 | 554 | 647.38 | 411.8 | 432.35 | 345.09 |
| ILMN_1665797 | CSE1L | 3952.65 | 3200.28 | 3419.68 | 3845.19 | 2701.59 | 2227.27 | 2480.44 |
| ILMN_1736190 | CYP4F3 | 179.5 | 197.04 | 198.19 | 135.74 | 580.13 | 464.74 | 500.57 |
| ILMN_1707312 | NFIL3 | 245.11 | 234.13 | 256.66 | 284.16 | 190.17 | 148.23 | 171.13 |
| ILMN_1760849 | NETO2 | 5032.17 | 4029.53 | 4449.84 | 4306.19 | 3173.31 | 3454.28 | 3499.73 |
| ILMN_1657451 | SRPK2 | 326.37 | 315.94 | 313.92 | 298.34 | 423.66 | 349.1 | 375.28 |
| ILMN_1673962 | NUP205 | 1329.8 | 1317.1 | 1356.98 | 2073.37 | 1216.7 | 1197.22 | 1349.73 |
| ILMN_1697409 | TNFRSF14 | 419.15 | 365.95 | 401.59 | 248.23 | 332.5 | 378.28 | 402.42 |
| ILMN_1732071 | HIST2H2BE | 296.39 | 304.92 | 307.72 | 225.78 | 406.85 | 305.14 | 300.05 |

| UNIQID | BRCA1.53.2nd | PTEN.21.2nd | PTEN.22.2nd | PTEN.23.2nd | PTEN.24.2nd | PTENBRCA.54.2nd |
|---|---|---|---|---|---|---|
| ILMN_1659047 | 1098.09 | 2914.5 | 2870.09 | 2696.25 | 2625.44 | 1531.68 |
| ILMN_1672536 | 1682.18 | 2508.38 | 2301.95 | 2335.33 | 2203.6 | 928.87 |
| ILMN_1757406 | 756.67 | 2084.64 | 1981.76 | 1691.45 | 1941.02 | 766.24 |
| ILMN_1708934 | 4933.74 | 4585.12 | 5000.58 | 4673.88 | 4719.31 | 2649.13 |
| ILMN_1706015 | 795.41 | 1381.61 | 1417.92 | 1406.42 | 1391.79 | 431.87 |
| ILMN_1739645 | 480.41 | 868.6 | 834.2 | 863.18 | 974.15 | 1605.97 |
| ILMN_1651496 | 612.58 | 2087.44 | 2112.57 | 2007.76 | 2277.59 | 1570.65 |
| ILMN_1694432 | 160.13 | 525.96 | 596.58 | 567.86 | 613.49 | 196.9 |
| ILMN_1788166 | 660.12 | 616.57 | 649.69 | 574.48 | 557.57 | 776.81 |
| ILMN_1802819 | 236.08 | 336.83 | 346.16 | 355.57 | 299.24 | 389.09 |
| ILMN_1749829 | 645.65 | 479.76 | 492.4 | 629.43 | 701.47 | 779.95 |
| ILMN_1671928 | 1125.2 | 1021.43 | 1040.26 | 1051.74 | 1045.17 | 633.26 |
| ILMN_1678170 | 335.83 | 1002.92 | 1161.45 | 902.59 | 1000.57 | 187.39 |
| ILMN_1731107 | 975.86 | 888.84 | 947.77 | 763.43 | 941.07 | 740.77 |
| ILMN_1654609 | 4625.78 | 3127.25 | 3257.66 | 2852.4 | 3010.35 | 1881.68 |
| ILMN_1804090 | 482.14 | 729.16 | 754.04 | 778.45 | 830.12 | 544.56 |
| ILMN_1801664 | 998.43 | 1153.7 | 1096.33 | 1045.5 | 1102.98 | 1020.17 |
| ILMN_1808071 | 320.28 | 360.09 | 411.67 | 423.99 | 435.68 | 579.58 |
| ILMN_1665797 | 2273.44 | 2976.54 | 2696.25 | 2867.31 | 2843 | 2980.16 |
| ILMN_1736190 | 229.25 | 549.3 | 494.39 | 558.65 | 536.46 | 210.15 |
| ILMN_1707312 | 192.88 | 168.93 | 220.11 | 210.3 | 170.43 | 237.11 |
| ILMN_1760849 | 3570.93 | 3333.15 | 3430.77 | 3718 | 3700.27 | 4746.65 |
| ILMN_1657451 | 322.57 | 510.91 | 485.72 | 468.64 | 549.5 | 286.81 |
| ILMN_1673962 | 1136.56 | 1199.86 | 1231.36 | 1213.44 | 1237.47 | 1445.53 |
| ILMN_1697409 | 368.92 | 655.67 | 626.37 | 574.19 | 642.11 | 408.31 |
| ILMN_1732071 | 182.44 | 493.11 | 489.96 | 479.31 | 480.65 | 247.35 |

| UNIQID | PTENBRCA.41.2nd | PTENBRCA.42.2nd | PTENBRCA.43.2nd | PTENBRCA1 Mean | Score |
|---|---|---|---|---|---|
| ILMN_1659047 | 592.74 | 465.33 | 163.51 | 688.315 | 0.665157 |
| ILMN_1672536 | 694.42 | 724.52 | 728.94 | 769.1875 | 0.676705 |
| ILMN_1757406 | 341.56 | 303.71 | 158.62 | 392.5325 | 0.680669 |
| ILMN_1708934 | 1461.58 | 1314.54 | 870.62 | 1573.968 | 0.792797 |
| ILMN_1706015 | 483.89 | 447.23 | 320.21 | 420.8 | 0.799475 |

TABLE 5-continued

PTEN-BRAC1 scores.

| | | | | | |
|---|---|---|---|---|---|
| ILMN_1739645 | 1470.34 | 1657.09 | 2790.55 | 1880.988 | 0.85401 |
| ILMN_1651496 | 742 | 573.16 | 284.16 | 792.4925 | 0.946441 |
| ILMN_1694432 | 229.54 | 278.48 | 140.92 | 211.46 | 0.983453 |
| ILMN_1788166 | 1108.49 | 1240.37 | 1839.28 | 1241.238 | 0.987063 |
| ILMN_1802819 | 528.1 | 633.26 | 919.02 | 617.3675 | 0.991217 |
| ILMN_1749829 | 909.12 | 1044.29 | 1937.38 | 1167.685 | 1.009395 |
| ILMN_1671928 | 383.65 | 407.68 | 463.3 | 471.9725 | 1.030706 |
| ILMN_1678170 | 413.72 | 485.49 | 739.81 | 456.6025 | 1.088411 |
| ILMN_1731107 | 419.27 | 450.75 | 426.33 | 509.28 | 1.093045 |
| ILMN_1654609 | 2833.73 | 2037.92 | 615.51 | 1842.21 | 1.104748 |
| ILMN_1804090 | 332.06 | 318.42 | 296.55 | 372.8975 | 1.10993 |
| ILMN_1801664 | 567.71 | 497.05 | 223.48 | 577.1025 | 1.112464 |
| ILMN_1808071 | 646.44 | 652.72 | 846.86 | 681.4 | 1.152388 |
| ILMN_1665797 | 3757.61 | 4358.96 | 7092.49 | 4547.305 | 1.15815 |
| ILMN_1736190 | 331.82 | 314.69 | 272.22 | 282.22 | 1.16391 |
| ILMN_1707312 | 285.48 | 319.23 | 410.75 | 313.1425 | 1.175328 |
| ILMN_1760849 | 5000.58 | 5731.17 | 8230.16 | 5927.14 | 1.175965 |
| ILMN_1657451 | 275.35 | 275.89 | 173.09 | 252.785 | 1.189429 |
| ILMN_1673962 | 1897.87 | 2072.09 | 2786.93 | 2050.605 | 1.192616 |
| ILMN_1697409 | 236.13 | 257.77 | 209.96 | 278.0425 | 1.195555 |
| ILMN_1732071 | 195.55 | 202.1 | 239.45 | 221.1125 | 1.195639 |

Identification of PARP-Inhibitor-Synergizing Agents. Given that the HRD gene signature can functionally link transcriptional changes to HR repair deficiency, it was asked whether one could identify agents that would induce the HRD gene signature and thereby induce sensitivity of cancer cells to DNA-damage inducing treatment, such as PARP inhibitor treatment. To try to identify such agents, data from the Connectivity Map were compared with the HRD gene signature. The Connectivity Map is a public database with a large number of drug-associated gene expression profiles (Lamb et al., 2006). The database was search for agents that caused gene expression changes overlapping with the HRD gene signature and therefore might be expected to induce PARP inhibitor sensitivity. Remarkably, the PI3K inhibitors wortmannin and LY-294002, the mTOR inhibitor sirolimus (rapamycin), the HDAC inhibitor vorinostat, and the Hsp90 inhibitor AUY922 were ranked near the top of the Connectivity Map list in terms of inducing the HRD-gene-signature-like gene expression profile.

Figure 4B:
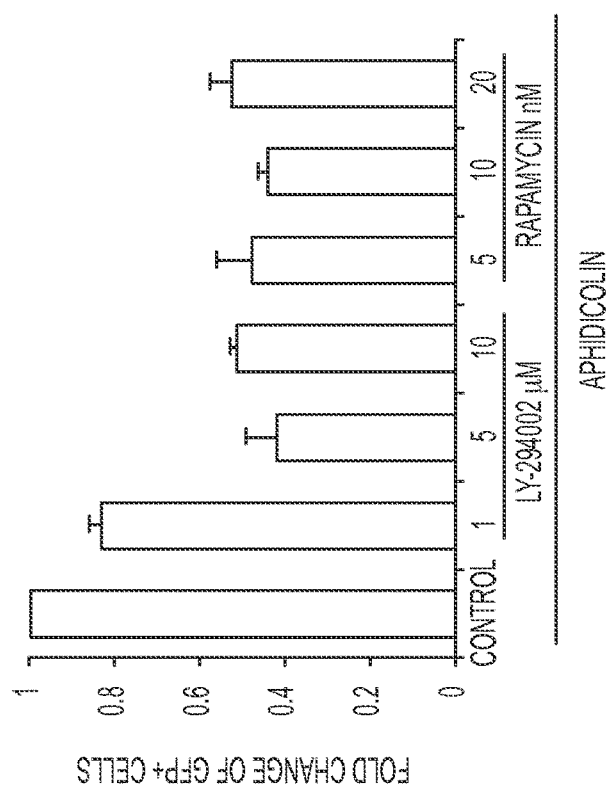
FIGS. 4A-E. Validation of Agents Synergizing with PARP Inhibitors Treatment Predicted by the HRD Gene Signature. (A) U2OS cells were seeded at a high density to allow contact inhibition and transfected with ISceI plasmid to induce DSBs. Then cells were treated with the indicated concentrations of PI3K inhibitor LY-294002 or mTOR inhibitor rapamycin for 16 hr before analysis of GFP-positive cells. (B) U2OS cells were treated with the indicated concentrations of LY-294002 or rapamycin after I-SceI transfection and then treated with replication inhibitor aphidicoline (10 µM) to synchronize cell cycle for 16 hr before the HR repair efficiency analysis. For both a and b, each value is relative to the percentage of GFP-positive cells in I-SceI-transfected control cells. Results are shown as mean±SD from three independent experiments. Student's t-test was used to test statistical significance ($P<0.05$). (C and D) The indicated cancer cell lines were treated with single or combined treatment of PARP inhibitor olaparib (C) or rucaparib (D), with LY-294002 or rapamycin and analyzed by MTT assay. Each value is relative to the value in the cells treated with vehicle control. Results are shown as mean±SEM from three independent experiments. The CI values calculated by CompuSyn software are listed in Tables 6 and 7. (E) The indicated cancer cell lines were treated with PARP inhibitor at 5 or 10 µM. PI3K inhibitor LY-294002 (10 µM) or mTOR inhibitor rapamycin (20 µM) was used in the combination treatment. Cell lines were seeded in 96-well plates, treated with PARP inhibitor or combination treatment at for 5 days, and then analyzed by MTT assay. Each value is relative to the value in the cells treated with vehicle control. Results are show as mean±SD from three independent experiments. Student's t-test showed that the difference between combination treatment and PARP-inhibitor-only treatment was significant ($P<0.05$).
Figure 4A:
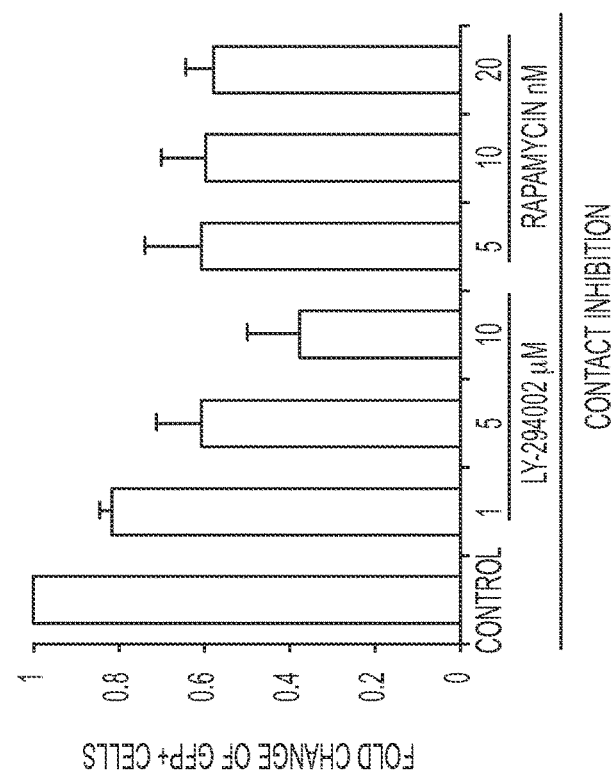
Figure 4C:
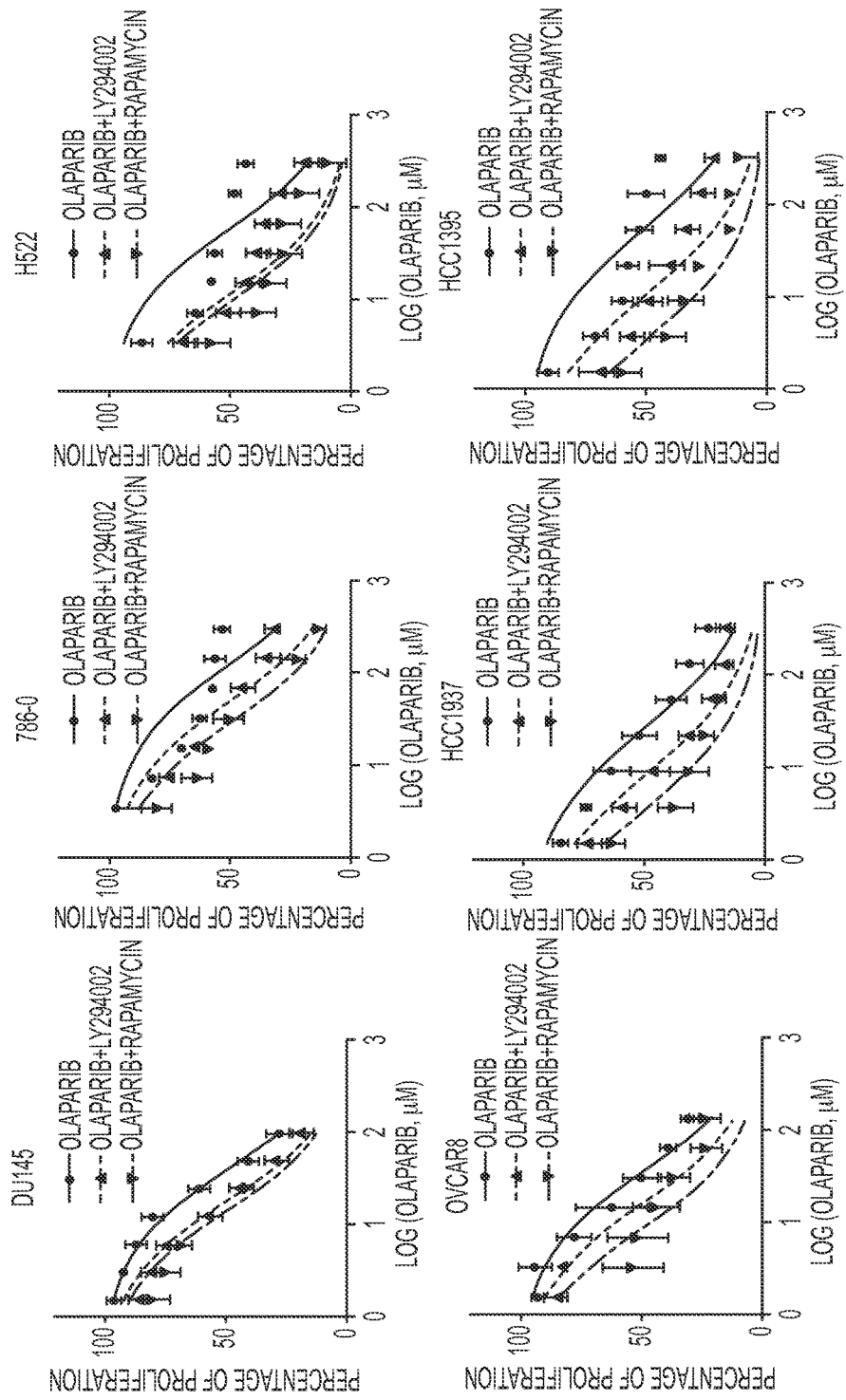
Figure 4D:
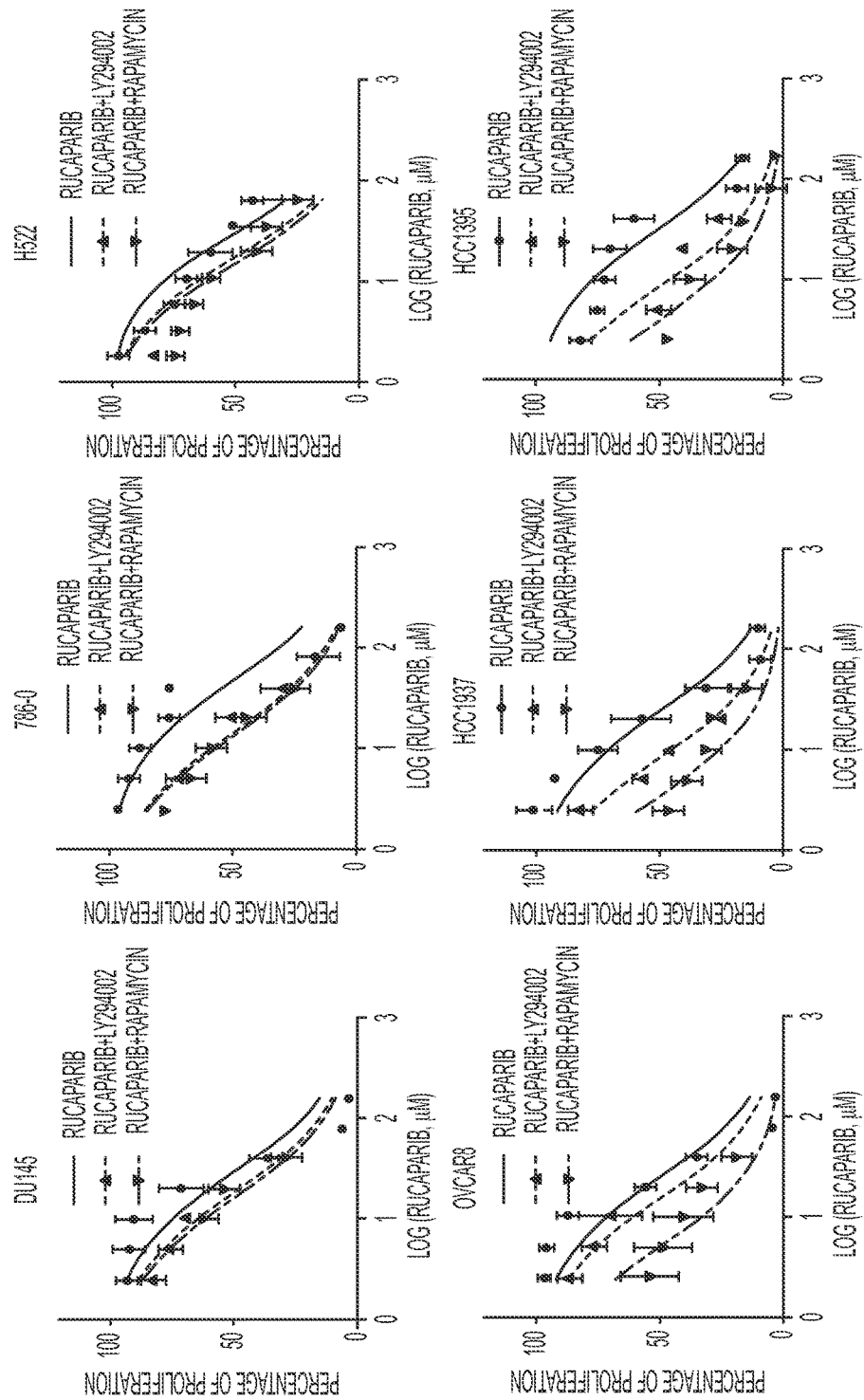
Figure 4E:
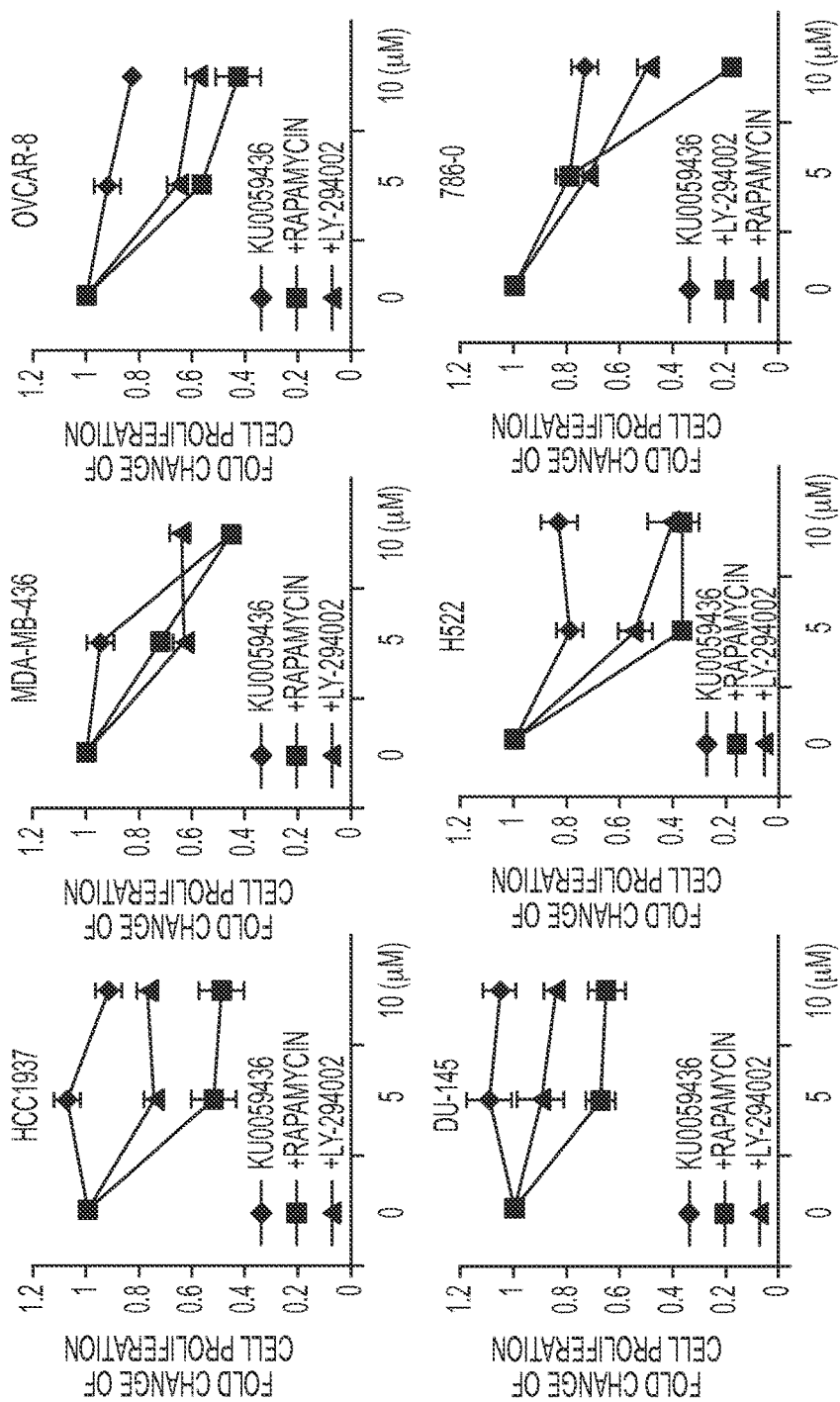

An HR repair assay was used to directly determine the effects of LY-294002 and rapamycin on HR repair. Previous studies have shown that PI3K inhibitor and rapamycin treatment disrupt cell growth signaling and thereby lead to cell cycle arrest at G1 phase (Gao et al., 2004). To exclude any indirect effect of cell cycle distribution on HR repair, contact inhibition (FIG. 15A) and aphidicolin (FIG. 15B), a DNA polymerase inhibitor, were used to block replication and synchronize the cell cycle distribution in the control cells and the cells treated with LY-294002 and rapamycin (FIGS. 4A-B and 15A-B). As expected, LY-294002 and rapamycin significantly reduced HR repair efficiency in both conditions (FIGS. 4A-B). These data support the concept that LY-294002 and rapamycin indeed inhibit HR repair, which led to further assessment as to whether these drugs could sensitize cancer cells to PARP inhibitor treatment. Cancer cell lines of a variety of different cancer types were selected that did not exhibit the HRD gene signature and that showed resistance to PARP inhibitor treatment (FIG. 4E). The degree of synergy of drug combination in a fixed molar ratio was calculated with the combination index (CI) algorithm as previously described (Chou, 2010). In general, CI<1 indicates synergy and CI>1 indicates antagonism. In these cell lines, the combination of LY-294002 or rapamycin synergized with PARP inhibitor olaparib (FIG. 4C and Table 6) or rucaparib (FIG. 4D and Table 7). In addition, rapamycin combined with PARP inhibitors showed an even larger synergistic enhancement of growth inhibition as compared to LY-294002 with PARP inhibitors in the majority of cell lines tested. Consistent with these findings, recent reports have used different approaches to discover that PI3K inhibitors in combination with PARP inhibitors reduce tumor burden in a BRCA1-deficient mouse model and sensitized BRCA-proficient tumors by impairing BRCA1/2 expression (Ibrahim et al., 2012; Juvekar et al., 2012). Furthermore, the synergistic effect of HDAC inhibitor vorinostat (FIG. 15C and Table 8) or Hsp90 inhibitor AUY922 (FIG. 15D and Table 9) on PARP inhibitor treatment in HCC1937 cells was validated. A relatively higher synergy from AUY922 combinations as compared with vorinostat combinations was found. Hence, using the HRD gene signature as a drug discovery framework, the previously reported therapeutic effect from the combination of a PI3K inhibitor (Juvekar et al., 2012; Ibrahim et al., 2012) or Hsp90 inhibitor (Stecklein et al., 2012) with a PARP inhibitor was correctly predicted, and it was discovered that an mTOR inhibitor or an HDAC inhibitor rendered cells sensitive to PARP inhibitor treatment and could be used to develop effective combination therapies that would benefit patients. In addition, the use of the HRD gene signature to efficiently identify drugs that inhibit HR repair provided additional strong evidence that the HRD gene signature is indeed functionally linked the HR-deficiency. Further, it suggests that the HRD gene signature could be systematically used to identify novel genetic and biochemical regulators of HR repair that could both increase the mechanistic understanding and identify rational combinatorial therapies.

TABLE 6

CI values of cancer cell lines treated with olaparib and LY-294002 or rapamycin.

| | | | Combination Index (CI) | | |
|---|---|---|---|---|---|
| Cell lines | Drugs | Molar ratio | ED25 | ED50 | ED75 |
| DU145 | Olaparib:LY294002 | 1.2:1 | 0.921 | 0.891 | 0.905 |
| | Olaparib:Rapamycin | 120:1 | 0.700 | 0.616 | 0.642 |

TABLE 6-continued

CI values of cancer cell lines treated with olaparib and LY-294002 or rapamycin.

| Cell lines | Drugs | Molar ratio | Combination Index (CI) | | |
|---|---|---|---|---|---|
| | | | ED25 | ED50 | ED75 |
| 786-0 | Olaparib:LY294002 | 2.5:1 | 0.615 | 0.850 | 1.289 |
| | Olaparib:Rapamycin | 250:1 | 0.290 | 0.248 | 0.220 |
| H522 | Olaparib:LY294002 | 12.5:1 | 0.121 | 0.204 | 0.541 |
| | Olaparib:Rapamycin | 250:1 | 0.341 | 0.203 | 0.134 |
| OVCAR-8 | Olaparib:LY294002 | 1.2:1 | 0.770 | 0.902 | 1.056 |
| | Olaparib:Rapamycin | 120:1 | 0.803 | 0.466 | 0.902 |
| HCC1937 | Olaparib:LY294002 | 70:3 | 0.314 | 0.439 | 0.619 |
| | Olaparib:Rapamycin | 280:0.3 | 0.556 | 0.447 | 0.464 |
| HCC1395 | Olaparib:LY294002 | 70:3 | 0.267 | 0.407 | 0.777 |
| | Olaparib:Rapamycin | 280:0.3 | 0.847 | 0.456 | 0.248 |

TABLE 7

CI values of cancer cell lines treated with rucaparib and LY-294002 or rapamycin.

| Cell lines | Drugs | Molar ratio | Combination Index (CI) | | |
|---|---|---|---|---|---|
| | | | ED25 | ED50 | ED75 |
| DU145 | Rucaparib:LY294002 | 2:1 | 0.944 | 0.818 | 0.831 |
| | Rucaparib:Rapamycin | 200:1 | 0.900 | 0.728 | 0.796 |
| 786-0 | Rucaparib:LY294002 | 2:1 | 0.402 | 0.488 | 0.596 |
| | Rucaparib:Rapamycin | 200:1 | 0.334 | 0.367 | 0.469 |
| H522 | Rucaparib:LY294002 | 2.5:1 | 0.443 | 0.656 | 0.974 |
| | Rucaparib:Rapamycin | 50:1 | 0.707 | 0.650 | 0.656 |
| OVCAR-8 | Rucaparib:LY294002 | 2:1 | 0.860 | 0.852 | 0.894 |
| | Rucaparib:Rapamycin | 200:1 | 0.807 | 0.273 | 0.382 |
| HCC1937 | Rucaparib:LY294002 | 40:3 | 0.240 | 0.377 | 0.698 |
| | Rucaparib:Rapamycin | 160:0.3 | 0.962 | 0.378 | 0.354 |
| HCC1395 | Rucaparib:LY294002 | 40:3 | 0.707 | 0.506 | 0.364 |
| | Rucaparib:Rapamycin | 160:0.3 | 0.909 | 0.448 | 0.277 |

TABLE 8

CI values of HCC1937 cells treated with olaparib and vorinostat or AUY922.

| Cell lines | Drugs | Molar ratio | Combination Index (CI) | | |
|---|---|---|---|---|---|
| | | | ED25 | ED50 | ED75 |
| HCC1937 | Olaparib:Vorinostat | 20:1 | 0.71 | 0.82 | 0.95 |
| | Olaparib:AUY922 | 875:1 | 0.01 | 0.10 | 0.87 |

TABLE 9

CI values of HCC1937 cells treated with rucaparib and vorinostat or AUY922.

| Cell lines | Drugs | Molar ratio | Combination Index (CI) | | |
|---|---|---|---|---|---|
| | | | ED25 | ED50 | ED75 |
| HCC1937 | Rucaparib:Vorinostat | 80:7 | 0.83 | 0.85 | 0.99 |
| | Rucaparib:AUY922 | 500:1 | 0.21 | 0.32 | 0.54 |

Figure 5A:
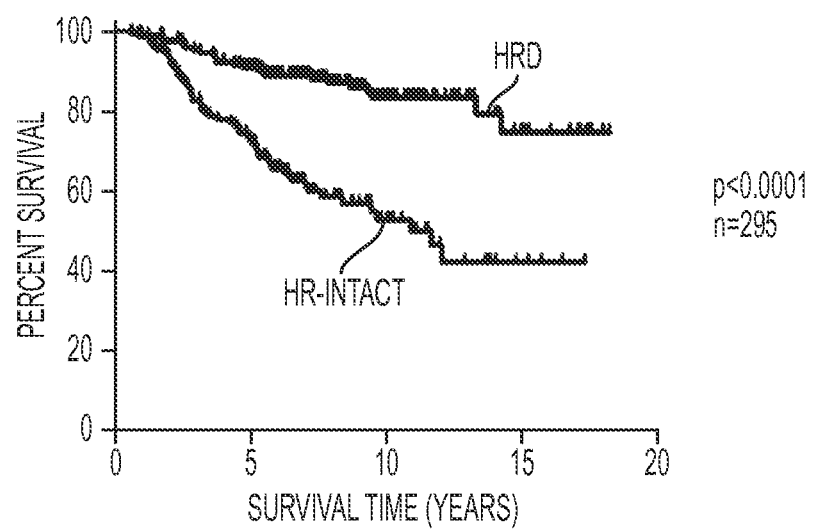
FIGS. 5A-C. The HRD Gene Signature Predicts Overall Survival in Independent Breast and Lung Cancer Patient Cohorts. Datasets from patients with breast (A and B) and lung cancer (C) were clustered into two groups on the basis of whether the gene expression pattern was similar to the HRD gene signature. Kaplan-Meier overall survival curves are shown. Top curves are HRD; bottom curves at HR-Intact. P values are from log-rank test.
Figure 5B:
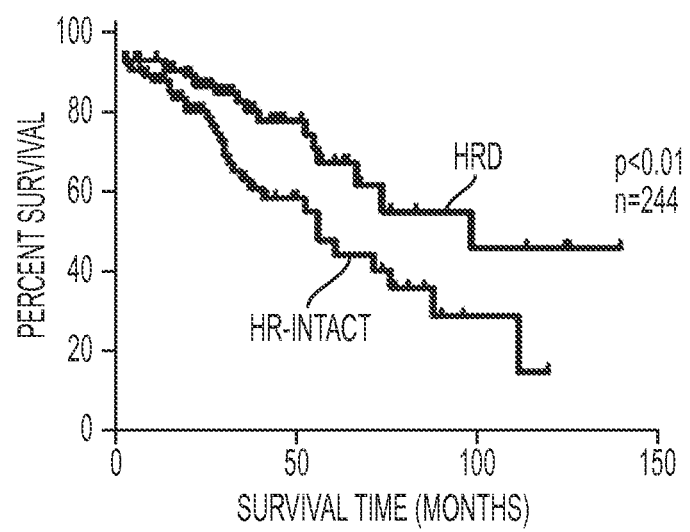
Figure 5C:
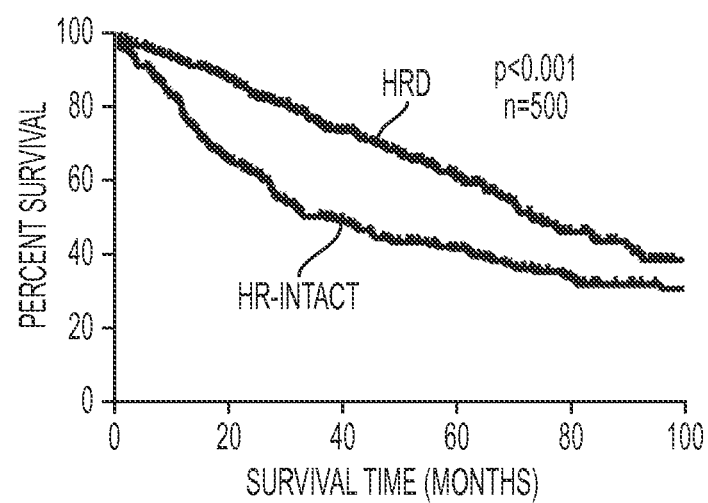

The HRD Gene Signature Predicts Clinical Outcome in Multiple Human Cancers. The HR-defect gene signature was generated from and validated in a well-defined in vitro system. This approach allowed assessment of molecular changes specifically associated with functionally defined HR repair deficiency without perturbations from complex genetic backgrounds found in cancer cells or cancer patient samples. However, use of this approach left unanswered a critical question: Since defects in BRCA1/2 predict patient outcome, is the HRD gene signature sufficient to predict clinical outcome of human cancer? To answer this question, the ability of the HRD gene signature to predict clinical outcome in patients with breast, ovarian, and lung cancer from four independent cancer datasets was examined (FIGS. 5A-C and 16) (see van de Vijver et al., 2002; Oh et al., 2006). Patients were hierarchically clustered into two groups on the basis of similarity of gene expression profiles to the HRD gene signature. Among patients with breast and lung cancers, those with the HRD gene signature had better overall survival than those without the signature (FIGS. 5A-C). In addition, microarray data were generated from 87 ovarian cancer patients, and these data showed results consistent with those in the breast and lung cancer datasets (FIG. 16). These results clearly indicate that HR-deficiency sensitizes cancer cells to DNA damaging inducing therapy, and thus the ability of the HRD gene signature to predict clinical outcomes as a result of different DNA-damage-related treatments.

Example 2

Development of mRNA Markers and Models that Predict Sensitivity to PARP Inhibitors Olaparib (AZD2281) and Rucaparib (AG-014699) are two commonly used PARP inhibitors (PARPi), and their half-maximal inhibitory concentration ($IC_{50}$) data across many breast cancer cell lines are available in the COSMIC database. The gene expression profiles of many of these breast cancer cell lines are also available in the Cancer Cell Line Encyclopedia (CCLE) database. Within the gene expression data, each gene has multiple probes. To perform the analysis, "Duplicate Remover" was used, which is an Excel add-in developed by Ablebits to remove duplicates randomly with the default settings (on the world wide web at ablebits.com/excel-remove-duplicates/index.php). Comparing the COSMIC and CCLE databases, there were 29 breast cancer cell lines having both gene expression and Olaparib $IC_{50}$ data, while 26 breast cancer cell lines had both gene expression and Rucaparib $IC_{50}$ data.

We have recently shown that the 230-gene HRD gene signature has the power to predict sensitivity to PARPi; however, not all 230 genes within the HRD gene signature highly correlate with PARPi sensitivity or directly reflect HR status because many gene expression changes may be secondary consequences of altering the HR network. We therefore created two filtering steps to identify biomarkers that can predict sensitivity to PARPi efficiently and accurately (FIG. 18). The first step applied simple linear regression to assess the correlation between each gene within the HRD gene signature with either Olaparib or Rucaparib $IC_{50}$ values in breast cancer cell lines. A 0.1 regression coefficient was used as the selection cutoff. Genes that had a regression coefficient larger than 0.1 for either Olaparib or Rucaparib were selected for further analysis. Of these, 15 genes correlated with Olaparib response (Table 10) and 38 genes correlated with Rucaparib response (Table 11). The second filtering step was to evaluate whether these genes truly reflect HR status. The HR status of 57 breast cancer cell lines available in the CCLE were characterized by performing supervised clustering using the HRD gene signature. Of these cell lines, 31 were characterized as HR-intact (HRI) and 26 were HR-defect (HRD) (Table 12). Several cell lines from the HRI and HRD groups were experimentally validated using an HR assay. Student's t-test was then applied to check genes selected from the first step whose expression was significantly different between HRI cell lines and HRD cell lines. Genes whose expression difference was not statistically significant are probably not the major contributors in the regulation of HR. Through this filtering step, 10 genes were differentially expressed between HRI and HRD cell lines with p-values less than 0.05 (FIG. 19). These 10 genes were further used to build the models for the prediction of PARPi sensitivity.

TABLE 10

Selected Genes from Filtering Step 1 - Olaparib
Olaparib (AZD2281)

BBOX1
C5orf41
CHEK1
DEPDC1
DLGAP5
FAM43A
FOXO3
HSD11B2
PLCD1
PPL
PROS1
SDCBP2
SERTAD4
SLC45A3
TMEM158

TABLE 11

Selected Genes from Filtering Step 1 - Rucaparib
Rucaparib (AG-014699)

ADM
ALG8
AURKB
BTG2
C11orf82
C4orf34
C6orf48
CCDC138
CCNA2
CDCA5
CDCA8
CHEK1
CSE1L
CTSC
DNMT1
FXYD3
GINS2
GINS4
KIF2C
MOSC1
MRTO4
MSH2
NCAPD3
NFE2L1
OIP5
PHLDA3
POLQ
PROS1
RAD54L
RFC4
RNASEH2A
SDCBP2
SLC45A3
ST6GALNAC2
TK1
TMC4
VAMP5
YPEL5

TABLE 12

HR Status of 57 CCLE Breast Cancer Cell Lines

| HR-Intact | HR-Defect |
|---|---|
| BT20_BREAST | AU565_BREAST |
| BT549_BREAST | BT474_BREAST |
| CAL120_BREAST | BT483_BREAST |
| CAL51_BREAST | CAL148_BREAST |
| CAL851_BREAST | CAMA1_BREAST |
| DU4475_BREAST | EFM19_BREAST |
| HCC1143_BREAST | EFM192A_BREAST |
| HCC1187_BREAST | EVSAT_BREAST |
| HCC1395_BREAST | HCC1419_BREAST |
| HCC1569_BREAST | HCC1428_BREAST |
| HCC1599_BREAST | HCC1500_BREAST |
| HCC1806_BREAST | HCC202_BREAST |
| HCC1937_BREAST | HCC2218_BREAST |
| HCC1954_BREAST | KPL1_BREAST |
| HCC2157_BREAST | MCF7_BREAST |
| HCC38_BREAST | MDAMB134VI_BREAST |
| HCC70_BREAST | MDAMB175VII_BREAST |
| HDQP1_BREAST | MDAMB361_BREAST |
| HMC18_BREAST | MDAMB415_BREAST |
| HS274T_BREAST | MDAMB453_BREAST |
| HS281T_BREAST | T47D_BREAST |
| HS343T_BREAST | UACC812_BREAST |
| HS578T_BREAST | UACC893_BREAST |
| HS606T_BREAST | YMB1_BREAST |
| HS739T_BREAST | ZR751_BREAST |
| HS742T_BREAST | ZR7530_BREAST |
| JIMT1_BREAST | |
| MDAMB157_BREAST | |
| MDAMB231_BREAST | |
| MDAMB436_BREAST | |
| MDAMB468_BREAST | |

Features selected through the two filtering steps were evaluated for their robustness as predictors of drug sensitivity. LASSO regression model (Tibshirani, 1996) combined with the Monte Carlo resampling procedure was used to obtain the robustness score for each feature. The robustness score was calculated as the ratio of frequency that a marker was selected as a predictor over the total number of resampling events during the course of Monte Carlo procedure. The score ranges from 0 to 1. The larger the score, the more robust the marker is as a predictor.

First, the mRNA markers were organized by their robustness scores in descending order (FIG. 20). GLM models were then fit to the top 3-10 mRNA markers to obtain models that contain 3-10 predictors, respectively (FIGS. 21A-H and 22A-H). Then, the intercept and coefficients (weights) of the predictors defined by the GLM models were used to establish mathematic equations, which were then applied to calculate an index for each cell line. The indices were further converted into sensitivity scores using logit function. Finally, the median of the sensitivity scores was used as a cutoff to categorize the cell lines into either resistant (having a score greater than the cutoff) or sensitive (having a score smaller than the cutoff) groups. Models and their sensitivity cutoffs were established and locked in the training set, and without any modification, were used to predict the sensitivity of the testing set. The analysis was performed using R 3.0.2 (available on the world wide web at r-project.org/) and the packages of Bioconductor (available on the world wide web at bioconductor.org/).

Models consisting of 3-10 molecular predictors were developed for the sensitivities of AG014699 and AZD2281 using the Breast Cancer Cell Line Set (Breast Set) and the 3-Disease Set (breast, endometrial, and ovarian cancer cells combined) (FIGS. 23, 24A-H, and 25A-H). Information regarding the three training and testing sets are provided in Table 14. The $IC_{50}$ values for AG014699 and AZD2281 across all cell lines are presented in FIGS. 26A-B. The models were tested with the $GI_{50}$ sensitivity data of the BMN673 testing set. The $GI_{50}$ values for BMN673 across all cell lines are presented in FIG. 27. The correlation of $IC_{50}/GI_{50}$ between each PARP inhibitor is presented in FIG. 28.

TABLE 14

Available Cell Lines mRNA Expression Data

| Data Set | Drug | Breast | Endometrium | Ovary | Total |
|---|---|---|---|---|---|
| Training | AG014699 | 29 | 4 | 12 | 45 |
| Training | AZD2281 | 29 | 5 | 10 | 44 |
| Testing | BMN673 | 25 | 17 | 16 | 58 |

FOXO3 was found to be the most robust marker from the 10 gene marker set across both the breast set and the 3-disease set for both AZD2281 and AG014699. The top 4-10 mRNA markers from the AG014699 breast set models were able to predict sensitivity to BMN673 fairly well. The top 3, 4, 7, 8, 9, and 10 mRNA markers from the AZD2281 breast set models were able to predict sensitivity to BMN673 fairly well. The top 5 and 6 mRNA markers did not predict sensitivity too well for BMN673, although they did still predict with an AUC greater than 0.5. The top 3-10 mRNA markers from both AG014699 and AZD2281 3-disease set models predicted sensitivity well for BMN673.

Example 3

Materials and Methods

Cell Culture, Antibodies, and Chemicals. U2OS cells (American Type Culture Collection, ATCC) were maintained in McCoy's 5A medium supplemented with 10% fetal bovine serum. MCF-10A cells (ATCC) were cultured in mammary epithelial growth medium containing insulin, hydrocortisone, epidermal growth factor, and bovine pituitary extract (Clonetics). EVSAT cells (Creative Bioarray, NY, USA) were cultured in MEM containing 10% fetal bovine serum. MDA-MB-436 cells (ATCC) were maintained in DMEM medium supplemented with 10% fetal bovine serum. PC3, DU145, ACHN, 786-0, H226, H522, OVCAR-3, OVCAR_8, and MCF7 cells were all obtained from ATCC and maintained according to ATCC instructions. BRCA1 (D-9) monoclonal and TTK polyclonal antibodies were purchased from Santa Cruz (SC-6954, 1:1000) and Cell Signaling (#3255, 1:1000), respectively. BRIT1 antibodies and ZNF668 antibodies were generated as previously described (Hu et al., 2011; Peng et al., 2009). ATR (SC-1887, 1:500), CHK1 (SC-8408, 1:500), and RAD51 (H92) antibodies were purchased from Santa Cruz. ATM (#2873, 1:1000), CHK2 (2662, 1:1000), 53BP1 (4937, 1:1000), PTEN (9559, 1:1000) and vinculin (4650, 1:1000) antibodies were from Cell Signaling. RAD51 (PC130) antibody was from Millopore Corp. Western blot analysis was performed as previously described (Peng et al., 2009). PI3K inhibitor LY-294002 and mTOR inhibitor rapamycin were purchased from Sigma. PARP inhibitor KU0059436 (kindly provided by AstraZeneca) was used for cancer cell line experiments. PARP inhibitor olaparib (Selleckchem) was used for other experiments. PARP inhibitor rucaparib, HDAC inhibitor vorinostat and Hsp90 inhibitor AUY922 were from Selleckchem. TTK inhibitor AZ3146 (No. 3994) was purchased from R&D Systems.

Lentiviral Infection and Plasmid siRNA Transfection. MCF-10A cells were infected with individual MISSION lentiviral particles (Sigma) targeting BRCA1, RAD51, BRIT1, PTEN, ATM, ATR, 53BP1, CHK1, CHK2, or BRCA2 according to the manufacturer's instructions. After infection, cells with stable knockdown were selected by using puromycin (1 μg/mL) for 10 to 15 days. For transient transfection, ATM, ATR, 53BP1, CHK1, CHK2, TTK, or ZNF668 was knocked down using SMARTpool siRNAs (Dharmacon) and ZNF668 was knock down by the ON-TARGET-plus ZNF668 siRNA (Charmacon). TTK cDNA was purchased from Harvard Plasmid Core and subcloned using Gateway technology (Invitrogen). In U2OS cells, siRNAs were transfected with oligofectamine (Invitrogen), and plasmid was transfected with FuGENE 6 (Roche). In MCF-10A cells, transfection of plasmids was performed with lipofectamine 2000 (Invitrogen). All shRNA/siRNA sequences are described in Table 15.

TABLE 15

Target sequences of shRNAs/siRNAs.

shRNA

BRCA1-shRNA#1   MISSION ® shRNA Lentiviral Transduction Particles Sequence #4 seq
                CCGGGCCCACCTAATTGTACTGAATCTCGAGATTCAGTACAA
                TTAGGTGGGCTTTTTG (SEQ ID NO: 1)

BRCA1-shRNA#2   MISSION ® shRNA Lentiviral Transduction Particles Sequence #5 seq
                CCGGGCCTACAAGAAAGTACGAGATCTCGAGATCTCGTACTT
                TCTTGTAGGCTTTTTG (SEQ ID NO: 2)

BRIT1-shRNA#1   MISSION ® shRNA Lentiviral Transduction Particles Sequence #1 seq
                CCGGGCCATGTGTTGTGGTTCTTAACTCGAGTTAAGAACCAC
                AACACATGGCTTTTTG (SEQ ID NO: 3)

BRIT1-shRNA#2   MISSION ® shRNA Lentiviral Transduction Particles Sequence #2 seq
                CCGGGCAATGGAGAAGAGATTACAACTCGAGTTGTAATCTCT
                TCTCCATTGCTTTTTG (SEQ ID NO: 4)

RAD51-shRNA#1   MISSION ® shRNA Lentiviral Transduction Particles Sequence #1 seq
                CCGGGCTGAAGCTATGTTCGCCATTCTCGAGAATGGCGAACA
                TAGCTTCAGCTTTTT (SEQ ID NO: 5)

RAD51-shRNA#2   MISSION ® shRNA Lentiviral Transduction Particles Sequence #2 seq
                CCGGCGGTCAGAGATCATACAGATTCTCGAGAATCTGTATGA
                TCTCTGACCGTTTTT (SEQ ID NO: 6)

PTEN-shRNA#1    MISSION ® shRNA Lentiviral Transduction Particles Sequence #1 seq
                CCGGAGGCGCTATGTGTATTATTATCTCGAGATAATAATACA
                CATAGCGCCTTTTTT (SEQ ID NO: 7)

PTEN-shRNA#2    MISSION ® shRNA Lentiviral Transduction Particles Sequence #2 seq
                CCGGCCACAGCTAGAACTTATCAAACTCGAGTTTGATAAGTT
                CTAGCTGTGGTTTTT (SEQ ID NO: 8)

ATM-shRNA#1     MISSION ® shRNA Lentiviral Transduction Particles Sequence #1 seq
                CCGGTGATGGTCTTAAGGAACATCTCTCGAGAGATGTTCCTT
                AAGACCATCATTTTTG (SEQ ID NO: 9)

ATM-shRNA#2     MISSION ® shRNA Lentiviral Transduction Particles Sequence #3
                CCGGGCCTCCAATTCTTCACAGTAACTCGAGTTACTGTGAAG
                AATTGGAGGCTTTTTG (SEQ ID NO: 10)

ATR-shRNA#1     MISSION ® shRNA Lentiviral Transduction Particles Sequence #3

TABLE 15-continued

Target sequences of shRNAs/siRNAs.

|  |  |
|---|---|
|  | CCGGAATGCATTTGGTATGAATCTGCTCGAGCAGATTCATAC CAAATGCATTTTTTG (SEQ ID NO: 11) |
| ATR-shRNA#2 | MISSION ® shRNA Lentiviral Transduction Particles Sequence #4 CCGGCTGTGGTTGTATCTGTTCAATCTCGAGATTGAACAGAT ACAACCACAGTTTTTG (SEQ ID NO: 12) |
| CHK1-shRNA#1 | MISSION ® shRNA Lentiviral Transduction Particles Sequence #3 CCGGGTGGTTTATCTGCATGGTATTCTCGAGAATACCATGCA GATAAACCACTTTTT (SEQ ID NO: 13) |
| CHK1-shRNA#2 | MISSION ® shRNA Lentiviral Transduction Particles Sequence #4 CCGGGTAAACAGTGCTTCTAGTGAACTCGAGTTCACTAGAAG CACTGTTTACTTTTT (SEQ ID NO: 14) |
| CHK2-shRNA#1 | MISSION ® shRNA Lentiviral Transduction Particles Sequence #1 CCGGGAACAGATAAATACCGAACATCTCGAGATGTTCGGTAT TTATCTGTTCTTTTT (SEQ ID NO: 15) |
| CHK2-shRNA#2 | MISSION ® shRNA Lentiviral Transduction Particles Sequence #2 CCGGACGATGCCAAACTCCAGCCAGCTCGAGCTGGCTGGAGT TTGGCATCGTTTTT (SEQ ID NO: 16) |
| 53BP1-shRNA#1 | MISSION ® shRNA Lentiviral Transduction Particles Sequence #1 CCGGGATACTTGGTCTTACTGGTTTCTCGAGAAACCAGTAAG ACCAAGTATCTTTTT (SEQ ID NO: 17) |
| 53BP1-shRNA#2 | MISSION ® shRNA Lentiviral Transduction Particles Sequence #2 CCGGCCAGTGTGATTAGTATTGATTCTCGAGAATCAATACTA ATCACACTGGTTTTT (SEQ ID NO: 18) |
| BRCA2-shRNA#2 | MISSION ® shRNA Lentiviral Transduction Particles Sequence #2 CCGGGCCTTGAATAATCACAGGCAACTCGAGTTGCCTGTGAT TATTCAAGGCTTTTTG (SEQ ID NO: 19) | siRNA

| ATM | Target Sequence: GCAAAGCCCUAGUAACAUA (J-003201-11) (SEQ ID NO: 20) |
|---|---|
|  | Target Sequence: GGUGUGAUCUUCAGUAUAU (J-003201-12) (SEQ ID NO: 21) |
|  | Target Sequence: GAGAGGAGACAGCUUGUUA (J-003201-13) (SEQ ID NO: 22) |
|  | Target Sequence: GAUGGGAGGCCUAGGAUUU (J-003201-14) (SEQ ID NO: 23) |
| ATR | Target Sequence: GAGAAAGGAUUGUAGACUA (J-003202-19) (SEQ ID NO: 24) |
|  | Target Sequence: GCAACUCGCCUAACAGAUA (J-003202-20) (SEQ ID NO: 25) |
|  | Target Sequence: CCACGAAUGUUAACUCUAU (J-003202-21) (SEQ ID NO: 26) |
|  | Target Sequence: CCGCUAAUCUUCUAACAUU (J-003202-22) (SEQ ID NO: 27) |
| CHEK1 | Target Sequence: CAAGAUGUGUGGUACUUUA (J-003255-10) (SEQ ID NO: 28) |
|  | Target Sequence: GAGAAGGCAAUAUCCAAUA (J-003255-11) (SEQ ID NO: 29) |
|  | Target Sequence: CCACAUGUCCUGAUCAUAU (J-003255-12) (SEQ ID NO: 30) |

TABLE 15-continued

Target sequences of shRNAs/siRNAs.

|  |  |
|---|---|
|  | Target Sequence: GAAGUUGGGCUAUCAAUGG (J-003255-13) (SEQ ID NO: 31) |
| CHEK2 | Target Sequence: GUAAGAAAGUAGCCAUAAA (J-003256-17) (SEQ ID NO: 32) |
|  | Target Sequence: GCAUAGGACUCAAGUGUCA (J-003256-18) (SEQ ID NO: 33) |
|  | Target Sequence: GUUGUGAACUCCGUGGUUU (J-003256-19) (SEQ ID NO: 34) |
|  | Target Sequence CUCAGGAACUCUAUUCUAU (J-003256-20) (SEQ ID NO: 35) |
| TP53BP1 | Target Sequence: GGACUCCAGUGUUGUCAUU (J-003548-09) (SEQ ID NO: 36) |
|  | Target Sequence: GAGCUGGGAAGUAUAAAUU (J-003548-08) (SEQ ID NO: 37) |
|  | Target Sequence: GCUAUAUCCUUGAAGAUUU (J-003548-07) (SEQ ID NO: 38) |
|  | Target Sequence: GAAGGACGGAGUACUAAUA (J-003548-06) (SEQ ID NO: 39) |
| TTK | Target Sequence: GAUAAGAUCAUCCGACUUU (J-004105-09) (SEQ ID NO: 40) |
|  | Target Sequence: GCAAUACCUUGGAUGAUUA (J-004105-10) (SEQ ID NO: 41) |
|  | Target Sequence: CCAGUUAACCUUCUAAAUA (J-004105-11) (SEQ ID NO: 42) |
|  | Target Sequence: GAUAGUUGAUGGAAUGCUA (J-004105-12) (SEQ ID NO: 43) |
| ZNF668 | Target Sequence: GUGCCAGCGACUUGCGCAAUU (SEQ ID NO: 44) |
|  | Target Sequence: AAGCCAUACCACUGCGAGAUU (SEQ ID NO: 45) |
| TTK | Target Sequence: GAUAAGAUCAUCCGACUUU (J-004105-09) (SEQ ID NO: 46) |
|  | Target Sequence: GCAAUACCUUGGAUGAUUA (J-004105-10) (SEQ ID NO: 47) |
|  | Target Sequence: CCAGUUAACCUUCUAAAUA (J-004105-11) (SEQ ID NO: 48) |
|  | Target Sequence: GAUAGUUGAUGGAAUGCUA (J-004105-12) (SEQ ID NO: 49) |
| BRCA1 | Target Sequence: CAACAUGCCCACAGAUCAA (J-003461-09) (SEQ ID NO: 50) |
|  | Target Sequence: CCAAAGCGAGCAAGAGAAU (J-003461-10) (SEQ ID NO: 51) |
|  | Target Sequence: UGAUAAAGCUCCAGCAGGA (J-003461-11) (SEQ ID NO: 52) |
|  | Target Sequence: GAAGGAGCUUUCAUCAUUC (J-003461-12) (SEQ ID NO: 53) |

Microarray Analysis and Survival Analysis. Microarray analysis was conducted as previously described (Park et al., 2012). Total RNA was extracted using a mirVana RNA isolation labeling kit (Ambion). We used 500 ng of total RNA for labeling and hybridization based on the manufacturer's procedures (Illumina) Sentrix Human6 v2 Expression Bead Chip and HumanHT-12 v4 Expression Beadchip were used. The bead chips were scanned with a BeadArray Reader (Illumina) After normalization with the Linear Models for Microarray Data (LIMMA) package in the R language environment and log 2-transformation, array data were subjected to further analysis. Primary microarray data are available in the National Center for Biotechnology Information Gene Expression Omnibus public database (Illumina platform, GEO accession number GSE54269). The random-variance t test was used to identify genes differentially expressed between the two classes that were compared using BRB-ArrayTools (Simon et al., 2007). The random-variance t test is an improvement over the standard separate t-test as it allows information to be shared among genes about within-class variation without assuming that all genes have the same variance. Gene expression differences were considered significant if P<0.001. Gene set enrichment analysis was performed using Ingenuity Pathway Program (version 12710793). To define the genes that most significantly changed in BRCA1 (a), PTEN (b), and double knockdown cells (c), a score was signed to each gene using the following formula after their expression levels were compared with expression levels in control cells as described in previous paper (McMurray et al., 2008): a/c+b/c≤1.2 for genes overexpressed in c; c/a+c/b≤1.2 for genes underexpressed in c.

HR Repair Analysis. A schematic diagram of HR repair assay is shown in new FIG. 6A. DR-GFP, pCAGGS, and pCBASce plasmids were kindly provided by Dr. Maria Jasin (Memorial Sloan-Kettering Cancer Center, New York, N.Y.). U2OS cells containing a single copy of the HR repair reporter substrate DR-GFP in a random locus were generated as previously described (Peng et al., 2009). GFP-expressing plasmid (pEGFP-C1) was used for transfection efficiency control. Twenty-four hours after ZNF668 siRNA, TTK plasmid, or BRCA1 siRNA transfection, cells were re-seeded; the next day, cells were transfected with pCBASce plasmids. For cell lines that do not stably contain DR-GFP plasmid, 1×10$^6$ cells were electroporated with 12 ug of DR-GFP and 12 ug pCBASce plasmids at 270 V, 975 uG using a BioRad genepulsar II (Huang et al., 2009). Forty-eight hours to seventy-two hours later, flow cytometry analysis was performed to detect GFP-positive cells using a FACScalibur apparatus with CellQuest software (Becton Dickinson, San Jose, Calif.). Unless otherwise specified, results were mean±SD from three independent experiments.

Flow Cytometry Analysis. Cells were fixed with 70% cold ethanol (−20° C.) overnight and then resuspended in staining solution (10 μg/mL propidium iodide, 20 μg/mL RNAase A, and 0.05% Triton X-100). Cell cycle analysis was performed at the MD Anderson Cancer Center Flow Cytometry and Cellular Imaging Facility. Any given analyses were repeated at least three times.

Cell Proliferation Assay. Cell proliferation was measured by MTT (3-(4,5-dimethylthiazol-2-yl)-2,5-diphenyltetrazolium bromide; Sigma) reduction. To test the cell proliferation rate, 500-1×10$^4$ cells/well were seeded in a 96-well plate in a total volume of 100 μL in triplicate in each experiment. The next day, cells were treated with indicated concentrations of drugs. Five days later, 20 μL of MTT substrate (2 mg/mL) was added to each well and incubated with cells for 3 hr. Then the culture medium was removed, and 100 μL of dimethyl sulfoxide was added. Plates were read at 490 nm and 650 nm (background) in a microplate reader (Molecular Devices). After subtraction of background, the cell viability was calculated as fold change relative to control cells. The OD values were analyzed with Graphpad Prism 6.0 software. Each value is relative to the value in the cells treated with vehicle control. Results are shown as mean±SEM from three independent experiments.

Colony Forming Assay. Cells were seeded at low density and treated with indicated concentrations of drugs the next day; cells were then left for 2 weeks to allow colonies to form. Colonies were stained with staining solution (0.25% crystal violet, 25% methanol in 1×PBS) for colony visualization. Colonies were counted manually (colonies containing 50 or more cells were counted) or digitally using ImageJ software with customized parameters optimized based on three preliminary manual counts or blindly chosen. Unless otherwise stated, each value is relative to the value in the cells treated with vehicle control. Results are shown as mean±SD from three independent experiments.

Drug Combination Studies. Drug combination treatments results were obtained from MTT assays of at least three replications and the combination index (CI) was calculated by CompuSyn software using the Chou-Talalay equation, which takes into account both the potency ($IC_{50}$) and the shape of the dose-effect curve (46). CI<1 indicated synergism, and CI=1 and CI>1 indicated additive and antagonism, respectively.

Survival Analysis. Two independent datasets of breast cancer patients, the Netherlands Cancer Institute (NKI) (47) and University of North Carolina (UNC) (48) cohorts, one dataset of lung cancer patients (505 patients) and one dataset of ovarian cancer patients containing both genome-wide expression data and patient survival data were used for survival analysis. Kaplan-Meier analysis and the log-rank test were used to estimate patient prognosis.

Statistical Analysis. All statistical analysis was performed with a one-tailed Student's t-test.

Proteome Profiling. For proteome analysis, cells were grown in RPMI 1640 supplemented with $^{13}$C-lysine and 10% dialyzed FBS (Taguchi et al., 2011). Cells were lysed in 1 ml of PBS containing the detergent octyl-glucoside (OG)(1% w/v) and protease inhibitors (complete protease inhibitor cocktail, Roche Diagnostics), followed by sonication and centrifugation at 20,000×g with collection of the supernatant. Two mg of whole cell lysate were reduced in DTT and alkylated with iodoacetamide before fractionation with reverse-phase chromatography. Individual fractions were digested in-solution with trypsin and combined into 24 pools based on chromatographic features; pools were analyzed individually on an LTQ-Orbitrap mass spectrometer (Thermo Scientific). Mass spectrometry data were processed by CPAS and spectra searched against a composite database of IPI human (v3.57) and IPI bovine (v3.43). Significance of peptide and protein matches was estimated with PeptideProphet and ProteinProphet. Peptides with a minimum PeptideProphet of 0.05 were submitted to ProteinProphet with a 5% maximum error rate and any unlabeled peptides with bovine homology were discarded (Faca et al., 2008).

* * *

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Adamson et al., A genome-wide homologous recombination screen identifies the RNA-binding protein RBMX as a component of the DNA-damage response. *Nat. Cell Biol.*, 14:318-328, 2012.

Audeh et al., Oral poly(ADP-ribose) polymerase inhibitor olaparib in patients with BRCA1 or BRCA2 mutations and recurrent ovarian cancer: a proof-of-concept trial. *Lancet*, 376:245-251, 2010.

Bouwman et al., 53BP1 loss rescues BRCA1 deficiency and is associated with triple-negative and BRCA-mutated breast cancers. *Nat. Struct. Mol. Biol.*, 17:688-695, 2010.

Bryant et al., Specific killing of BRCA2-deficient tumours with inhibitors of poly(ADP-ribose) polymerase. *Nature*, 434:913-917, 2005.

Bunting et al., 53BP1 inhibits homologous recombination in Brca1-deficient cells by blocking resection of DNA breaks. *Cell*, 141:243-254, 2010.

Ciccia and Elledge, The DNA damage response: making it safe to play with knives. *Mol. Cell*, 40:179-204, 2010.

Chou, Theoretical basis, experimental design, and computerized simulation of synergism and antagonism in drug combination studies. *Pharmacol. Rev.*, 58:621-681, 2006.

Chou, Drug combination studies and their synergy quantification using the Chou-Talalay method. *Cancer Research*, 70:440-446, 2010.

Donawho et al., *Clin. Cancer Res.*, 13:2728-2737, 2007.

Edwards et al., Resistance to therapy caused by intragenic deletion in BRCA2. *Nature*, 451:1111-1115, 2008.

Faca et al., Proteomici analysis of ovarian cancer cells reveals dynamic processes of protein secretion and shedding of extracellular domains. *PLoS One*, 3:e2425, 2008.

Farmer et al., Targeting the DNA repair defect in BRCA mutant cells as a therapeutic strategy. *Nature*, 434:917-921, 2005.

Fong et al., Inhibition of poly(ADP-ribose) polymerase in tumors from BRCA mutation carriers. *N. Engl. J. Med.*, 361:123-134, 2009.

Fraser et al., PTEN deletion in prostate cancer cells does not associate with loss of RAD51 function: implications for radiotherapy and chemotherapy. *Clin. Cancer Res.*, 18:1015-1027, 2012.

Gao et al., G1 cell cycle progression and the expression of G1 cyclins are reguatled by PI3K/AKT/mTOR/p70S6K1 signaling in human ovarian cancer cells. *American J. of Physiol., Cell Physiol.*, 287:C281-291, 2004.

Gagne et al., Quantitative proteomics profiling of the poly (ADP-ribose)-related response to genotoxic stress. *Nuc. Acids Res.*, 40:7788-7805, 2012.

Gelmon et al., Olaparib in patients with recurrent high-grade serous or poorly differentiated ovarian carcinoma or triple-negative breast cancer: a phase 2, multicentre, open-label, non-randomised study. *Lancet Oncol.*, 12:852-861, 2011.

Gupta et al., Cell cycle checkpoint defects contribute to genomic instability in PTEN deficient cells independent of DNA DSB repair. *Cell Cycle*, 8:2198-2210, 2009.

Hanahan and Weinberg, Hallmarks of cancer: the next generation. *Cell*, 144:646-674, 2011.

Helleday et al., DNA repair pathways as targets for cancer therapy. *Nat. Rev. Cancer*, 8:193-204, 2008.

Hu et al., ZNF668 Functions as a Tumor Suppressor by Regulating p53 Stability and Function in Breast Cancer. *Cancer Res.*, 71:6524-6534, 2011.

Huang et al., RAD18 transmits DNA damage signalling to elicit homologous recombination repair. *Nat. Cell Biol.*, 11:592-603, 2009.

Huen and Chen, The DNA damage response pathways: at the crossroad of protein modifications. *Cell Res.*, 18:8-16, 2008.

Ibrahim et al., PI3K inhibition impairs BRCA1/2 expression and sensitizes BRCA proficient triple negative breast cancer to PARP inhibition. *Cancer Discov.*, 2:1036-1047, 2012.

Jackson and Bartek, The DNA-damage response in human biology and disease. *Nature*, 461:1071-1078, 2009.

Jensen et al., Purified human BRCA2 stimulates RAD51-mediated recombination. *Nature*, 467:678-683, 2010.

Juvekar et al., Combining a PI3K inhibitor with a PARP inhibitor provides an effective therapy for a mouse model of BRCA1-related breast cancer. *Cancer Discov.*, 2:1048-1063, 2012.

Konstantinopoulos et al., Gene expression profile of BRCA-ness that correlates with responsiveness to chemotherapy and with outcome in patients with epithelial ovarian cancer. *J. Clin. Oncol.*, 28:3555-3561, 2010.

Krietsch et al., Reprogramming cellular events by poly (ADP-ribose)-binding proteins. *Mol. Aspects Med.*, 34:1066-1087, 2013.

Kummar et al., *J. Clin. Oncol.*, 27:2705-2711, 2009.

Lamb et al., The Connectivity Map: using gene-expression signatures to connect small molecules, genes, and disease. *Science*, 313:1929-1935, 2006.

Levitt and Hickson, Caretaker tumour suppressor genes that defend genome integrity. *Trends Mol. Med.*, 8:179-186, 2002.

Lord and Ashworth, The DNA damage response and cancer therapy. *Nature*, 481:287-294, 2012.

Lukas et al., More than just a focus: The chromatin response to DNA damage and its role in genome integrity maintenance. *Nat. Cell Biol.*, 13:1161-1169, 2011.

Maxwell and Domchek, Cancer treatment according to BRCA1 and BRCA2 mutations. *Nat. Rev. Clin. Oncol.*, 9:520-528, 2012.

McMurray et al., Synergistic response to oncogenic mutations defines gene class critical to cancer phenotype. *Nature*, 453:1112-1116, 2008.

Mendes-Pereira et al., Synthetic lethal targeting of PTEN mutant cells with PARP inhibitors. *EMBO Mol. Med.*, 1:315-322, 2009.

Mills et al., Expression of TTK, a novel human protein kinase, is associated with cell proliferation. *J. Biol. Chem.*, 267:16000-16006, 1992.

Moynahan and Jasin, Mitotic homologous recombination maintains genomic stability and suppresses tumorigenesis. *Nat. Rev. Mol. Cell Biol.*, 11:196-207, 2010.

Neve et al., A collection of breast cancer cell lines for the study of functionally distinct cancer subtypes. *Cancer Cell*, 10:515-527, 2006.

Oh et al., Estrogen-regulated genes predict survival in hormone receptor-positive breast cancers. *J. Clin. Oncol.*, 24:1656-1664, 2006.

Pan et al., A DNA integrity network in the yeast Saccharomyces cerevisiae. *Cell*, 124:1069-1081, 2006.

Park et al., FOXM1 mediates Dox resistance in breast cancer by enhancing DNA repair. *Carcinogenesis*, 33:1843-1853, 2012.

Peng et al., BRIT1/MCPH1 links chromatin remodelling to DNA damage response. *Nat. Cell Biol.*, 11:865-872, 2009.

Rehman et al., Synthetic lethal approaches to breast cancer therapy. *Nat. Rev. Clin. Oncol.*, 7:718-724, 2010.

Saal et al., Recurrent gross mutations of the PTEN tumor suppressor gene in breast cancers with deficient DSB repair. *Nat. Genet.*, 40:102-107, 2008.

Sakai et al., Functional restoration of BRCA2 protein by secondary BRCA2 mutations in BRCA2-mutated ovarian carcinoma. *Cancer Res.*, 69:6381-6386, 2009.

Sakai et al., Secondary mutations as a mechanism of cisplatin resistance in BRCA2-mutated cancers. *Nature*, 451:1116-1120, 2008.

San Filippo et al., Mechanism of eukaryotic homologous recombination. *Annu. Rev. Biochem.*, 77:229-257, 2008.

Saurin et al., Aurora B potentiates Mps1 activation to ensure rapid checkpoint establishment at the onset of mitosis. *Nat. Commun.*, 2:316, 2011.

Scully and Livingston, In search of the tumour-suppressor functions of BRCA1 and BRCA2. *Nature*, 408:429-432, 2000.

Shen et al., Essential role for nuclear PTEN in maintaining chromosomal integrity. *Cell*, 128:157-170, 2007.

Shoemaker, The NCI60 human tumour cell line anticancer drug screen. *Nat. Rev. Cancer,* 6:813-823, 2006.

Simon et al., Analysis of gene expression data using BRB-ArrayTools. *Cancer Inform.*, 3:11-17, 2007.

Sjoblom et al., The consensus coding sequences of human breast and colorectal cancers. *Science*, 314:268-274, 2006.

Slabicki et al., A genome-scale DNA repair RNAi screen identifies SPG48 as a novel gene associated with hereditary spastic paraplegia. *PLoS Biol.*, 8:e1000408, 2010.

Sonoda et al., Rad51-deficient vertebrate cells accumulate chromosomal breaks prior to cell death. *EMBO J.*, 17:598-608, 1998.

Stecklein et al., BRCA1 and HSP90 cooperate in homologous and nonhomologous DNA double-strand break repair and G2/M checkpoint activation, *Proc. Natl. Acad. Sci. USA*, 109:13650-13655, 2012.

Stucke et al., Human Mps1 kinase is required for the spindle assembly checkpoint but not for centrosome duplication. *EMBO J.*, 21:1723-1732, 2002.

Swisher et al., Secondary BRCA1 mutations in BRCA1-mutated ovarian carcinomas with platinum resistance. *Cancer Res.*, 68:2581-2586, 2008.

Taguchi et al., Lung cancer signature in plasma based on proteome profiling of mouse tumor models. *Cancer Cell*, 20:289-299, 2011.

Tibshirani, Regression shrinkage and selection via the lasso. *J. Royal Statist. Soc. B.*, 58:267-288, 1996.

Tutt et al., (2010). Oral poly(ADP-ribose) polymerase inhibitor olaparib in patients with BRCA1 or BRCA2 mutations and advanced breast cancer: a proof-of-concept trial. *Lancet*, 376:235-244, 2010.

van de Vijver et al., A gene-expression signature as a predictor of survival in breast cancer. *N. Engl. J. Med.*, 347:1999-2009, 2002.

Wood et al., Microcephalin/MCPH1 associates with the Condensin II complex to function in homologous recombination repair. *J. Biol. Chem.*, 283:29586-29592, 2008.

Wood et al., The genomic landscapes of human breast and colorectal cancers. *Science*, 318:1108-1113, 2007.

Yun and Hiom, CtIP-BRCA1 modulates the choice of DNA double-strand-break repair pathway throughout the cell cycle. *Nature*, 459:460-463, 2009.

Zhou et al., AMPK mediates a pro-survival autophagy downstream of PARD-1 activation in response to DNA alkylating agents, *FEBS Letters*, 587:170-177, 2013.

---

The invention claimed is:

1. A method of treating ovarian cancer in a cancer patient in need thereof, comprising:
   (a) determining the expression levels of BBOX1, C5orf41, CHEK1, DEPDC1, DLGAP5, FAM43A, FOXO3, HSD11B2, PLCD1, PPL, PROS1, SDCBP2, SERTAD4, SLC45A3, and TMEM158 in a sample of said patient's cancer;
   (b) selecting a patient wherein the expression levels of CHEK1, DEPDC1, SERTAD4, SLC45A3, and TMEM158 are downregulated compared to a non-cancerous sample and the expression levels of BBOX1, FAM43A, FOXO3, HSD11B2, PPL, PROS1, and SDCBP2 are upregulated compared to a non-cancerous sample; and
   (c) administering olaparib to said selected patient to treat said ovarian cancer.

2. The method of claim 1, wherein the ovarian cancer is a BRCA mutant ovarian cancer.

3. The method of claim 1, further comprising a second anti-cancer therapy.

4. The method of claim 3, wherein the second anti-cancer therapy comprises a TTK inhibitor, an mTOR inhibitor, or a PI3K inhibitor.

5. The method of claim 4, wherein the mTOR inhibitor is rapamycin or a rapamycin analog.

6. The method of claim 4, wherein the mTOR inhibitor is an allosteric or catalytic inhibitor.

7. The method of claim 4, wherein the TTK inhibitor is MPI-0479605 or AZ3146.

8. The method of claim 4, wherein in PI3K inhibitor is BEZ 235, BYL 719, BKM 120, or GDC-0941.

* * * * *

UNITED STATES PATENT AND TRADEMARK OFFICE
CERTIFICATE OF CORRECTION

PATENT NO. : 9,850,542 B2
APPLICATION NO. : 14/772549
DATED : December 26, 2017
INVENTOR(S) : Chun-Jen Lin et al.

Page 1 of 1

It is certified that error appears in the above-identified patent and that said Letters Patent is hereby corrected as shown below:

In the Specification

In Column 1, Lines 11-15, delete paragraph and insert:
--This invention was made with government support under Grant Numbers CA112291, CA149186 and CA016672 awarded by the National Institutes of Health and Grant Number W81XWH-10-1-0558 awarded by the U.S. Department of the Army. The Government has certain rights in the invention.--
therefor.

Signed and Sealed this
Tenth Day of April, 2018

Andrei Iancu
*Director of the United States Patent and Trademark Office*